(12) United States Patent
Duffy

(10) Patent No.: US 8,979,541 B2
(45) Date of Patent: *Mar. 17, 2015

(54) METHOD AND SYSTEM FOR QUANTITATIVE ASSESSMENT OF SPATIAL SEQUENCE MEMORY

(71) Applicant: Cerebral Assessment Systems, Inc., Pittsfford, NY (US)

(72) Inventor: Charles Joseph Duffy, Pittsford, NY (US)

(73) Assignee: Cerebral Assessment Systems, Inc., Pittsford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/464,794

(22) Filed: Aug. 21, 2014

(65) Prior Publication Data

US 2014/0356825 A1    Dec. 4, 2014

Related U.S. Application Data

(63) Continuation of application No. 12/561,110, filed on Sep. 16, 2009, now Pat. No. 8,777,630, and a continuation of application No. 12/561,048, filed on Sep. 16, 2009, and a continuation of application No. 14/332,646, filed on Jul. 16, 2014.

(51) Int. Cl.
*G09B 19/00* (2006.01)
*G09B 13/00* (2006.01)
(Continued)

(52) U.S. Cl.
CPC ............... *A61B 5/4064* (2013.01); *A61B 5/16* (2013.01); *A61B 5/162* (2013.01); *A61B 5/168* (2013.01); *A61B 5/4082* (2013.01); *A61B 5/4088* (2013.01); *A61B 5/411* (2013.01);
(Continued)

(58) Field of Classification Search
USPC .................... 600/558; 434/167, 227, 236
See application file for complete search history.

(56) References Cited

U.S. PATENT DOCUMENTS

| 2002/0099305 | A1* | 7/2002 | Fukushima et al. | 600/558 |
| 2006/0270945 | A1* | 11/2006 | Ghajar | 600/558 |
| 2007/0050151 | A1* | 3/2007 | Satoh et al. | 702/19 |

OTHER PUBLICATIONS

Mapstone M, Dickerson K., and Duffy C., Distinct Mechanisms of Impairment in Cognitive Ageing and Alzheimer's Disease, Brain (2008), 131: 1618-1629, Oxford University Press.

(Continued)

*Primary Examiner* — Xuan Thai
*Assistant Examiner* — Michael Grant
(74) *Attorney, Agent, or Firm* — Hulsey Hunt, P.C.

(57) ABSTRACT

A method and system are presented to address quantitative assessment of spatial sequence memory in a subject, where the method comprises the steps of: (1) presenting at least one scene to the subject on a display, the scene comprising a plurality of elements and a background; (2) modulating the saliency of a predetermined section of said scene (3) receiving feedback from the subject via at least one input device; (4) modifying the saliency of the predetermined section; (5) adjusting a functional assessment parameter relative to the scene; (6) moving the predetermined section relative to the scene; (7) receiving refined feedback from the subject via the input device; (8) quantitatively refining the refined feedback; (9) calculating a critical threshold parameter for the subject; and (10) recording the critical threshold parameter onto a tangible computer readable medium.

19 Claims, 41 Drawing Sheets

(51) Int. Cl.
- *A61B 13/00* (2006.01)
- *A61B 5/16* (2006.01)
- *A61B 5/00* (2006.01)
- *G09B 7/00* (2006.01)
- *G09B 7/02* (2006.01)
- *G09B 7/06* (2006.01)

(52) U.S. Cl.
CPC ............... *A61B 5/4842* (2013.01); *G09B 7/00* (2013.01); *G09B 7/02* (2013.01); *G09B 7/06* (2013.01)
USPC ............ 434/236; 434/167; 434/227; 600/558

(56) References Cited

OTHER PUBLICATIONS

Kavcic V. and Duffy C., Attentional Dynamics and Visual Perception: Mechanisms of Spatial Disorientation in Alzheimer's Disease, Brain (2003), 126: 1173-1181, Oxford University Press.

Kavcic V. , Fernandez R., Logan D., and Duffy C., Attentional Dynamics and Visual Perception: Mechanisms of Spatial Disorientation in Alzheimer's Disease, Brain (2006), 129: 736-746, Oxford University Press.

Mapstone M., Logan D., and Duffy C., Cue Integration for the Perception and Control of Self-Movement in Ageing and Alzheimer's Disease, Brain (2006) 129: 2931-2944, Oxford University Press.

Monacelli A., Cushman L., Logan D., and Duffy C., Spatial Disorientation in Alzheimer's Disease: The Remembrance of Things Passed, Neurology (2003) 61, 1491-1497, AAN Enterprises, Inc.

O'Brien H., Tetewsky S., Avery L, Makous W., and Duffy C., Visual Mechanisms of Spatial Disorientation in Alzheimer's Disease, Cerebral Cortex (Nov. 2001) 11: 1083-1092, Oxford University Press.

Cushman L., Stein, K., and Duffy C., Detecting Navigational Deficits in Cognitive Aging and Alzheimer Disease Using Virtual Reality, Neurology (2008) 71: 888-895, American Academy of Neurology.

Cushman L., and Duffy C., The Sex Specificity of Navigational Strategies in Alzheimer Disease, Alzheimer Dis Assoc Disord, vol. 21, No. 2, Apr.-Jun. 2007, Lippincott Williams & Wilkins.

Fernandez R., Kavcic V. , and Duffy C, Neurophysiologic Analyses of Low- and High-Level Visual Processing in Alzheimer Disease, Neurology (2007) 68: 2066-2076 , Jun. 12, 2007, AAN Enterprises, Inc.

Froehler, M. and Duffy C, Cortical Neurons Encoding Path and Place: Where You Go Is Where You Are, Science (2002) 295: 2462-2465, Mar. 29, 2002.

Kavcic V., Fernandez R., Logan D, and Duffy C., Neurophysiological and perceptual correlates of navigational impairment in Alzheimer's disease, Brain (2006) 129: 736-746 Oxford University Press.

\* cited by examiner

FIG. 20

Some Normal Letters — 1450

B C D E F G J K P

Mirror Rotated — 1454

ꓭ ꓑ ꓘ ꓕ ꓞ ꓞ ꓡ ꓷ ꓭ

Inverted — 1458

ꓭ ꓑ ꓘ ꓕ ꓞ ꓞ ꓡ ꓷ ꓭ

3D S/N Gradient

Declining performance consistent with toxic or neurodegenerative dementing illness: anti-Ach Rx contra-incidated, consider AchEl Rx. Clinical correlation and repeated testing for monitoring is advised.

METHOD AND SYSTEM FOR QUANTITATIVE ASSESSMENT OF SPATIAL SEQUENCE MEMORY

CROSS-REFERENCE TO RELATED APPLICATIONS

This application claims priority to U.S. Non-Provisional patent application Ser. No. 12/561,048, filed Sep. 16, 2009, which is hereby incorporated by reference in its entirety as if set forth in full herein.

This application claims priority to U.S. Non-Provisional patent application Ser. No. 12/561,110, filed Sep. 16, 2009, which is hereby incorporated by reference in its entirety as if set forth in full herein.

This application claims priority to U.S. Non-Provisional patent application Ser. No. 14/332,646, filed Jul. 16, 2014, which is hereby incorporated by reference in its entirety as if set forth in full herein.

TECHNICAL FIELD

This disclosure relates in general to the field of psychophysics, and more particularly to perceptual abnormalities associated with sensory and motor processing, and even more particularly to quantitative assessment of functional impairment.

BACKGROUND

Substantial literature exists describing cognitive and visual impairments due to neural dysfunctions, neurodegenerative diseases, and mental disorders. Visual functions, such as shape and motion processing, are impaired by neural dysfunctions. However, many visual abnormalities are unlikely to be uncovered during routine neurological examination.

A method and system for quantitative assessment of functional impairment enables for detection of and indicates diagnosis of a variety of neurological diseases and disorders. A system for sensory-motor quantitative neurocognitive assessment provides continuous feedback adjusted stimulation and its standardized scoring algorithms may provide for diagnosis for early stages of cognitive changes and visual impairments associated with a variety of neurological diseases and disorders. Quantitative assessment may aid in the investigation of cognitive and visual functions at various levels, including, but not limited to, contrast sensitivity, motion detection, depth recognition, and object recognition.

Further, quantitative assessment may indicate diagnosis of neurological diseases and disorders, which include Alzheimer's Disease, Parkinson's Disease, autism, depression, schizophrenia, Asperger's Syndrome, Williams Syndrome, among others. Alzheimer's Disease and Parkinson's Disease are the most common neurodegenerative diseases. Autism and depression are among the most common mental disorders.

Alzheimer's Disease is characterized pathologically by synaptic dysfunction and clinically by a decline in memory and cognition. Further, Alzheimer's Disease may be accompanied by attentional and perceptual deficits, including impaired visual motion and processing. Research studies suggest a perceptual basis of visuospatial disorientation in Alzheimer's Disease. Further, attentional dynamics in Alzheimer's Disease may limit the rate at which visual motion signals can be integrated into a coherent representation of self-movement. Alzheimer's Disease can begin with a wide variety of different symptoms and progresses through recognized clinical stages to include an increasing number of symptoms and worsening functional disability; research studies have demonstrated that all of these changes are accompanied by substantial impairments of perceptual-motor processing.

Currently, Alzheimer's Disease has no cure or preventive therapies, only symptomatic treatments. Diagnosis is usually be established with behavioral assessments and cognitive tests, often followed by one of more types of brain imaging. Researchers have known that Alzheimer's Disease is characterized by impairments in memory deficit and visual functions. Visual impairments in Alzheimer's Disease most commonly occur in motion, depth of field, color, and contrast.

Parkinson's Disease is a neurodegenerative disorder that impairs motor skills, speech, and thought processes, among other functions. Parkinson's Disease may be diagnosed based on clinical evaluations that reveal limb and truncal rigidity, tremor, and a slowing of physical movement and mental events. Non-motor symptoms may include autonomic dysfunction, cognitive abnormalities, sleep disorders, and sensory abnormalities. All of these symptoms are thought to the result of decreased stimulation of the cerebral areas caused by the insufficient formation and action of dopamine.

In addition, people with Parkinson's Disease usually develop some manifest eye movement control and visual processing problems, such as stare because they do not blink as frequently as before, and an inability to respond to visual motion cues that guide postural stabilization reflexes. The eyes may also have trouble fixating on objects and following objects as they move. Parkinson's Disease may impair visual processing and cause symptoms including reduced vision, poor color vision, and difficulties in appreciating the correct location or orientation of an object.

Autism is a brain developmental disorder that is characterized by widespread abnormalities of social interactions and communication. Individuals with autism also have difficulty with processing and responding to sensory information and use visual information inefficiently. Autistic people may have difficulty maintain visual attention and frequently rely on constant scanning of visual information in order to gain meaning, especially in the domain of social cues. Their symptoms reflect their inability to integrate their central and peripheral vision.

Eye movement disorders are common in Autism, but the most prominent visual symptom in autism is the aberrant local and global processing characterized by a superior perception of fine details. Another symptom in autism may be the impaired motion perception that may be also linked to abnormal perceptual integration.

Schizophrenia is a disabling brain disorder characterized by abnormalities in the perception of expression or reality. Much work in the cognitive neuroscience of schizophrenia has focused on attention and memory; however, perceptual functions and visual processing are substantially disrupted in schizophrenia. Schizophrenia may generally associated with deficits in higher-order processing of visual information at a cognitive level. Deficits in contrast sensitivity for moving and static gratings, from discrimination in noise and dot motion discrimination have also been reported in patients with schizophrenia.

People with schizophrenia fail to use contextual information to disambiguate visual information. Poor form processing, particularly object recognition, grouping, perceptual closure, contour integration, face processing, and reading are typically present in people with schizophrenia.

Asperger's Syndrome is an autism spectrum disorder. People with Asperger's Syndrome may show significant difficulties in social interaction, along with other restricted and repetitive patterns of behavior and interests. Asperger's Syndrome may differ from other autism spectrum disorders by its relative preservation of linguistic and cognitive development. However, physical clumsiness and atypical use of language may have been frequently reported. Asperger's Syndrome may begin in infancy or childhood, may have a steady course of decline relative to the age-matched cohort with impairments that may result from maturation-related changes in various systems. However, individuals with Asperger's Syndrome may have excellent basic auditory and visual perception despite impaired higher-order processing of emotional and social signals.

Williams Syndrome is a rare neurodevelopment disorder that may be caused by a deletion of about twenty-six genes from the long arm of chromosome seven. Williams Syndrome may be characterized by a distinctive elfin facial appearance, along with a low nasal bridge; an unusually cheerful demeanor and easer with strangers; mental retardation coupled with unusual language skills; a love for music; and cardiovascular problems, such as supravalvular aortic stenosis and transient hypercalcaemia. Further, individuals with Williams Syndrome may have problems with visual processing, which may be related to difficulty in dealing with complex spatial relationships rather than to issues with depth perception.

In many neural dysfunctions the cognitive capabilities are primarily affected; however, vision is impaired to some degree. The prevalence of basic visual defects raises naturally the question of their impact on cognitive functions and suggests that some cognitive impairments result directly or indirectly from deficiencies at a perceptive level rather than from a core cognitive problem. Hence cognitive impairments and vision impairments can be linked.

Brain imaging techniques and brain-scanning devices have been widely used in investigating cerebral functions and neuro-chemical changes; however, they are of little use in quantifying deficits in visual functions and are burdensome and cost-prohibitive when used to regularly monitor the progress of neurodegenerative disease and mental disorders.

Other tools, such as behavioral assessments and cognitive tests, although cost effective, have drawbacks since they are only adequate for obtaining a qualitative assessment of the visual deficits. Such paper and scoring tests, when given as a sequence of tests, do not consider the results of the initial tests in subsequent tests.

Additionally, since cognitive and sensory impairments are not widely recognized as closely linked, sensory-cognitive testing is not conducted at the same medical visit. Thus, a need exists, therefore, for developing appropriate perceptual tests to quantify the impact of the neural diseases on the affected visual functions.

Further, although some consider behavioral analysis to not be quantifiable, many research studies indicate that functional impairment can indeed analyzed in a quantitative fashion. Thus, a further need exists for an improved system for quantitative assessment of functional impairment to treat subjects with cognitive, perceptual, neurological, visual, and/or attentional deficiencies.

Yet a further need exists to overcome the problem of identifying the early phases of the neural disease or disorder.

A further need exists to overcome the problem of monitoring neural disease progress.

Yet a further need exists for a system for quantitative assessment of functional impairment that has the ability to simplify clinical research on cognitive, perceptual, neurological, visual, and/or attentional deficiencies.

Still further improvement is needed in animal research evaluations wherein varying scene patterns are shown to animal subjects.

Yet a further need exists for laboratories of drug companies and pharmaceutical companies to research and develop treatments for neurological impairment testing of subjects.

Still further improvement is needed to identify meta-parameters that may cause functional impairment and methods to diagnose their exemplary diseases and disorders.

A further need exists to generate real-time scores and diagnosis based on quantitative assessment of functional impairment.

Still further improvement is needed in critical testing of memory, attention, emotional, and social cue analysis.

A need exists for a treatment of development processes that may cause functional impairment in subjects.

Yet a further need exists for maximizing stimulus response compatibility in assessment of functional impairment so as not to obscure aspects of sensory processing and motor control.

Still further improvement is needed in a functional impairment assessment tool that captures all aspects of sensory input, cognitive transformation, and motoric response.

Further, a need exists for the incorporation of artificial intelligence in assessment of functional impairment.

Finally, a need exists for dynamic testing in clinical research, wherein a system responds to the actions of a subject.

BRIEF SUMMARY OF THE INVENTION

The present invention relates to a method for quantitative assessment of functional impairment in a subject, where the method presents scenes to a subject, determines an equilibrated scene parameter of a subject, and generates information that may substantially contribute to a diagnosis. More concretely and with the example of diagnosed functional impairment: A recommended medical intervention, including but not limited to, drugs, medicinal supplements, behavioral programs, and surgical treatments. In one aspect, an apparatus for quantifying assessment of functional impairment in a subject comprising an input device, a display device, a control device, and a tangible computer readable medium. In another aspect, a system of tests for functional impairment tests continuously modulates specific perceptual domains on a stimulus and transitions across perceptual domains in manner to measure the response error relative to a predetermined threshold. In its simplest sense, an assessment profile of functional capacity by psychophysical responses is generated on a tangible computer readable medium. The present disclosure improves and simplifies complex experimental paradigms in the context of psychophysical and electrophysiological studies of spatial or temporal aspects of assessment of functional impairment.

In accordance with the disclosed subject matter, the quantification of the impact of neural diseases onto affected visual functions is provided, thereby substantially reducing problems associated with identifying the early phases of neural diseases and neural disorders, as well as with secondary and tertiary prevention. A need exists for developing appropriate perceptual tests to better understand perceptual deficiencies. The present disclosure teaches a plurality of tests comprising a series of scenes. More specifically, the present disclosure generates and presents complex dynamic scenes, collects responses from a subject, quantitatively refines results, calibrates a display device relative to the interpreted feedback, and determines a diagnosis and medication to a subject.

These and other advantages of the disclosed subject matter, as well as additional novel features, will be apparent from the description provided herein and from the attached figures. The intent of this summary is not to be a comprehensive description of the claimed subject matter, but rather to provide a short overview of some of the subject matter's functionality.

BRIEF DESCRIPTION OF DRAWINGS

The present subject matter will now be described in detail with reference to the drawings, which are provided as illustrative examples of the subject matter so as to enable those skilled in the art to practice the subject matter. Notably, the figures and examples are not meant to limit the scope of the present subject matter to a single embodiment, but other embodiments are possible by way of interchange of some or all of the described or illustrated elements and, further, wherein:

FIG. 20 illustrates an exemplary operator comments entry display;

DETAILED DESCRIPTION OF THE ILLUSTRATED EMBODIMENTS

Figure 1:
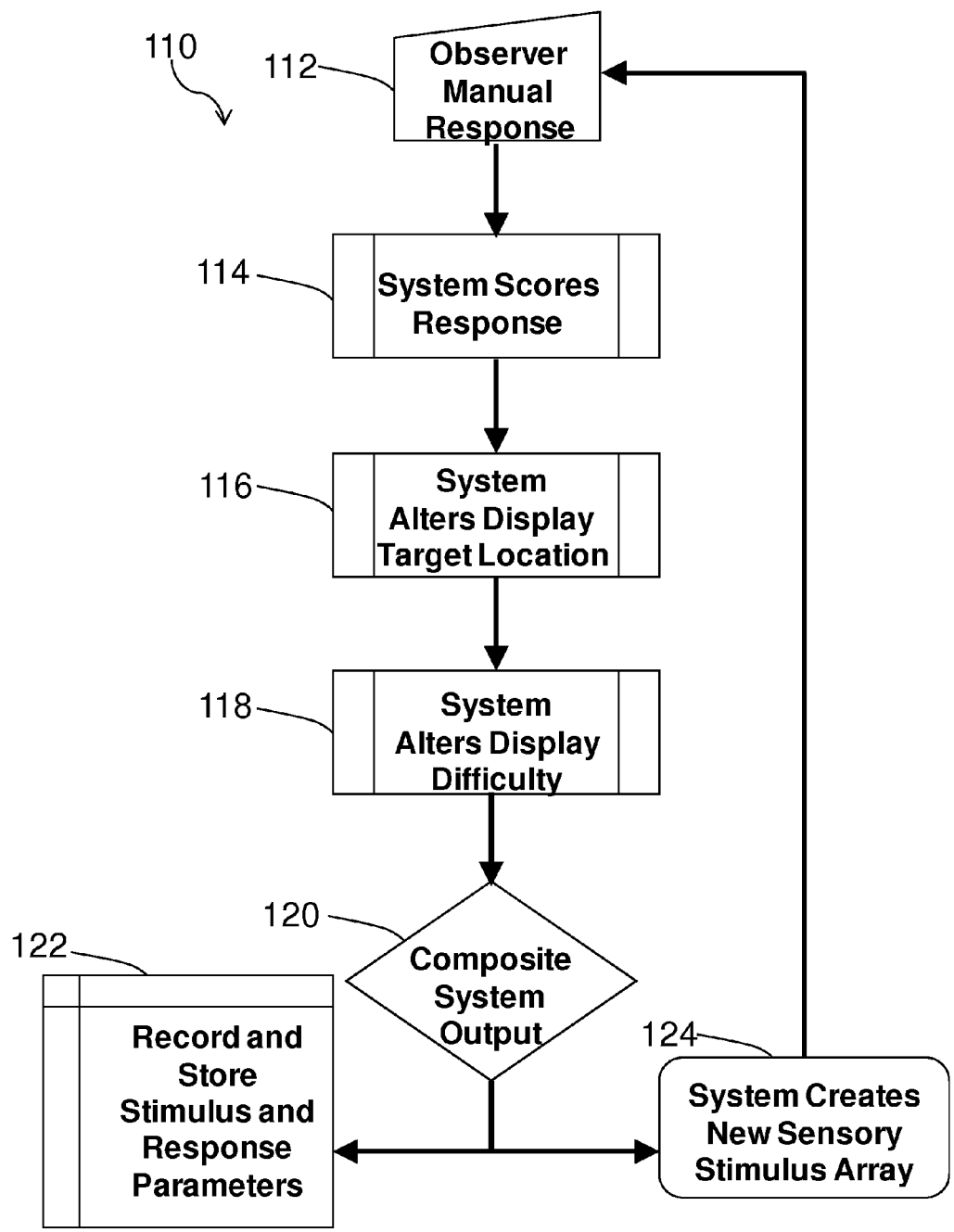
FIG. 1 shows a conceptual framework of the interacting subsystems in the environment that is used to assess functional impairment in a subject.

The present disclosure is related to the subject matter disclosed in the following co-pending applications filed on Sep. 16, 2009 and each naming Charles Joseph Duffy as the inventor: Ser. No. 12/560,583 and entitled METHOD AND SYSTEM FOR QUANTITATIVE ASSESSMENT OF FUNCTIONAL IMPAIRMENT, Ser. No. 12/560,605 and entitled METHOD AND SYSTEM FOR QUANTITATIVE ASSESSMENT OF VISUAL MOTOR RESPONSE, Ser. No. 12/560,642 and entitled METHOD AND SYSTEM FOR QUANTITATIVE ASSESSMENT OF VISUAL CONTRAST SENSITIVITY, Ser. No. 12/560,683 and entitled METHOD AND SYSTEM FOR QUANTITATIVE ASSESSMENT OF VISUAL FORM DISCRIMINATION, Ser. No. 12/560,746 and entitled METHOD AND SYSTEM FOR QUANTITATIVE ASSESSMENT OF VISUAL MOTION DISCRIMINATION, Ser. No. 12/560,916 and entitled METHOD AND SYSTEM FOR QUANTITATIVE ASSESSMENT OF SPATIAL DISTRACTOR TASKS, Ser. No. 12/561,010 and entitled METHOD AND SYSTEM FOR QUANTITATIVE ASSESSMENT OF LETTER IDENTIFICATION LATENCY, Ser. No. 12/561,048 and entitled METHOD AND SYSTEM FOR QUANTITATIVE ASSESSMENT OF VERBAL MEMORY, Ser. No. 12/561,110 and entitled METHOD AND SYSTEM FOR QUANTITATIVE ASSESSMENT OF FACIAL EMOTION SENSITIVITY, Ser. No. 12/561,169 and entitled METHOD AND SYSTEM FOR QUANTITATIVE ASSESSMENT OF FACIAL EMOTION NULLING, and Ser. No. 12/561,188 and entitled METHOD AND SYSTEM FOR QUANTITATIVE ASSESSMENT OF SOCIAL CUES SENSITIVITY.

In describing embodiments of the present invention illustrated in the drawings, specific terminology is employed for the sake of clarity. In the present specification, an embodiment showing a singular component should not be considered limiting. Rather, the subject matter encompasses other embodiments including a plurality of the same component, and vice-versa, unless explicitly stated otherwise herein. Moreover, applicant does not intend for any term in the specification or claims to be ascribed an uncommon or special meaning unless explicitly set forth as such. Further, the present subject matter encompasses present and future known equivalents to the known components referred to herein by way of illustration.

A more full understanding regarding the field of this disclosed subject matter appears in the following patents, all of which have common assignment and inventorship by Charles Joseph Duffy and all of which are incorporated by reference in their entirety for all purposes into this detailed description: U.S. application Ser. No. 10/703,101, entitled "Method for Assessing Navigational Capacity", Duffy et al.; U.S. Pat. No. 6,364,845B1, entitled "Methods for Diagnosing Visuospatial Disorientation Or Assessing Visuospatial Orientation Capacity", Duffy et al.

Further information regarding the field of this disclosed subject matter appears in the following research publications, all of which have common authorship by Charles Joseph Duffy and all of which are incorporated by reference in their entirety for all purposes into this detailed description: Duffy, Charles J. et al., "Attentional Dynamics and Visual Perception: Mechanisms of Spatial Disorientation In Alzheimer's Disease", *Brain*, 126: 1173-1181 (2003); Duffy, Charles J. et al., "Visual Mechanisms of Spatial Disorientation in Alzheimer's Disease", *Cerebral Cortex*, 11: 1083-1192 (2001).

In the present disclosure, the phrase "optic flow" may be defined as the patterned visual motion seen by a moving observer that provides clues about heading direction and the three dimensional structure of the visual environment (Duffy et al., "Visual Mechanisms of Spatial Disorientation in Alzheimer's Disease"). Examples of impaired optic flow perception may include, but are not limited to, elementary visual motion processing deficits and elevated perceptual thresholds. The benefits of the present disclosure can be derived from essentially any analysis of the impaired global pattern recognition of optic flow, impaired visual processing of optic flow, and perceptual mechanisms of visuospatial disorientations, such as the ones previously defined.

In the present disclosure, the word "subject" refers to any animal that may be able to responds to stimuli. The word "subject" may encompasses a human subject, such as a patient. Although the word "subject" is written with the human subject in mind, the word "subject" may be a domestic pet, a work animal, and a robot. More particularly, the word "subject" may include, but is not limited to, a cat, a dog, a rodent, and a monkey. Further, the test referred to in the present disclosure may be implemented in the same manner for animal subject as for human subjects.

In the present disclosure, the word "functional" may include, but is not limited to, cognitive, perceptual, neurological, visual, and/or attentional aspects.

In the present disclosure, the word "qualitative", as referring to qualitative assessment or qualitative monitoring, may refer to a predetermined threshold. A qualitative evaluation may occur when an evaluator, such as the physician or researcher, determines whether the subject may correctly respond to a series of stimuli that probe the underlying sensory, cognitive, and neural mechanisms that may be activated by those stimuli in the setting of a particular response modality. Thus a qualitative score may be established based on a predetermined threshold for passing or failing of a health condition.

In the present disclosure, the word "saliency" and the word "salient" both refer to the means by which behavior is modified regardless of whether the subject is consciously aware. Further, "saliency" refers to the ability to detect something regardless of whether the individual is conscious. Further, "saliency" may be defined in absolute terms but scored relative to a normal group, wherein the normal group can be further defined by single or multiple human characteristics, including, but not limited to, age, gender, medical history, surgical or trauma history, and genetics. Further, the "saliency" of any of the sensory stimuli may be modulated in at least one of the following ways: 1) The "saliency" may be modulated by filtering the spatial frequency composition of the stimuli, thereby making the stimuli harder to see or hear. More particularly, "saliency" may be modulated by filtering that may be associated with visually blurring the stimuli. Further, "saliency" may be modulated by filtering that may be associated with auditorily filtering sound by limiting its frequency bands. 2) The "saliency" may be modulated by filtering the temporal frequency composition of the stimuli to make the stimuli harder to see or hear. More particularly, "saliency" may be modulated by a filtering process that may be associated with visually presenting gaps in the otherwise pseudo-continuous stream of video frames, which may typically be sixty hertz, to a lower value, which may be of forty, thirty, twenty hertz. Additionally, "saliency" may be modulated by a filtering process that may be associated with auditorily creating a high frequency intermittency in the stream of auditory signals.

In the present disclosure, the word "perceptual" may be associated with temporal constraints on visual attention, such as in by limiting the rate at which visual motion signals can be integrated into a coherent representation of self-movement form (Duffy, et al., "Attentional Dynamics and Visual Perception: Mechanisms of Spatial Disorientation In Alzheimer's Disease"). The disclosed subject matter may focus on visual discrimination testing and cognitive capacities associated with visual motion and visual pattern stimuli via control of stimulus selection. However, it is understood that visual discrimination and psychological thresholds may be achieved by other neuropsychological tests, so long as the individual elements assess perceptual impairments or visuospatial disorientation.

In the present disclosure, the phrase "dual task interference" may be associated with distinct tasks that may be combined. Further, "dual task interference" may refer to two functions of the brain interfering with each other. The phrase "dual task interference" may further be defined as creating a critical condition of performing more than one sensory-cognitive-motor task at the same time. A "dual task interference task" may require a subject to be both aware of the movement of a stimulus and also the movement being conducted by the subject. Future equivalents of the present subject matter may be combined in this manner.

In the present disclosure, the phrase "pink noise spatial frequency" may be associated with a signal or process with a frequency spectrum such that the power spectral density is inversely proportional to the frequency. With regards to "pink noise spatial frequency", each octave carries an equal amount of noise power.

In the present disclosure, the word "distractor" may be associated with, but is not limited to: a wedge of unique stimulus elements flashing on for a predetermined time period at a predetermined position, an area of unique elements flashing on for a predetermined time period at a predetermined position, and the transient displacement of a cursor to a predetermined position. The effects of distractors may include, but is not limited to, effects of motion, form, and word stimuli. Further a "distractor" may take a subject from a local processing mode, wherein the subject is processing a particular pattern, to a global processing mode; during this process of transitioning from a local processing mode to a global processing mode, the subject may begun to become distracted. Further, with respect to global motion distractors, if subject switches directly to the global processing mode, then the subject's performance will indicate improvement in the quantitative assessment of functional impairment. Further, with respect to local motion distractors, if subject switches directly to the global processing mode, then the subject's performance will indicate deterioration in the quantitative assessment of functional impairment, indicated by difficulties in functional ability. More particularly, a spatial response curve may indicate the level of difficulty for the subject to switch from a local processing mode to a global processing mode in the presence of a "distractor".

In the present disclosure, the word "cognition" may refer to the relationship between a task and stimulus. Further, the word "cognition" may be associated with the strategic control of how a subject deploys processing resources. Further responses and tasks associated with cognition can be performed in more than one way.

In the present disclosure, the word "attention" may refer to the ability of a subject to perform any of the functional impairment assessment tests of the present disclosure in the presence of distractor stimuli. Further, "attention" may refer to attaining a performance measure without distractors and continuing the functional impairment test while implementing the distractors to further evaluate the subject performance.

In the present disclosure, the word "luminance" may refer to the brightness of a stimulus; the total light emitted.

In the present disclosure, the word "contrast" may refer to the difference between the most and the least luminant elements in a visual display.

In the present disclosure, the word "meta-parameter" may refer to stimulus attributes that may extend across a variety of specific stimulus arrays and response modalities.

In the present disclosure, the word "aspect ratio" may refer to the relative magnitude of orthogonal dimension of a stimulus element.

In the present disclosure, the word "coherence" may refer to the uniformity of a stimulus with respect to some parameter that may be applied across the extent of the stimulus.

In the present disclosure, the word "eccentricity" may refer to the distance from the center of a stimulus or the center of a subject's direction of gaze.

In the present disclosure, the word "facial expression" may refer to the configuration of facial features including the movement and tone of facial muscles.

In the present disclosure, the word "happiness" may refer to the affective state of positive experience leading to a real or perceived increase in the subject's propensity to be attracted to that state.

In the present disclosure, the word "sadness" may refer to the affective state of negative experience leading to a real or perceived decrease in the subject's propensity to be attracted to that state.

In the present disclosure, the word "aggressiveness" may refer to a greater tendency toward, or probability of, an individual's reacting in a violent, intrusive, or threatening manner. Further, "aggressiveness" may be associated with, but is not limited to, any of the following: arms being raised, an erect posture, and an open-mouthed grimace.

In the present disclosure, the word "submissiveness" may refer to a lesser tendency toward, or probability of, an individual's reacting in a violent, intrusive, or threatening manner. Further, "submissiveness" may be associated with, but is not limited to, any of the following: arms being folded, rounded shoulders, and down-cast eyes.

In the present disclosure, the word "body image" may refer to an individual's internal representation of their own body or the appearance of their own body to others.

The present disclosure describes a method, system, and tangible computer readable medium for quantitative assessment of functional impairment in a subject. Complex experimental paradigms in the context of psychophysical and electrophysiological studies of spatial or temporal aspects of assessment of functional impairment are greatly improved and simplified.

Further, the disclosed subject matters also focuses on the quantification of the impact of neural diseases onto affected visual functions, but it is understood to be that the concepts presented also allow significant improvements with the identification of the early phases of neural diseases and neural disorders, as well as with secondary and tertiary prevention. Moreover the disclosed subject matter provides an indication for the potential diagnosis of neural diseases and neural disorders.

Exemplary embodiments of the present invention are directed towards methods for organizing and standardizing data from scene testing that serves as a diagnostic metric for patients with functional impairment symptoms, particularly with associated with cognitive, perceptual, neurological, visual, and/or attentional deficiencies, such as those associated with Alzheimer's Disease, Parkinson's Disease, dementia, attention deficit, autism, and schizophrenia. More particularly on dementia, the exemplary embodiments of the present disclosure provide an indication of vascular dementia and frontotemporal dementia.

As will be understood by those of skill in the art, the present invention may be practiced in other specific forms without departing from the essential characteristics thereof. For example, quantitative assessment of functional impairment in a subject can have a plurality of psychophysical and electrophysiological tests. Or that the psychophysical and electrophysiological tests may include only a subset of the test described above, or all of the tests. Furthermore, the order in which the tests are administered may be varied to suit particular assessment scenarios. Accordingly, the foregoing is intended to be illustrative, but not limiting of the scope of the invention, which is set forth in the following claims.

The foregoing description of the disclosed embodiments is not meant to be limiting. The above description of the disclosed embodiments is meant to enable any person skilled in the art to make or use the claimed subject matter. Various modifications to these embodiments will be readily apparent to those skilled in the art, and the generic principles defined herein may be applied to other embodiments without the use of the innovative faculty.

In the present specification, an embodiment showing a singular component should not be considered limiting. Rather, the subject matter encompasses other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present subject matter encompasses present and future known equivalents to the known components referred to herein by way of illustration:

FIG. 1 shows a conceptual framework of the interacting subsystems 110 in the environment that is used to assess functional impairment in a subject. During the functional assessment process, the step of observer manual response manual 112 is followed by the step of system score response 114, which is immediately followed by the step of system alerts display target location 116. Upon completing step 116, the step of system alters display difficulty 118 occurs, which is immediately followed by the decision of composite system output 120. Thereafter, a decision is made to either proceed with the step of record and store stimulus and response parameters 122 or the step of system creates new sensory stimulus array 124. If the decision is to proceed with the step of system creates new sensory stimulus array 124, then the step of observer manual response manual 112 occurs, thereby repeating the ensuing steps involved in the conceptual framework of the interacting subsystems 110.

Figure 2:
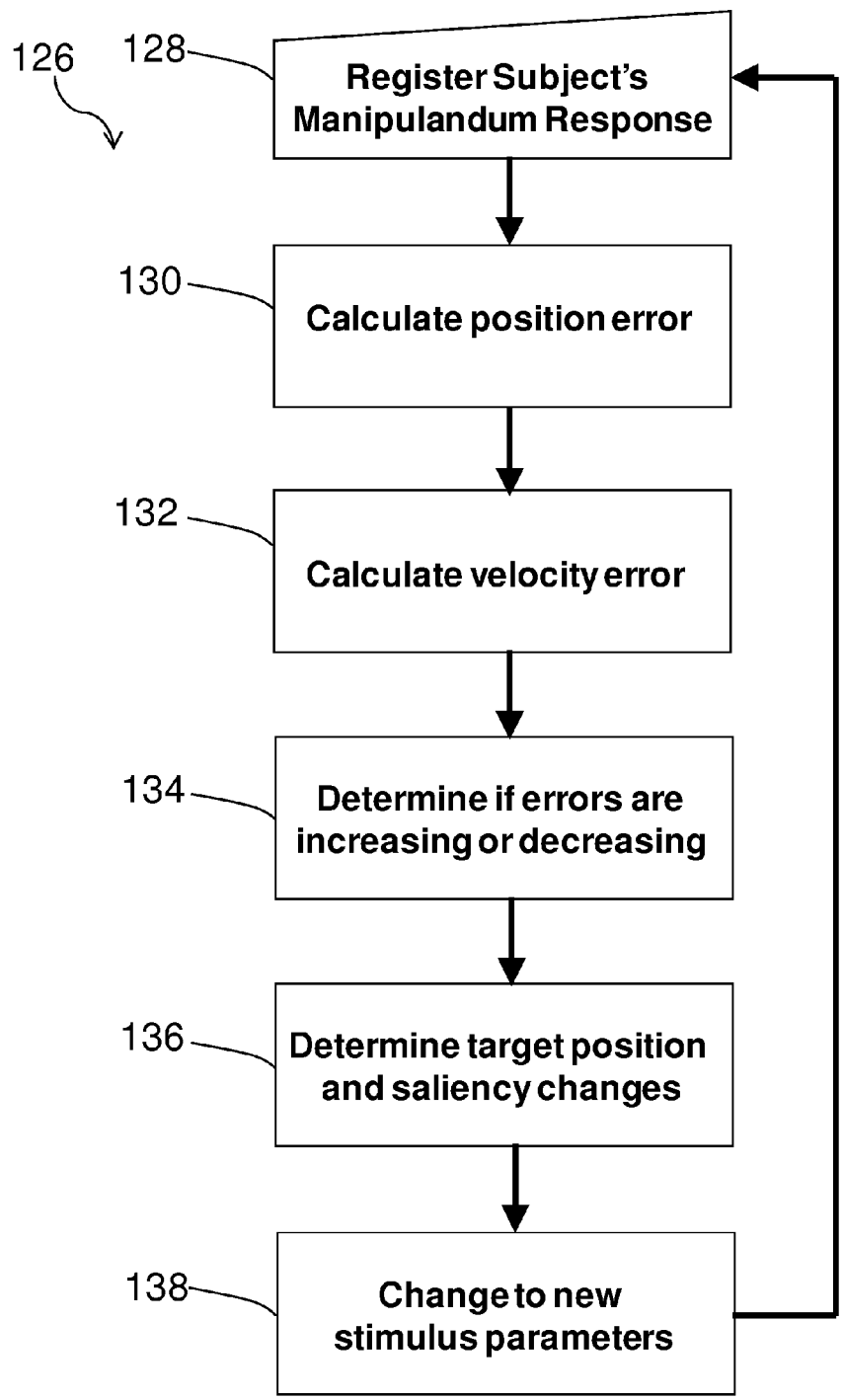
FIG. 2 displays a workflow of running the method to assess functional impairment in a subject.

FIG. 2 displays a workflow of running the method to assess functional impairment in a subject. The workflow of functional impairment 126 begins with the step of register subject's manipulandum response 128. Immediately thereafter is the step of calculate position error 130, which is followed by the step of calculate velocity error 132. After step 132, the step of determine if errors are increasing or decreasing 134 occurs, which is followed by the step of determine target position and saliency changes 136. Immediately thereafter, the step of change to new stimulus parameter 138 occurs; thereafter, is the step of step of register subject's manipulandum response 128, which results in repeating the ensuing steps of the workflow of functional impairment 126.

Figure 3:
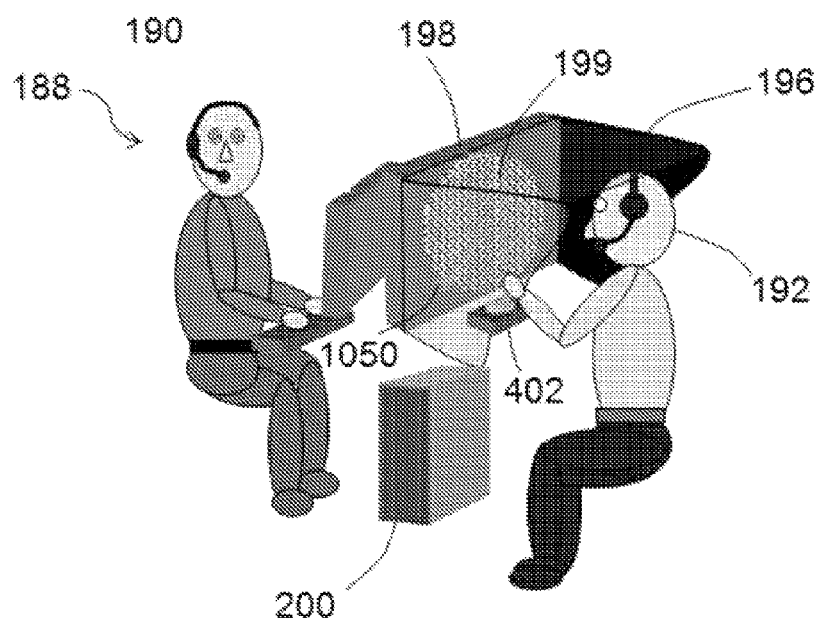
FIG. 3 depicts a test environment, including a mounted shroud-box enclosure that may shield the subject from visual distractors.

FIG. 3 depicts a test environment 188 that may be associated with quantitative assessment of functional impairment. The test environment 188 may include, but is not limited to those associated with research and development laboratories, such as those present at medical centers, universities, drug companies, and pharmaceutical companies. Further, quantitative assessment of functional impairment may be conducted in clinics as well as animal research facilities. The present subject matter may be implemented in future known equivalents.

Further, quantitative assessment of functional impairment may be conducted remotely from any physical location via the Internet or other network. In addition, the present disclosure may be utilized for performing therapy, screening tests or more formal evaluations over the Internet.

The present disclosure may provide a test environment 188, which may include a versatile psychophysical testing environment that simplifies complex experimental paradigms. The present disclosure may assist clinicians and/or researchers with replicating fundamental studies and better investigating visual functions that are impaired by aging and neural dysfunctions, such as shape and motion processing.

Further, the exemplary test environment 188, which is depicted in FIG. 3, may include a mounted shroud-box enclosure that may shield the subject 192 from visual distractors. In systems designed for quantitative assessment of functional impairment, a variety of component and devices comprise the necessary equipment. The test environment 188 in the present disclosure may include, but is not limited to, a subject 192, operator 190, subject display 198, stimulus area 199, operator display 194, a subject manipulanduam 402, a shroud 196, a subject earphones and a subject microphone, an operator earphones and an operator microphone, and a computing system 200. Further, the subject headset 426, which may include a subject earphones and a subject microphone, is shown in greater detail in FIG. 8. Further, the operator headset 424, which may include an operator earphones and an operator microphone, is shown in greater detail in FIG. 8. More particularly, the computing system 200 is shown in greater detail in FIG. 4.

The stimulus area may be presented on the subject display 198 and/or the subject earphones, wherein the subject earphones may be a component of subject headset 426. Further, the cursor 1050 may be located on the subject display 198. The cursor 1050 may extend from the center of the stimulus area 199 to the edge of a stimulus area 199, such as a circular border 1302, which is shown in greater detail in FIG. 25.

Further, the cursor 1050 may be the same cursor that is implemented in multiple tests of the present disclosure, with the exception of superimposed tests. More particularly, functional impairment tests that include superimposed phenomena, may require the alignment of one target area with another target area, thereby requiring more than one cursor 1050.

Further, the test environment 188 may include a mount device, which may be a pull-mount or a desk-mount. Further, the subject display 198 may include, but is not limited to, a display screen that is linked the computing system by a digital cable. The display screen may be used to display instructions, to display an image of the operator 190 during instructions or coaching, or to present the visual test stimuli. The display device 22 may include, or could have as attached, a video camera directed at the subject 192 to show an image of the subject 192 on operator display 194. The subject display 198, which is that of the subject 192, may include a shroud 196 mounted onto a box, in the form of a shroud-mounted box, in order to shield the subject 192 from the visual distractors, or may also include earphones in order to present stimuli and shield the subject from audible distractors.

Figure 4:
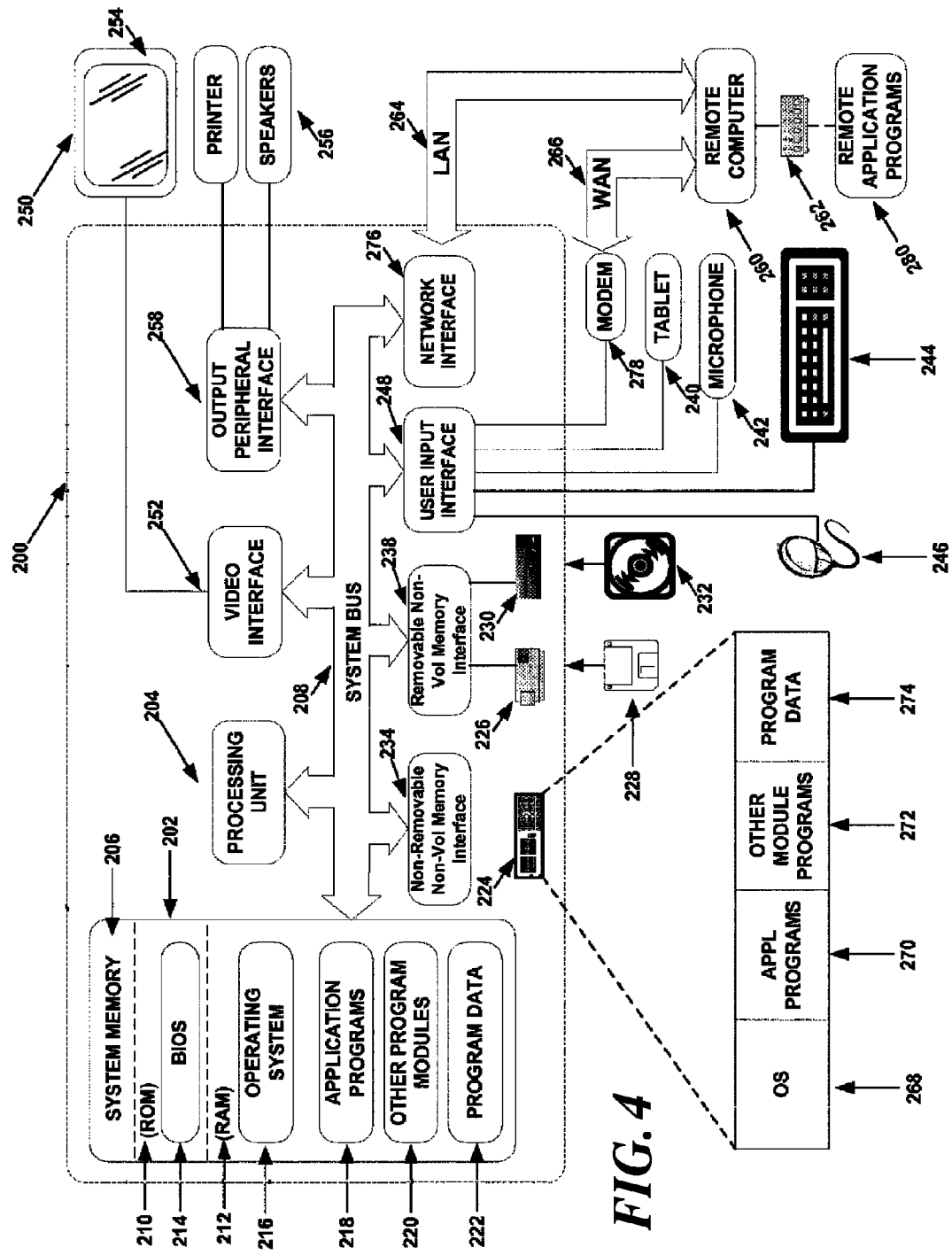
FIG. 4 shows the computing system used that may be used in the quantitative assessment of functional impairment.

With reference to FIG. 4, an exemplary system within a computing environment for implementing the invention includes a general purpose computing device in the form of a computing system 200, commercially available from Intel, IBM, AMD, Motorola, Cyrix and others. Components of the computing system 202 may include, but are not limited to, a processing unit 204, a system memory 206, and a system bus 236 that couples various system components including the system memory to the processing unit 204. The system bus 236 may be any of several types of bus structures including a memory bus or memory controller, a peripheral bus, and a local bus using any of a variety of bus architectures.

Computing system 200 typically includes a variety of computer readable media. Computer readable media can be any available media that can be accessed by the computing system 200 and includes both volatile and nonvolatile media, and removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data.

Computer memory includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing system 200.

The system memory 206 includes computer storage media in the form of volatile and/or nonvolatile memory such as read only memory (ROM) 210 and random access memory (RAM) 212. A basic input/output system 214 (BIOS), containing the basic routines that help to transfer information between elements within computing system 200, such as during start-up, is typically stored in ROM 210. RAM 212 typically contains data and/or program modules that are immediately accessible to and/or presently being operated on by processing unit 204. By way of example, and not limitation, an operating system 216, application programs 220, other program modules 220 and program data 222 are shown.

Computing system 200 may also include other removable/non-removable, volatile/nonvolatile computer storage media. By way of example only, a hard disk drive 224 that reads from or writes to non-removable, nonvolatile magnetic media, a magnetic disk drive 226 that reads from or writes to a removable, nonvolatile magnetic disk 228, and an optical disk drive 230 that reads from or writes to a removable, nonvolatile optical disk 232 such as a CD ROM or other optical media could be employed to store the invention of the present embodiment. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 224 is typically connected to the system bus 236 through a non-removable memory interface such as interface 234, and magnetic disk drive 226 and optical disk drive 230 are typically connected to the system bus 236 by a removable memory interface, such as interface 238.

The drives and their associated computer storage media, discussed above, provide storage of computer readable instructions, data structures, program modules and other data for the computing system 200. For example, hard disk drive 224 is illustrated as storing operating system 268, application programs 270, other program modules 272 and program data 274. Note that these components can either be the same as or different from operating system 216, application programs 220, other program modules 220, and program data 222. Operating system 268, application programs 270, other program modules 272, and program data 274 are given different numbers hereto illustrates that, at a minimum, they are different copies.

A user may enter commands and information into the computing system 200 through input devices such as a tablet, or electronic digitizer, 240, a microphone 242, a keyboard 244, and pointing device 246, commonly referred to as a mouse, trackball, or touch pad. These and other input devices are often connected to the processing unit 204 through a user input interface 248 that is coupled to the system bus 208, but may be connected by other interface and bus structures, such as a parallel port, game port or a universal serial bus (USB).

A monitor 250 or other type of display device is also connected to the system bus 208 via an interface, such as a video interface 252. The monitor 250 may also be integrated with a touch-screen panel or the like. Note that the monitor 250 and/or touch screen panel can be physically coupled to a housing in which the computing system 200 is incorporated, such as in a tablet-type personal computer. In addition, computers such as the computing system 200 may also include other peripheral output devices such as speakers 254 and printer 256, which may be connected through an output peripheral interface 258 or the like.

Computing system 200 may operate in a networked environment using logical connections to one or more remote computers, such as a remote computing system 260. The remote computing system 260 may be a personal computer, a server, a router, a network PC, a peer device or other common network node, and typically includes many or all of the elements described above relative to the computing system 200, although only a memory storage device 262 has been illustrated. The logical connections depicted include a local area network (LAN) 264 connecting through network interface 276 and a wide area network (WAN) 266 connecting via modem 278, but may also include other networks. Such networking environments are commonplace in offices, enterprise-wide computer networks, intranets and the Internet.

For example, in the present embodiment, the computer system 200 may comprise the source machine from which data is being generated/transmitted, and the remote computing system 260 may comprise the destination machine. Note however that source and destination machines need not be connected by a network or any other means, but instead, data may be transferred via any media capable of being written by the source platform and read by the destination platform or platforms.

The central processor operating pursuant to operating system software such as IBM OS/2®, Linux®, UNIX®, Microsoft Windows®, Apple Mac OSX® and other commercially available operating systems provides functionality for the services provided by the present invention. The operating system or systems may reside at a central location or distributed locations (i.e., mirrored or standalone).

Software programs or modules instruct the operating systems to perform tasks such as, but not limited to, facilitating client requests, system maintenance, security, data storage, data backup, data mining, document/report generation and algorithms. The provided functionality may be embodied directly in hardware, in a software module executed by a processor or in any combination of the two.

Furthermore, software operations may be executed, in part or wholly, by one or more servers or a client's system, via hardware, software module or any combination of the two. A software module (program or executable) may reside in RAM memory, flash memory, ROM memory, EPROM memory, EEPROM memory, registers, hard disk, a removable disk, a CD-ROM, DVD, optical disk or any other form of storage medium known in the art. An exemplary storage medium is coupled to the processor such that the processor can read information from, and write information to, the storage medium. In the alternative, the storage medium may be integral to the processor. The processor and the storage medium may also reside in an application specific integrated circuit (ASIC). The bus may be an optical or conventional bus operating pursuant to various protocols that are well known in the art.

Figure 5:
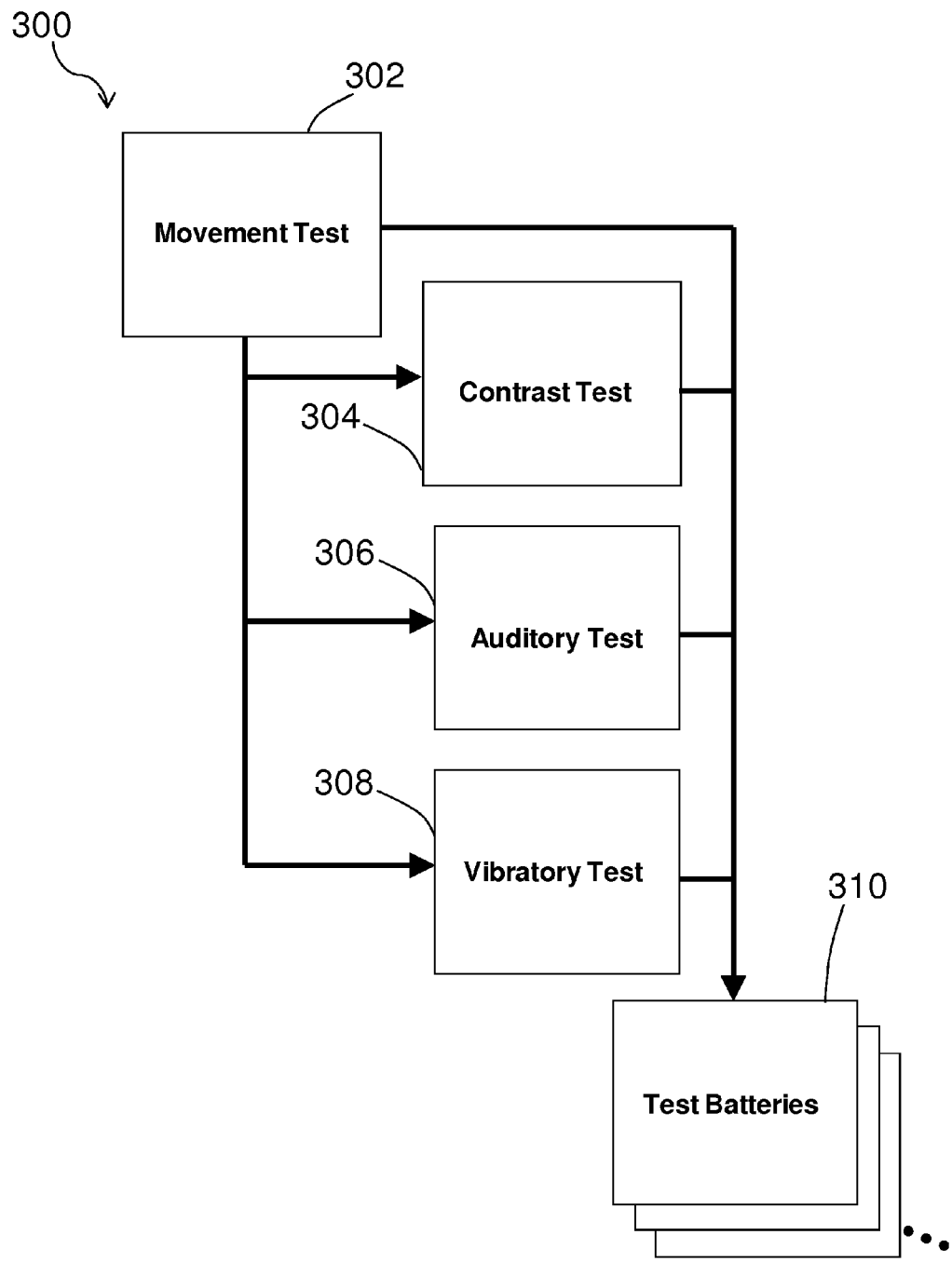
FIG. 5 shows the paradigm of a hierarchical nature of parametric individualization.

FIG. 5 shows the paradigm of a hierarchical nature of parametric individualization. The word "hierarchical" refers to some tests that may derive measures that may be used as pre-set. Further, the word, "hierarchical" is associated with the occurrence of start values in subsequent tests, such that there may be an ordered sequence of tests. In the hierarchy for parametric individualization 300, the resulting date from a movement test 302 may be applied to a contrast test 304, an auditory test 306, and/or a vibratory test 308. The results of the one particular test or a combination of tests that may include, but are not limited to, a contrast test 304, an auditory test 306, and/or a vibratory test 308, may be applied to the test batteries 310, which are further described in the present disclosure.

Figure 6:
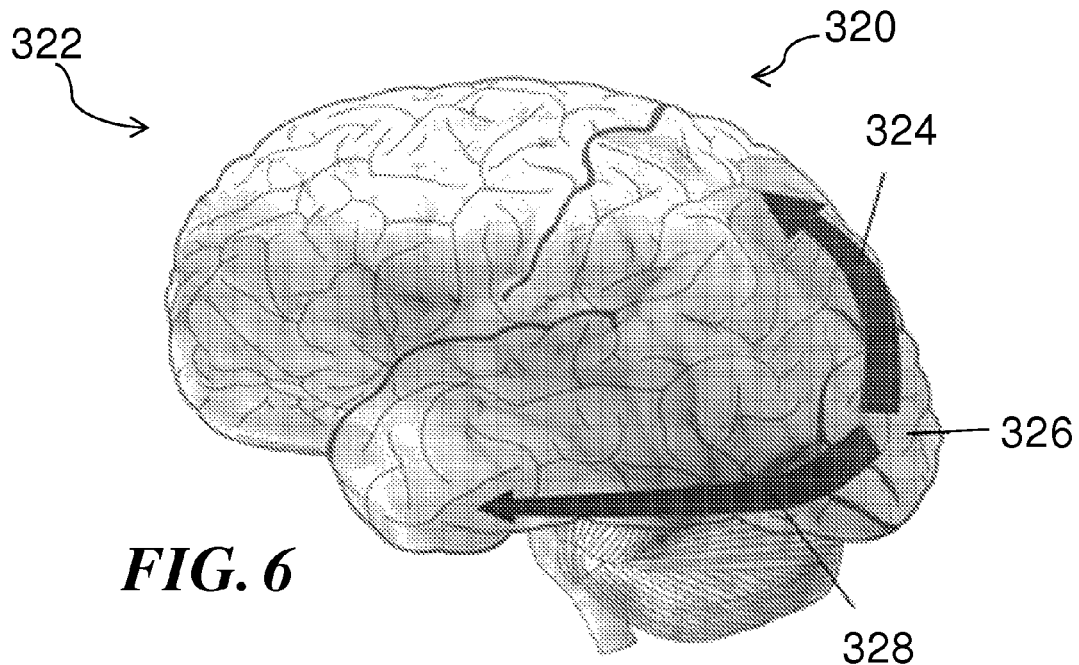
FIG. 6 portrays a representation of left posterior-lateral view of the human brain.

FIG. 6 portrays a representation of left posterior-lateral view 320 of the human brain 322. The human visual system is a system of parallel pathways. In the eyes, there are two sensory system, cone cells for daylight vision and rod cells for twilight vision. In the optic nerves and visual pathways, there are several different types of nerve fibers, of which the magnocellular pathway 324 and the parvocellular pathway 328 are the most important. The magnocellular pathway 324 is considered by those skilled in the art to be the "where?" pathway; the parvocellular pathway 328 is considered by those skilled in the art to be the "what?" pathway. Further, the magnocellular pathway 324 carries all transient, motion related visual information and low contrast black and white information. The parvocellular pathway 328 carries all color information and is effective in carrying high contrast black and white information. Further, the human brain 322 includes a striate and peri-striate visual areas 326, which are well known in the art.

Figure 7:
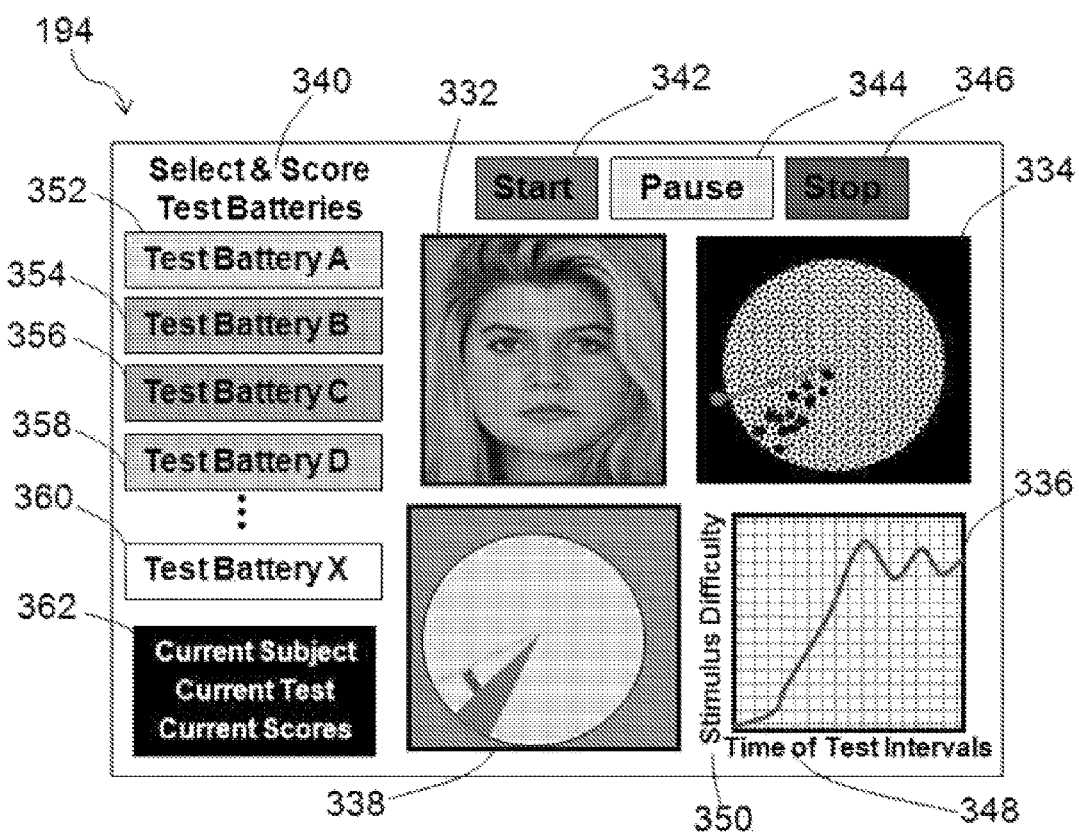
FIG. 7 display an exemplary operator display.

FIG. 7 display an exemplary operator display 194, which an operator 190 may utilize to evaluate functional impairment in the human brain 322 of a subject 192. The operator display 194 may include, but is not limited to, a real-time subject video display 332, a stimulus display 334, a current test performance display 336, and a subject error display 338. Further, the operator display 194 may display the current status 362, which may include, but is not limited to, the current status of the current subject, the current status of the current test, and the current status of the current scores. Further, the test performance display 336 may show a graph of stimulus difficulty 350 versus the time of time intervals 348.

The operator 190 may chose the appropriate test from test batteries 310 via the option of select and store test batteries 340. The operator display 194 enables the operator 190 to utilize the features of start 342, pause 344, and stop 346 with respect to any functional assessment test. Further, an operator 190 may chose a test from among the test batteries 310. For instance, the operator 190 may chose a functional assessment test that may be symbolized as test battery A 352, test battery B 354, test battery C 356, test battery D 358, or test battery X 360, as in shown on the exemplary operator display 194 of FIG. 7.

Further, the operator display 194 may be used to start and stop testing via a series of windows that may be shown by the use of the computing system 200. The series of windows may include the following:

i) A window for data entry regarding the subject 192, operator 190, and test site.

ii) A window for the operator 190 being able to view the subject's stimulus for monitoring.

iii) A window for the display of the current subject 192 and ongoing test.

iv) A window for the real-time display of graphical subject error and numerical subject error.

v) A window for the display of the subject's video image to the operator 190 for the monitoring of the subject's position and gaze.

vi) A window for the display of the subject's response saliency function.

vii) A window for the display of the subject's current basic scores.

viii) A window for the operator 190 to enter comments.

ix) A window for the operator 190 to enter identifying, medical history, treatment, etc.

Figure 8:
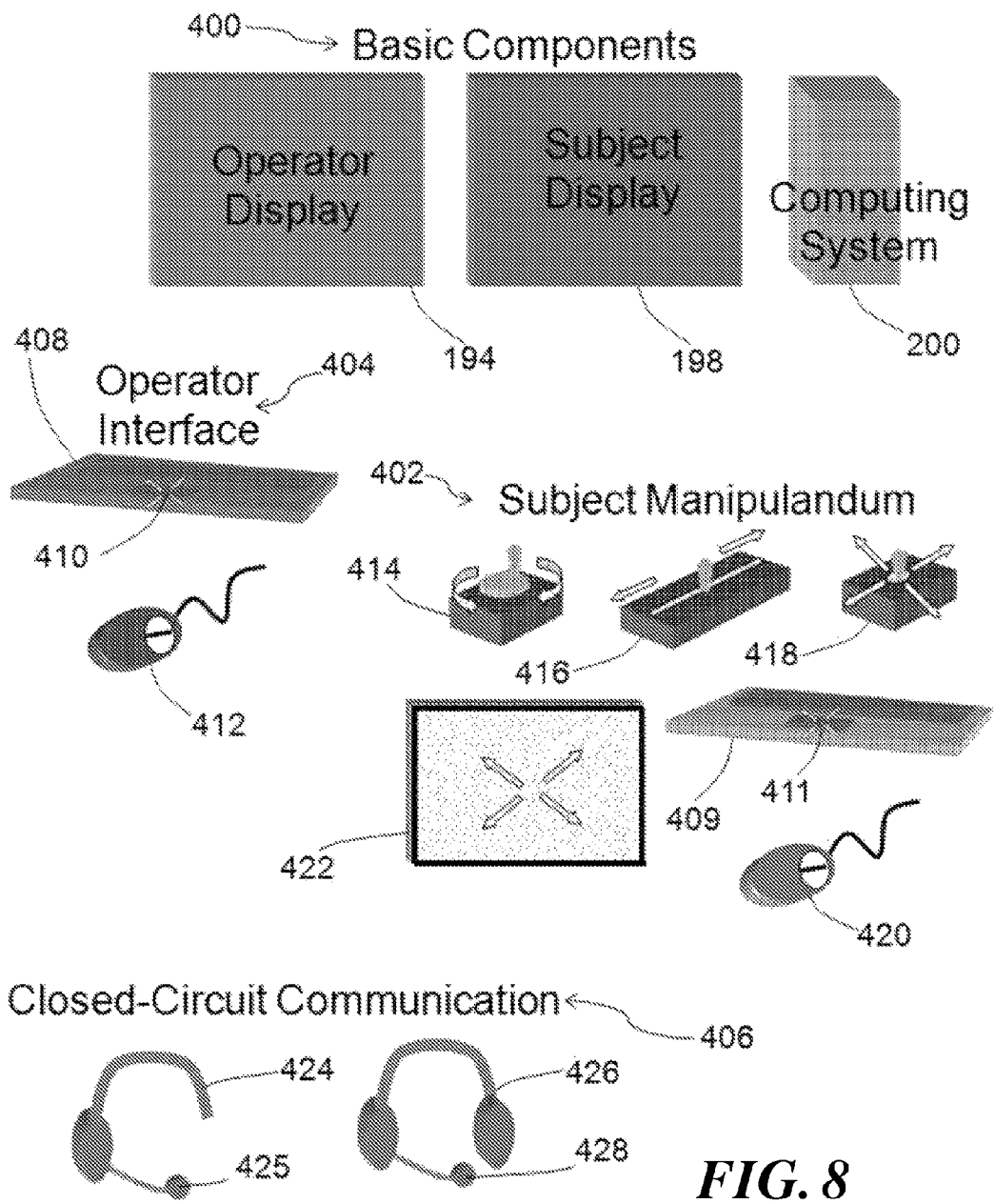
FIG. 8 illustrates an embodiment of the principal components of the presently disclosed method for assessment of functional impairment.

The operator display 194 may be one component, of many components, that may be utilized for quantitative assessment of functional impairment. FIG. 8 illustrates an embodiment of the principal components of the presently disclosed method for assessment of functional impairment. The principal components may include, but are not limited to, basic components 400, a subject manipulandum 402, an operator interface 404, and closed-circuit communication 406. The basic components 400 may be utilized in the test environment 188, as is shown in FIG. 3.

The operator interface 404, may include, but is not limited to devices specifically for use by the operator 190, such as a keyboard 244, herein called operator keyboard 408, and a pointing device 246, which may be, but is not limited to, an operator touchpad 410 or a mouse, herein called an operator mouse 412. A operator 190 may enter commands and information into the computing system 200 through input devices such as an operator touchpad 410 or an operator mouse 412. The operator 190 may utilize the operator interface 404 for entering identifying information, medical history, treatment data, etc. to facilitate in quantitative assessment of functional impairment.

Further, the closed-circuit communication 406 may include, but is not limited to, an operator headset 424, which may be utilized by the operator 190, and a subject headset 426, which may be utilized by the subject 192. The present disclosure may include a closed-circuit auditory link 406 between the subject 192 and the operator 190 that consists of three components:

i) The subject 192 may utilize a subject headset 426 to shield from audible distractors, thereby allowing for the controlled presentation of auditory stimuli as task cues or distractors, or cue elements of the task, which include, but are not limited to, specific tones and words, or for instructions or for coaching by the operator 190. The subject headset 426 may include a co-mounted subject microphone 428, which may always be on to the operator 190, thereby allowing all comments by the subject 192 and eliciting appropriate responses.

ii) The operator 190 may wear an operator headset 424 that may allow the operator 190 to hear any sounds from the subject 192 but also may allow the operator 190 to hear sounds from the surrounding environment. The operator headset 424 may include a co-mounted operator microphone 425, which may allow the operator 190 to speak with the subject 192. Further, the operator interface 404 may allow for contact with the subject 192 via the operator 190 being able to enable or disable a virtual switch in the operator display 194.

iii) The present disclosure includes software, hardware, and interface connections for controlling the state of the subject-operator closed-circuit communication 406.

Further principal components of the presently disclosed method for assessment of functional impairment may include a subject manipulandum 402, which may be a physical interfacing device that transforms input from a user. The properties of the subject manipulandum 402 may be akin to the properties of a pointing device 246 or other input devices, which may include, but is not limited to a wheel, a joystick, or a computer mouse device. Further, the subject manipulandum 402 may be a touch screen display panel 422 that can accommodate finger or stylus input, such as by text.

Similar to the operator interface 404, the subject manipulandum 402 may include, but is not limited to devices, such as a keyboard 244, herein called subject keyboard 409, and a pointing device 246, which may be, but is not limited to, a subject touchpad 411 or a mouse, herein called an subject mouse 420. A subject 192 may enter commands and information into the computing system 200 through input devices such as an operator touchpad 411 or an operator mouse 420.

Further, the subject 192 may respond exclusively by moving the positional control of the subject manipulandum 402, which is chosen to meet the design of the test. The subject manipulandum 402 may be manipulated by the hand of the subject 192, and its purpose is to maximize stimulus response compatibility so that sensory processing motor control aspects are not obscured. The subject 192 may provide input and respond to sensory stimuli by movement of the subject manipulandum 402 via one of the following options: a rotary manipulandum 414, a linear manipulandum 416, or a xy Cartesian manipulandum 418. Thus, the subject manipulandum 402 may move in rotation motion 440, a linear motion 442, x-axis motion in the Cartesian coordinate system 444, or y-axis motion in the Cartesian coordinate system 446. In addition, the movement of the subject manipulandum 402 may be represented as a cursor 1050 on the subject display 198. The cursor may be, but is not limited to, a ball-and-stick cursor.

Figure 9:
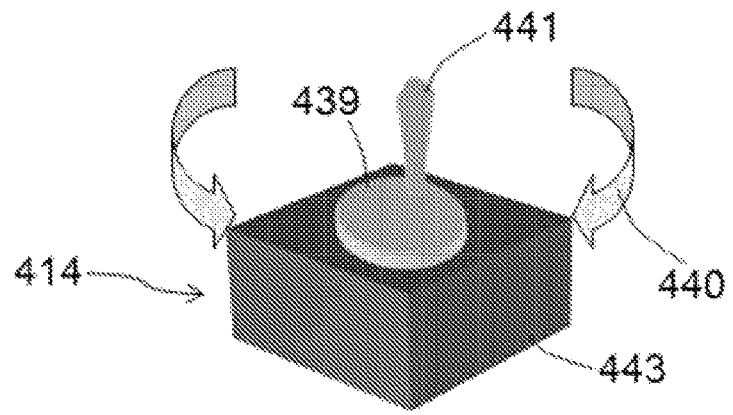
FIG. 9 shows a rotary manipulandum device that may support the presently disclosed method for assessment of functional impairment.
Figure 10:
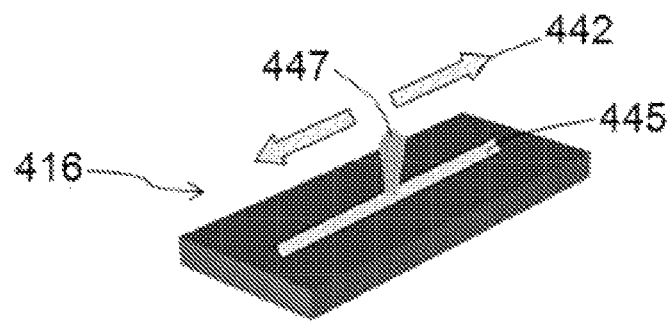
FIG. 10 presents a linear manipulandum device that may support the presently disclosed method for assessment of functional impairment.
Figure 11:
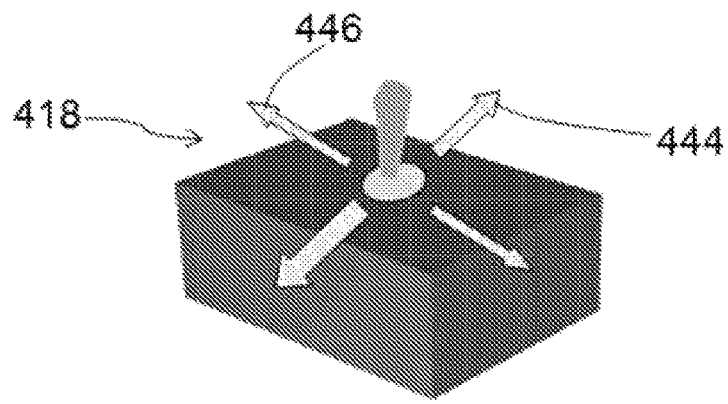
FIG. 11 shows a xy Catersian manipulandum that may support the presently disclosed method for assessment of functional impairment.

With reference to FIGS. 9, 10, and 11, an exemplary a rotary manipulandum 414, an exemplary linear manipulandum 416, and an exemplary xy Cartesian manipulandum 418 are shown in greater detail.

Further, the subject manipulandum 402 may be designed to incorporate a means of monitoring whether the subject 192 is contacting a handle through a capacitive contact detector. Further, the subject manipulandum 402 may be designed to incorporate a motorized system that can alter the resistance offered by the subject manipulandum 402 to the subject 192 by moving it for use in testing the motoric control of the subject 192. Further, the subject manipulandum 402 may be designed to incorporate a vibrating element that can create a variable amplitude, variable frequency vibration of a handle as a cue or a distracting stimulus.

Further, the present disclosure may accommodate the use of a plurality of subject manipulandum 402 to test the motoric control of the subject 192. The present disclosure may accommodate two manibulandum 402, one with each of the subject's hands.

Further, the response of the subject manipulandum 402 may be implemented as separate box mounted devices or virtual devices on a touch screen display panel 422 that can accommodate finger or stylus input, such as by text.

Further the present disclosure may include a principal component of a computing system 200, which may include a computer readable medium or may include a computing process, that supports detailed operations by interfacing with other hardware components and by representative software described in the further in the present disclosure.

More particularly, the subject manipulandum 402 may be a rotary manipulandum 414 that moves in a rotational motion 440, as is shown in FIG. 9. The rotary manipulandum 414 may consists of a box mounted wheel 439, which may be mounted such that it can rotate around its center, which may be attached to a rotation circuit in the box 443. The box mounted wheel 439 is moved by grasping an eccentric handle 441 that the subject 192 uses to rotate the angle of the rotary manipulandum 414, which may be a displayed as a cursor 1050 on the subject display 198. The motion of the rotary manipulandum 414 may be from zero to three-hundred sixty angular degrees, which may be translated with as representative motion, also from zero to three-hundred sixty angular degrees, in the form of a cursor 1050 on the subject display 198.

FIG. 10 presents a linear manipulandum 416 that moves in a linear motion 442. The linear manipulandum 416 may consist of a box-mounted slot 445 from which a handle 447 protrudes. The handle 447 is attached to circuit in the box 443 that transduces the movement of the handle 447 across the extent of the slot 445. The handle 447 is grasped by the subject 192 and moved along the axis of the slot 445, which may move the cursor 1050 on the subject display 198. The movement of the cursor 1050 may be represented as a displayed linear cursor on the subject display 198. The displayed linear form of the cursor 1050 may move in a variety of means, including, but not limited to, a side-to-side motion or an up-and down motion, across a corresponding axis of the stimulus area 199.

FIG. 11 shows a xy Catersian manipulandum 418 that moves in the Cartesian coordinate system, which may be x-axis motion in the Cartesian coordinate system 444 or y-axis motion in the Cartesian coordinate system 446. The xy Catersian manipulandum 418 may consist of a box mounted handle 449 that is attached to a xy Cartesian coordinate transducer circuit that registers the position of the handle's angular deflection. The box mounted handle 449 is tilted by the subject 192 to displace a cursor 1050 across the xy surface of the subject display 198; the xy surface of the subject display 198 may be shown from the upper left to the lower right of the subject display 198.

Figure 12:
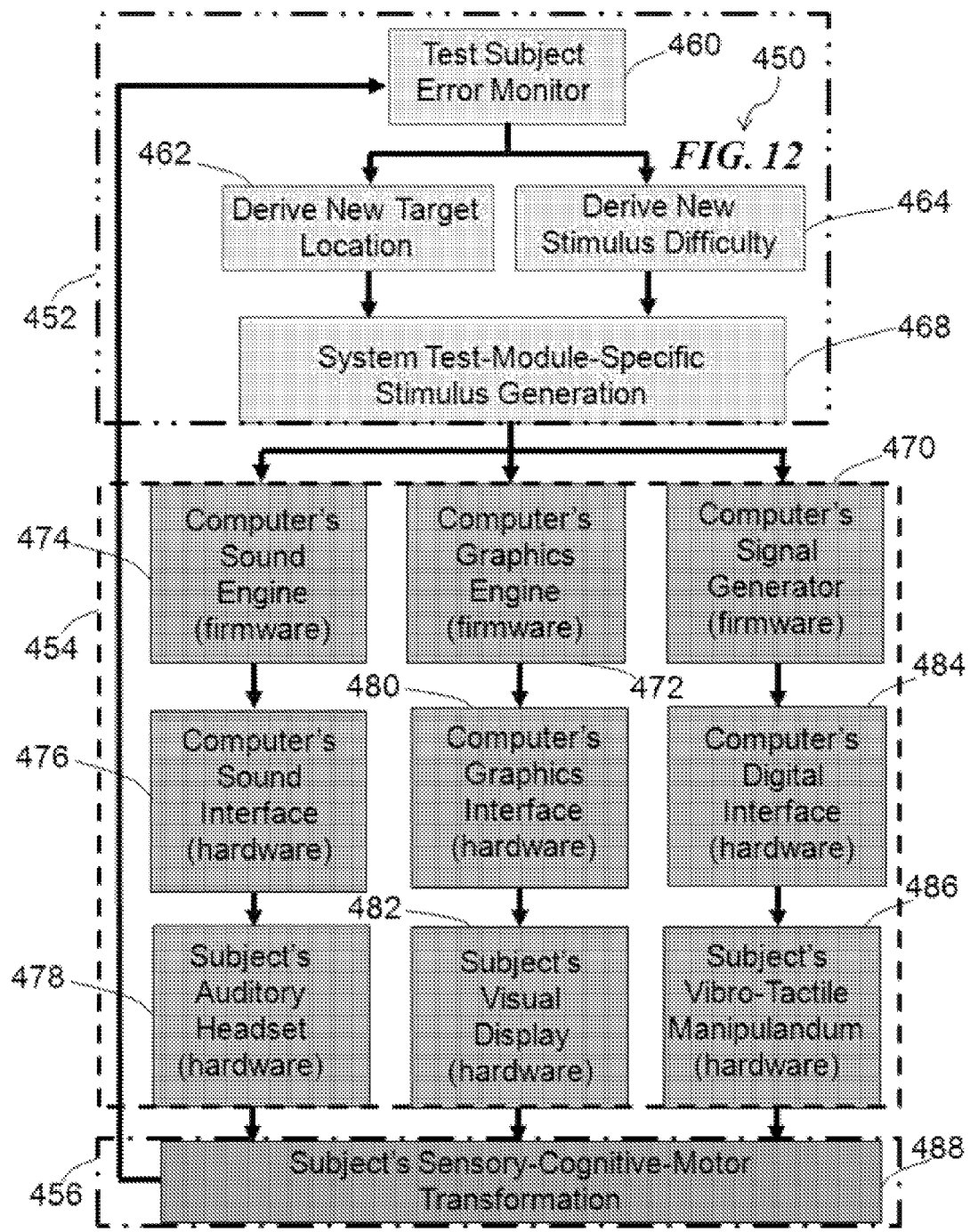
FIG. 12 portrays a block diagram of a stimulus generator that combines hardware and software to produce a scene parameter.

FIG. 12 portrays a block diagram of a stimulus generator 450, which may further comprise the system software 452, the application hardware configuration 454, and the system conceptualization of neural processing 456. Further, the block diagram of a stimulus generator 450 may combine hardware and software to produce a scene parameter.

The system software 452 may consider the test subject error monitor 460 towards both the steps of derive new target location 462 and derive new stimulus difficulty 464. The results of the steps of derive new target location 462 and derive new stimulus difficulty 464 may influence the step of system test-module-specific stimulus generation 468.

Further, the steps involved in the system software 452 may influence the steps involved in the application hardware configuration 454. More particularly, the results of the step of system test-module-specific stimulus generation 468 may be applicable towards each of the steps that are associated with the computer's sound's engine (firmware) 474, the computer's graphics engine (firmware) 472, and the computer's signal generator (firmware) 470.

The results of the step associated with the computer's sound's engine (firmware) 474 may be applicable towards the step associated with computer's sound interface (hardware) 476. The results of the step associated with the computer's graphics engine (firmware) 472 may be applicable towards the step associated with computer's graphics interface (hardware) 480. The results of the step associated with the computer's signal generator (firmware) 470 may be applicable towards the step associated with the computer's digital interface (hardware) 484.

Further, the results of the step associated with the computer's sound interface (hardware) 476 may be applicable towards the step associated with the subject's auditory headset (hardware) 478. The results of the step associated with the computer's graphics interface (hardware) 480 may be applicable towards the step associated with the subject's visual display (hardware) 482. The results of the step associated with the computer's digital interface (hardware) 484 may be applicable towards the step associated with the subject's vibro-tactile manipulandum (hardware) 486.

Further, the steps involved in the application hardware configuration 454 may influence the steps involved in the step of system test-module-specific stimulus generation 468. More particularly, the steps associated with either of the subject's auditory headset (hardware) 478, the subject's visual display (hardware) 482, or the subject's vibro-tactile manipulandum (hardware) 486 may be associated with the step of system test-module-specific stimulus generation 468.

Figure 13:
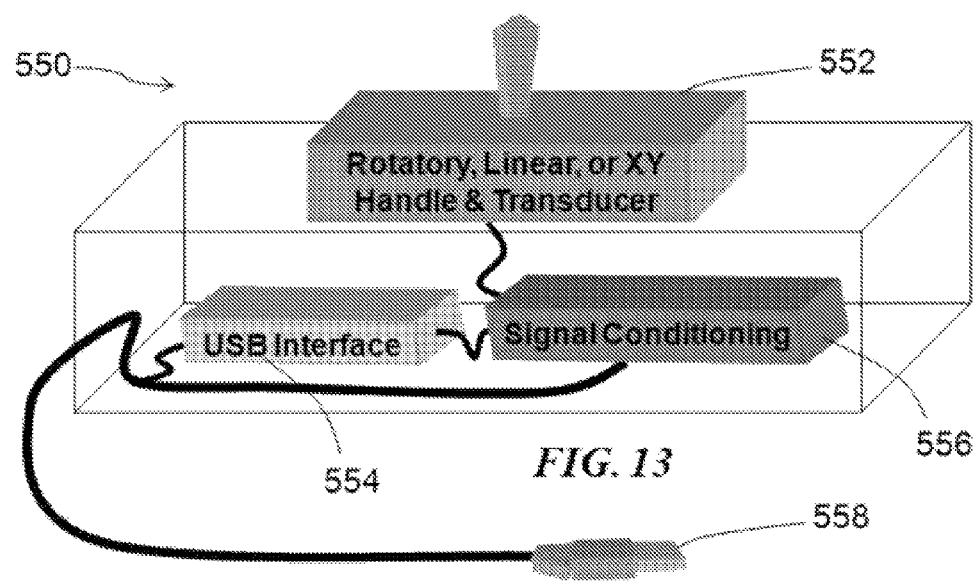
FIG. 13 shows a block diagram of the subject manipulandums that may support the presently disclosed method for assessment of functional impairment.

FIG. 13 shows a block diagram of the subject manipulandums 550, which represents the necessary components associated with the subject manipulandums 402. The components a of the block diagram of the subject manipulandums 550 may include, but is not limited to, the manipulandum handle and transducer 552, a USB interface 554, signal conditioning 556, and the USB connector to system computer 558. Further, the manipulandum handle and transducer 552 may be associated with either of the rotary manipulandum 414, linear manipulandum 416, or xy Cartesian manipulandum 418.

The output associated with the manipulandum handle and transducer 552 is coupled to the signal conditioning 556, which may either be applicable towards the USB interface or directly with the USB connector to system computer 558. The output associated with the USB interface is directly coupled to the USB connector to system computer 558.

Figure 14:
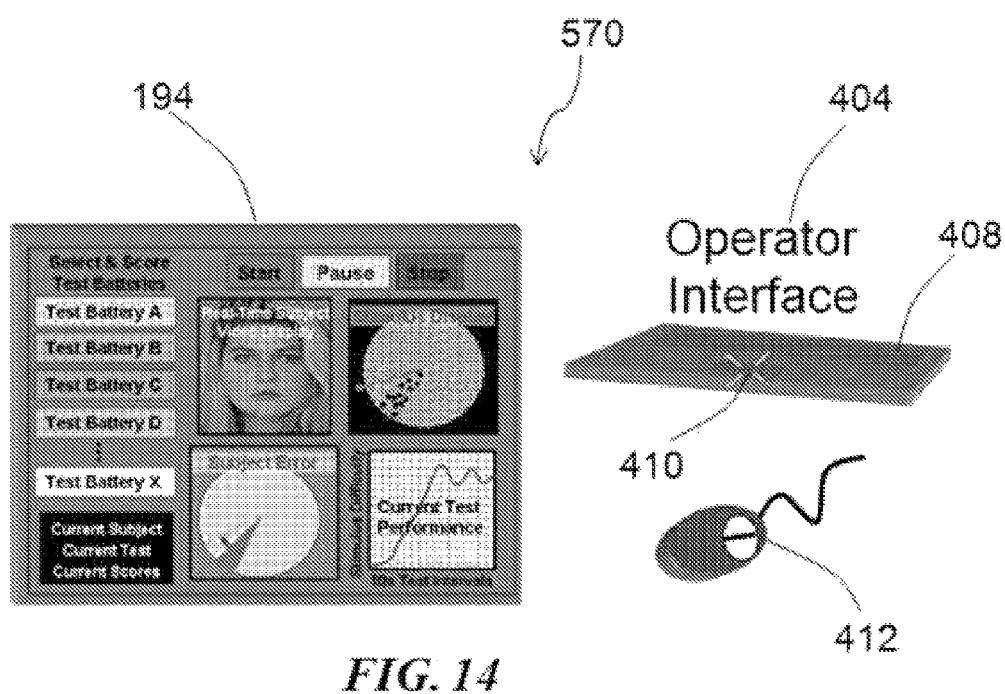
FIG. 14 portrays an exemplary operator output interface.

FIG. 14 portrays an exemplary operator output interface 570, which may include, but is not limited to, an operator display 194 and an operator interface 404. The operator display 194 is shown in greater detail in FIG. 7 and its accompanying description. The operator interface 404 is shown in greater detail in FIG. 8 and its accompanying description. Further, the operator display 194 may include an exemplary real-time subject video display 332 for presenting tests of a series of scenes for use with the presently disclosed subject matter.

Figure 15:
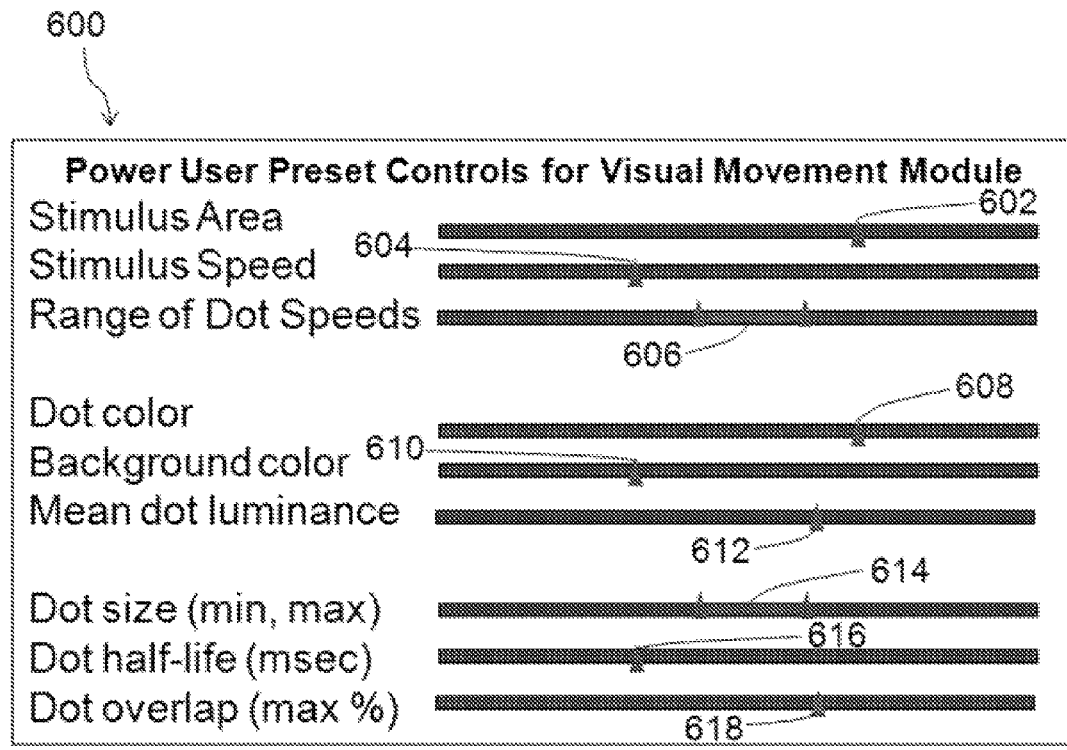
FIG. 15 depicts a power user preset controls for visual movement module, which may serve as a graphical user interface with parameter adjustment sliders and buttons in the operator display.

FIG. 15 depicts a sub-component of the operator display 194, the power user preset controls for visual movement module 600, which may serve as a graphical user interface with parameter adjustment sliders and buttons. The operator 190 may control the power user preset controls for visual movement module 600 in order to make changes to one, several, or all of the settings associated with the movement test 302. The power user preset controls for visual movement module 600 may include, but is not limited to, slider bars, with accompanying value ranges for the stimulus area 602, the stimulus speed 604, the range of dot speeds 606, the dot color 608, the background color 610, the mean dot luminance 612, the dot size (min, max) 614, the dot half-life (msec) 616, and the dot overlap (max %) 618.

Figure 16:
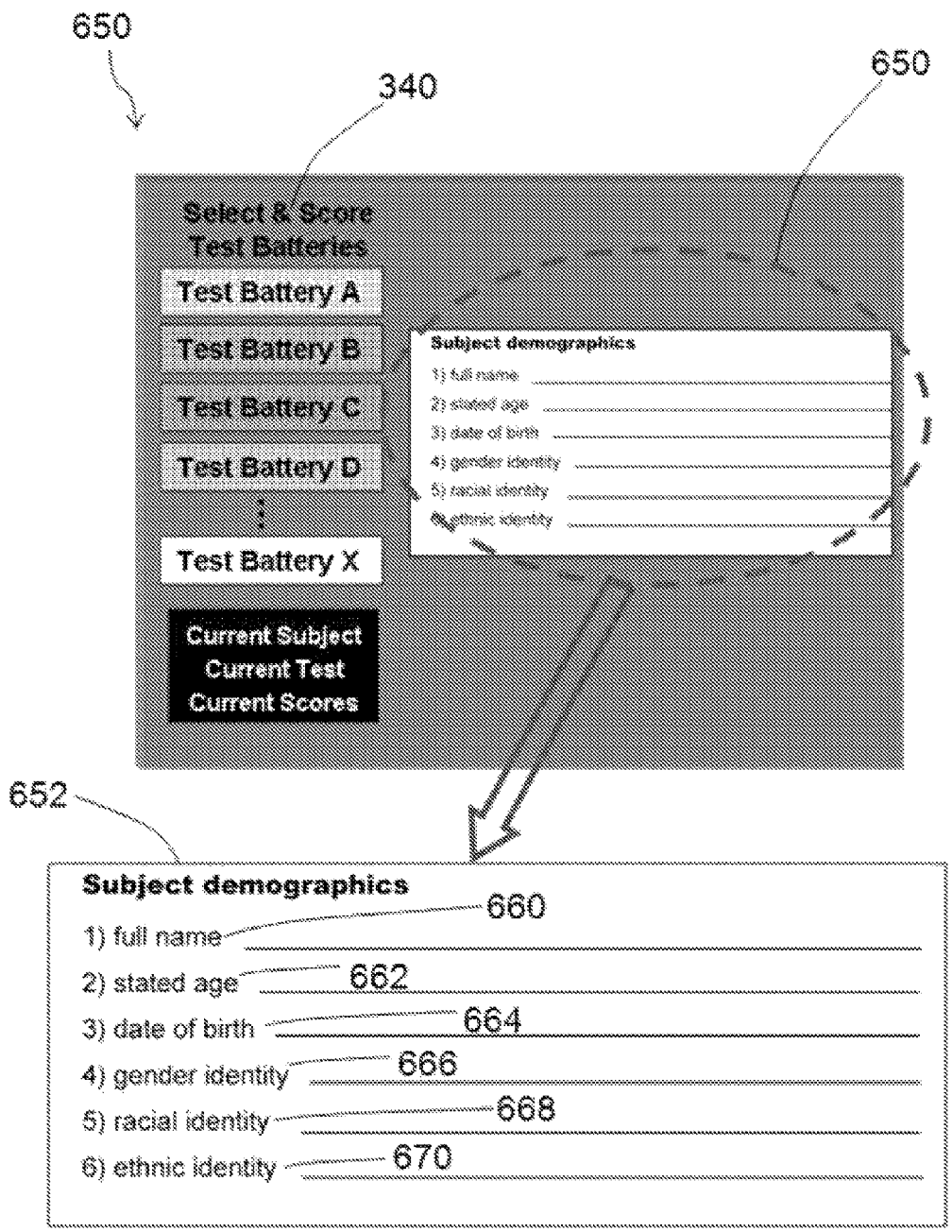
FIG. 16 presents a graphical user interface for a subject demographics entry display.

FIG. 16 presents a window in the operator display 194, which in addition to the option of select and score test batteries 340, may also include an exemplary subject demographics entry display 650. The operator 190 may enter subject demographics 652 for the subject 192 in the subject demographics entry display 650, which may be a sub-component of the operator display 194. The subject demographics may include, but are not limited to, the full name 660, the stated age 662, the date of birth 664, the gender identity 666, the racial identity 668, and the ethnic identity 670.

Figure 17:
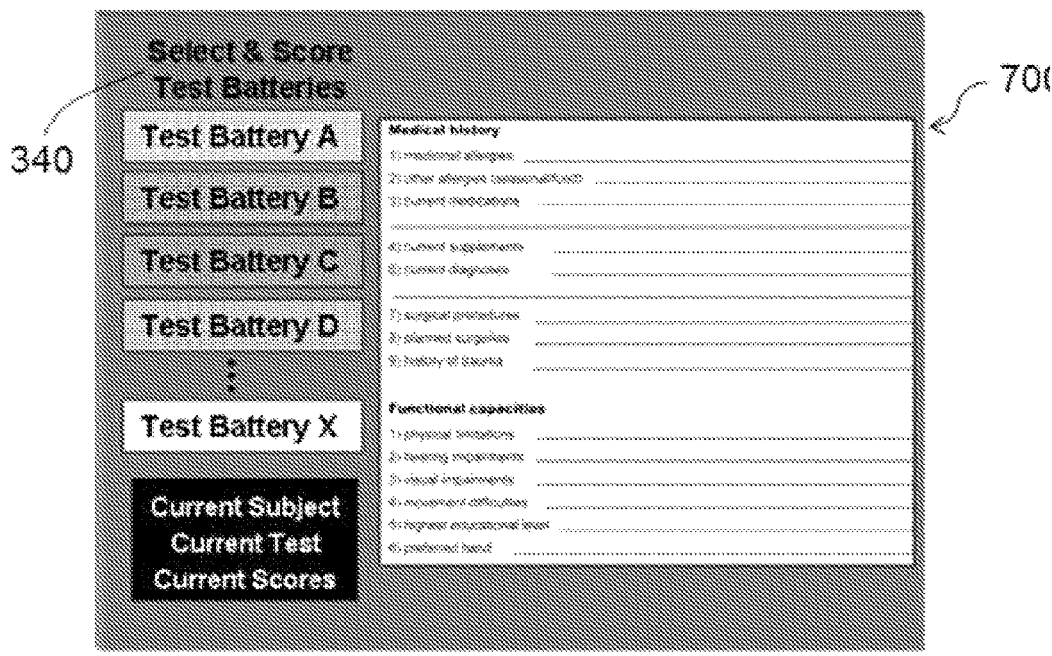
FIG. 17 shows an exemplary subject medical history entry display.

FIG. 17 shows a window in the operator display 194, which in addition to the option of select and score test batteries 340, may also include an exemplary subject medical history entry display 700. The operator 190 may enter the medical history 710 and the functional capacities 712 for the subject 192 in the subject medical history entry display 700, which may be a sub-component of the operator display 194. Further the medical history 710 may include, but is not limited to, medicinal allergies 720, other allergies (seasonal/food) 722, current medications 724, current supplements 726, current diagnoses 728, surgical procedures 730, planned surgeries 732, and history of trauma 734. Further the functional capacities 712 may include, but is not limited to, physical limitations 736, hearing impairments 738, visual impairments 740, movement difficulties 742, highest educational level 744, and preferred hand 746. The medical history 710 and the functional capacities 712 may contribute towards the quantitative assessment of functional impairment, and thereby may contribute towards the treatment for the subject 192.

Figure 18:
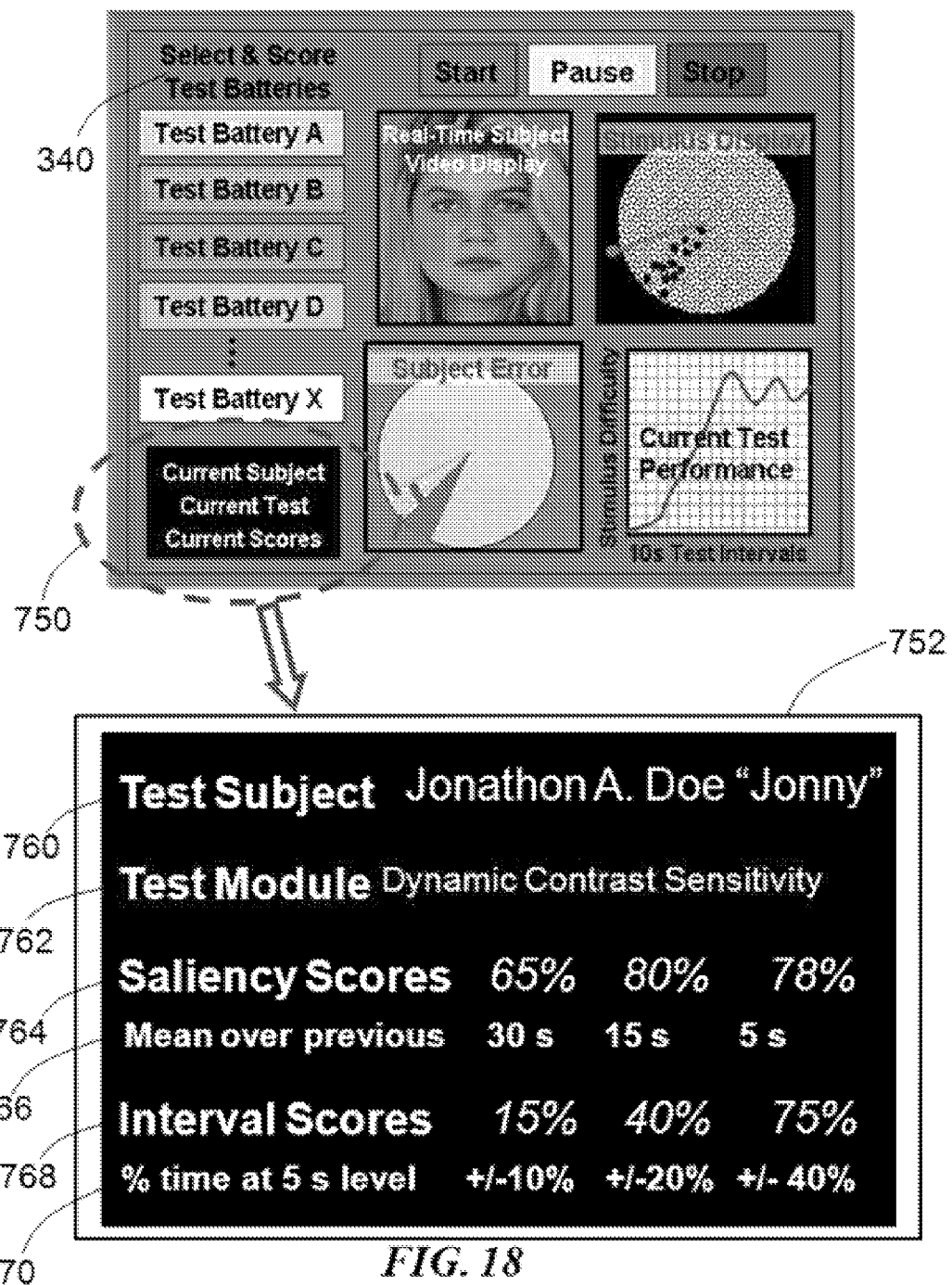
FIG. 18 illustrates an exemplary standard operations test scoring display.

FIG. 18 shows a standard operations test scoring display 750, which may be a window in the graphical user interface for the display of the subject's current basic scores. The standard operations test scoring display 750 may be a display in addition to the option of select and score test batteries 340, which may be a part of the operator display 194.

The standard operations test scoring display 750 may further display a more detailed test scoring display 752, which may include, but is not limited to, the test subject output 760, the test module output 762, the saliency scores output 764, the mean over previous output 766, the interval scores output 768, and the percentage time at five seconds level output 770. Further, the test scoring display 752 may show current data associated with a current, particular test that may be for quantitative assessment of functional impairment.

Further, the mean over previous output 766 may be associated with the saliency scores output 764. Further, the percentage time at five seconds level output 770 may be associated with the interval scores output 768.

Figure 19:
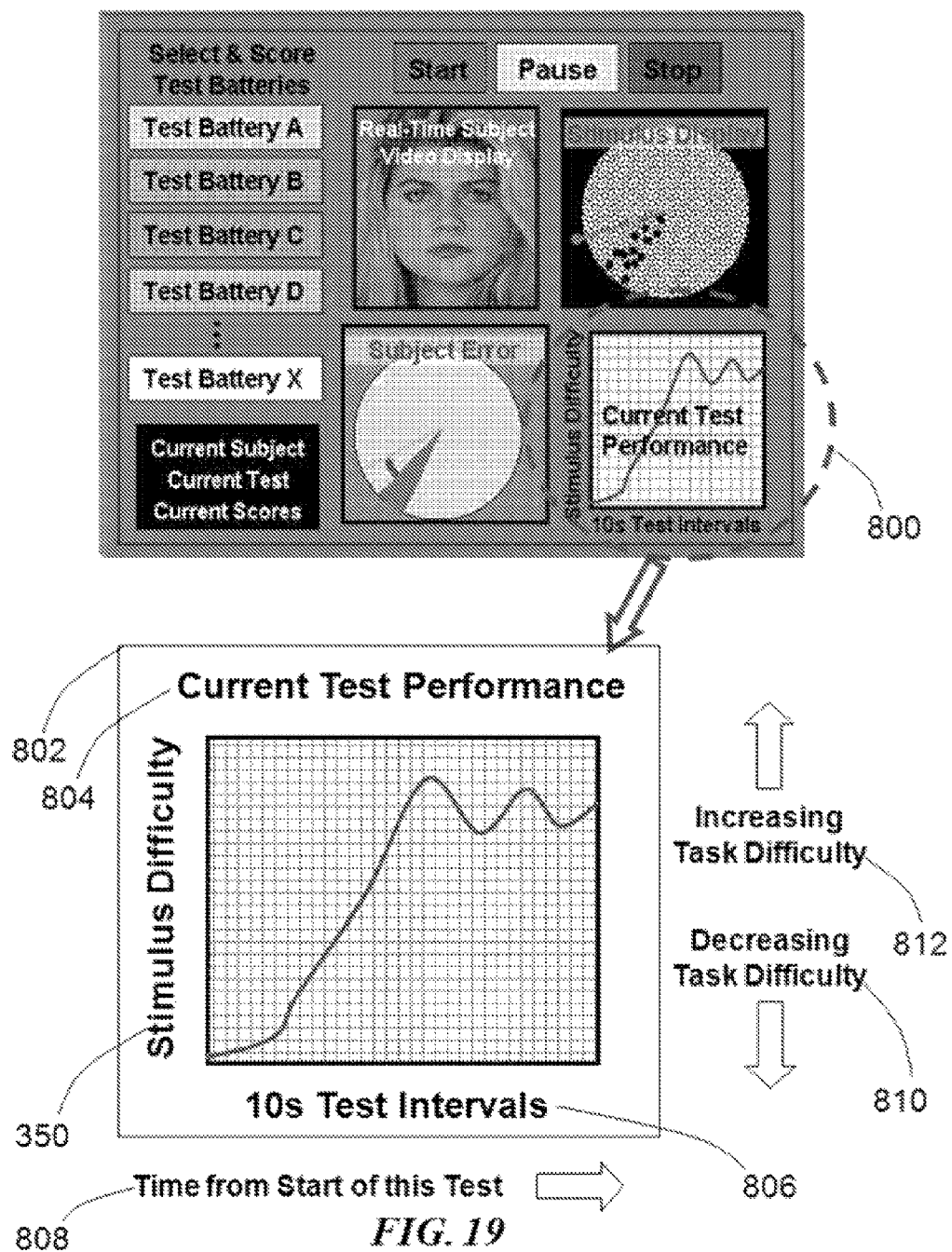
FIG. 19 shows an exemplary standard operations dynamic performance display.

FIG. 19 shows a window in the operator display 194, which in addition to the option of select and score test batteries 340, may also include an exemplary standard operations dynamic performance display 800. The current test performance 802, which may be represented graphically as the graph of current of current test performance 804, which may be a graph of stimulus difficulty 350 versus ten seconds intervals 806.

Further, the ten seconds intervals 806 is an exemplary representation of the time from the start of this test 808. However, different time intervals may be represented on as the time from the start of this test 808 on the graph of current of current test performance 804.

Further, the graph of current of current test performance 804 may represent increasing task difficulty 812 with a higher value of stimulus difficulty 350. Further, the graph of current of current test performance 804 may represent decreasing task difficulty 810 with a lower value of stimulus difficulty 350.

Further, the current test performance 802 may be a more detailed representation of the standard operations dynamic performance display 800. Further, the current test performance 802 may be associated with the subject's response saliency function.

Figure 20:
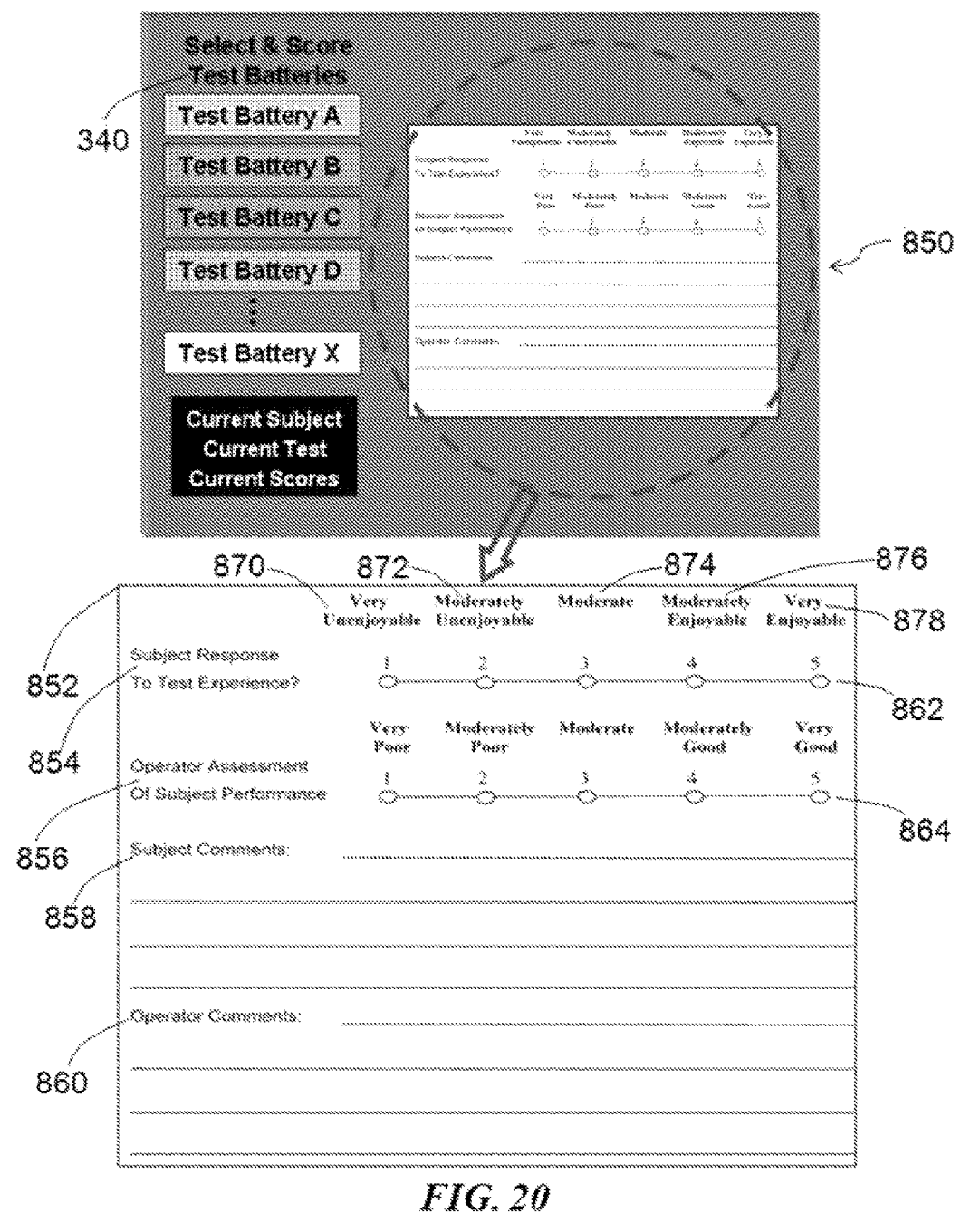

FIG. 20 shows a window in the operator display 194, which in addition to the option of select and score test batteries 340, may also include an exemplary operator comments entry display 850. The operator 190 may enter comments on the operator comments entry 852, which may be a sub-component of the operator comments entry display 850. The operator comments entry 852 may include, but is not limited to, prompts for subject response to test experience 854, operator assessment of subject performance 856, subject comments 858, and operator comments 860.

Further, the subject response to test experience 854 may be scored on a scale of subject response to test performance 862, which may be scored, but is not limited to being scored, from very unenjoyable 870 to moderately unenjoyabled 872 to moderate 874 to moderately unenjoyable 876 to very enjoyable 878. The operator assessment of subject performance 856 may be scored on a scale of operator assessment of subject performance 864, which may be scored, but is not limited to being scored, from very unenjoyable 870 to moderately unenjoyable 872 to moderate 874 to moderately unenjoyable 876 to very enjoyable 878.

Figure 21:
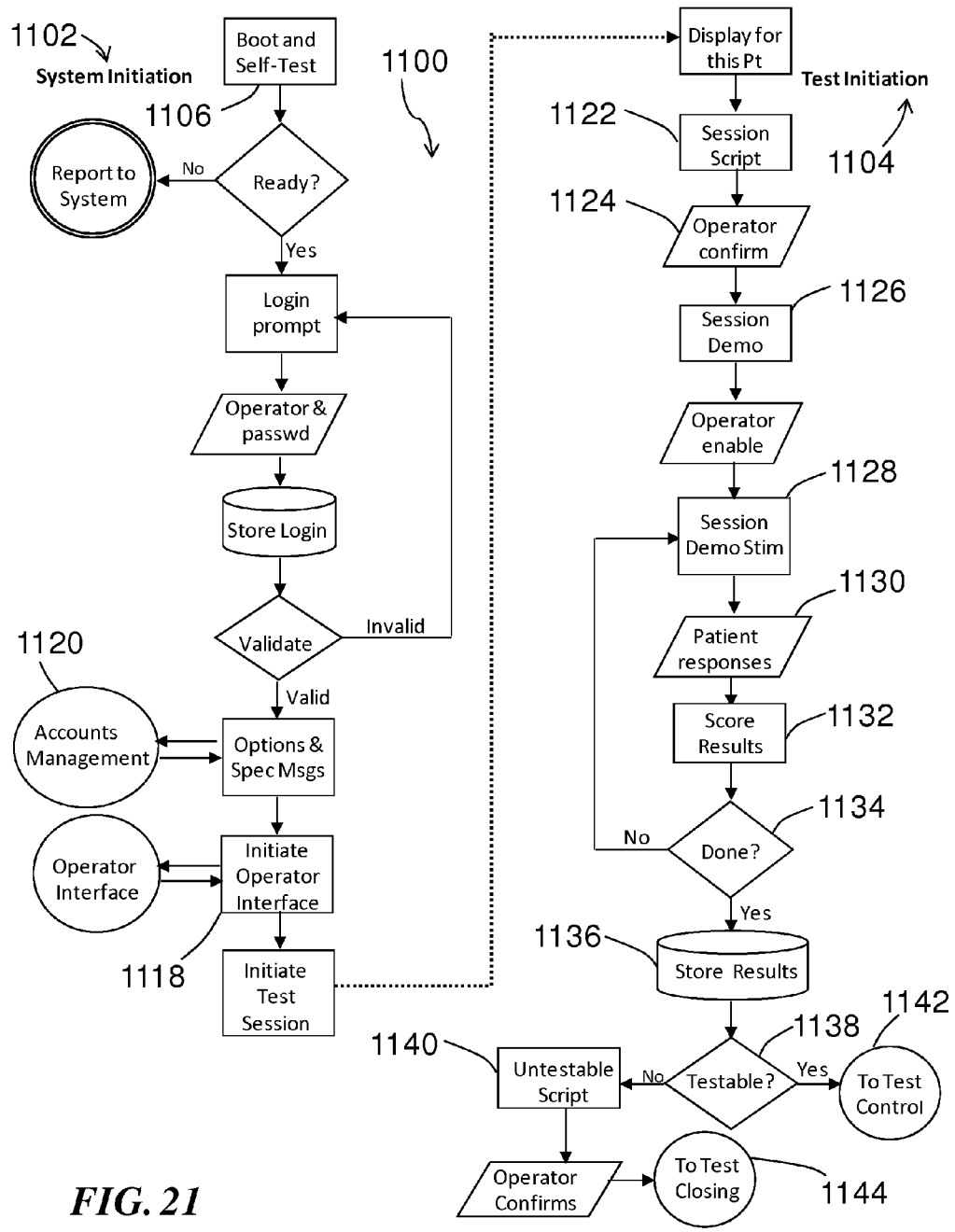
FIG. 21 presents the system initiation sequence and the test initiation sequence of the testing flow process for the conceptual framework for quantitative assessment.

With reference to FIG. 21 through FIG. 78, the present disclosure includes multiple levels of system configurability implemented with an extensive multi-dimensional parametric control system with a large number of parametric adjustment controls. These parameters allow for the flexible specialization of the present disclosure across many application domains as well as the flexible specialization of the present disclosure to specific medical diagnoses and corresponding issues related to the wide variety of directly foreseeable applications of this technology.

The present disclosure allows for specialization of parameters with regards to tests included for specific applications, which may included, but is not limited to the following:

i) The present disclosure allows for the selection of specific tests for specific applications, such as a test array emphasizes posterior cortical and sub-cortical function in applications regarding Alzheimer's Disease, and in contrast, a different test array in screening of frontal lobe and temporal lobe function in applications regarding the fronto-temporal dementias.

ii) The present disclosure may allow assessment of the underlying mechanisms for drug and toxin exposures. Specific applications for drug and toxin exposures may be selected by experience acquired from implementation of the present disclosure.

iii) The intrinsic configurability that is fundamental to the present disclosure also allows for implementing a broad-based, non-specialized screening array when such an array best serves specific applications.

iv) The present disclosure may include a power-user test array configuration mode in which a specific sub-set of tests from the present disclosure may be included or excluded as best suited to the specific interests of the customer or for specific applications.

v) As a result of the intrinsic configurability, the total duration of testing as described in the present disclosure may vary widely across applications.

Further, the present disclosure may provide for a complete, streamline workflow of experimental design, display calibration, data collection, and data analysis for the quantitative assessment of functional impairment. The experiment is the root event that specifies the parameters that may be implemented during the experiment.

Specialization of parameters for test configuration to be used in specific applications may include, but is not limited to, the following:

i) The present disclosure may allow for the selection of all physical parameters of all the tests described in the present disclosure. Such parametric configuration includes altering the speed of target motion, the rate of target saliency increase or decrease, spatial and temporal frequency composition of the stimuli and the nature of multi-modal stimuli, such as visual stimuli alone, auditory stimuli alone, hand-finger vibratory tactile stimuli alone, or any combination of those modalities as cues or distractors.

ii) The present disclosure's parametric adjustment setting may include all aspects of the visual display, including, but not limited to, luminance, contrast, spatial and temporal frequency composition, target movement, all aspects of the test subject's motor control medium, including but not limited to, adjusting response sensitivity, filtering subject response signal frequency, and all aspects of auditory input to the subject, including, but not limited to, visual and/or auditory presentation of instructions, visual and/or auditory presentation of test stimuli, such as words or tones, the presentation of auditory stimuli as distractors, and the amplitude and filtering of auditory stimuli.

iii) The present disclosure may include parametric adjustment due to qualitative assessment. Such parametric adjustment, such as the ability to select parameters that are derived from demographic specification of the individual, which may include, but is not limited to, age, gender, medical history, drug treatments, or from the results of specific tests in a testing array sequence, which may include, but is not limited to, using a contrast sensitivity profile to alter the contrast at which all other visual stimuli will be presented, or using the speed and other subject movement parameters to alter the target movement parameters for all other tests. These subject performance dependent meta-parameters may be used as directly derived from that subject's or subject group's performance or may be algorithmically programmed.

iv) The present disclosure may include a power-user test parametric configuration mode in which computerized parameter adjustment sliders and buttons may be presented to allow for the adjustment of parameters as best suited to the specific interests of the customer or for specific applications.

Further, specialization of the testing configuration for applications to testing specific subjects may allow for the selection of a language in which instructions and linguistic cues that may be presented for testing subjects native to other languages.

Further, specialization of the testing configuration for applications to testing specific subject may allow for the selection of relevant cues such as geometric shapes or tones or such as objects and recognizable sounds rather than language cues in applications for age-appropriate, developmental, or acquired impairments of language processing.

Further, specialization of testing configuration for applications to testing specific subject may allow for using an individual subject's scores from a previous testing session, at that site or another test site. Further, specialization of testing configuration for applications to testing specific subject may allow for using an individual subject's scores to select the test to be administered, which may potentially focus on abnormal or unreliable performance or on application specific selected performance. Likewise, test configuration parameters may be inherited from previous testing sessions to match those tests or to extend testing in to a different parametric domain.

Further, specialization of the testing configuration for applications to testing specific subject may allow for operator entered alerts on areas of concern, which may be in response to subject complaints alerting the physician or operator regarding some function, such as memory.

The present disclosure may include the extensive processing of subject performance data integrated with information from sources that may include: i) subject demographics, such as from scores standardized to normal for age or education, ii) subject characteristics from an established diagnosis or know treatment that may alter or focus analysis, such as with motor response in Parkinsonism, or iii) previous test scores, such as to focus on measuring improvement, stability or decline.

The present disclosure may include on-line data analysis, which may include the presentation and archiving of summary scores at the termination of the administration of each test. The scores from these tests may include: the mean saliency, as percent of maximum score, in last fifteen, ten, and five seconds of a test, the saliency at which the greatest percentage of time was spent in a test, the saliency at which the subject first lost track of the target. In another embodiment, the present disclosure may generate real-time score during the administration of each test.

The present disclosure may include off-line data analysis, which may include the derivation of a variety of dependent measures, including, but not limited to: i) the subject's response curve fit parameters to an asymptotic function, the salience level of that asymptote, and the time it takes to achieve that asymptote, ii) the area under the curve of the subject's response function, terminated by either a preset time, such as one-hundred seconds of testing or thirty seconds after the asymptote is reached, or the time to three peak/troughs in the response function or the time until a preselected cut-off is achieved, such as a saliency greater than ninety-five percentage, iii) comparative evaluations such as the differences between the measures of a subject's performance on a selected test versus that from another selected test, iv) comparative measures such as the differences between the basic measures of a subject on a test and the measures from a selected group of comparison subjects, such as the percentile scaled performance scores standardized for age, gender, and education.

More particularly, system initiation and test initiation, as applied to the quantitative assessment of functional impairment as described in the present disclosure, may be shown by way of illustration. FIG. 21 shows an embodiment of a testing flow process 1100 for the conceptual framework for quantitative assessment. At the start step of testing flow process 1100, the system initiation sequence 1102 may begin with the boot and self-test step 1106 and may proceed to initiate operator interface at step 1108. Upon receiving data entry input from the operator 190 via the operator interface 1120 during the initiate operator interface step 1108, the system initiation sequence 1102 may be completed.

The ensuing test initiation sequence 1104 may commence subsequently with the session script step 1122. Upon receiving operator confirmation 1124 the session demo 1126 begins with the session demo stimulus 1128. At step 1130 of patient responses, score results 1132 are recorded. Thereafter, done query 1134 may ascertain whether the session demo stimulus 128 has finished. If done query 1134 is no, then the test initiation sequence 1104 reverts back to the session demo stimulus 1128. If done query 1134 is yes, then the test initiation sequence 1104 proceeds with store results step 1136.

Thereafter, testable query 1138 may discern whether the store results are testable. If testable query 1138 is no, then the test initiation sequence 1104 determines a resulting untestable script 1140, and thereby proceeds step of to test closing step 1144. If testable query 1138 is yes, then the test initiation sequence 1104 proceeds with the to test control 1142, which is further depicted in FIG. 22 with more detailed steps.

Figure 22:
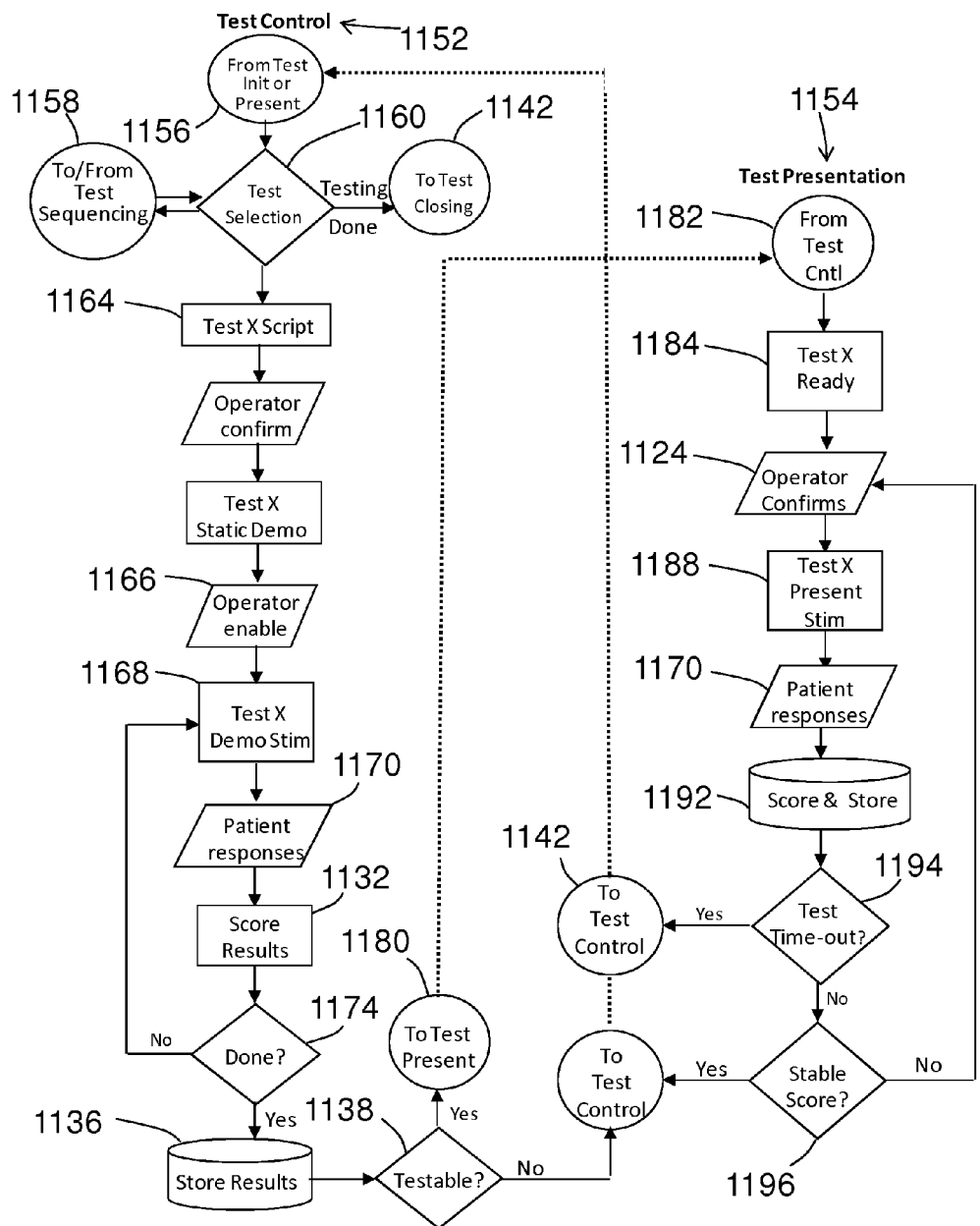
FIG. 22 illustrates a sequence of test control steps and a sequence of test presentation steps.

More particularly, test control and test presentation, as applied to the quantitative assessment of functional impairment as described in the present disclosure, may be shown by way of illustration. FIG. 22 displays a sequence of test control steps 1152 and a sequence of test presentation steps 1154. At the test control step 1142 indicated in FIG. 21, the test initiation sequence 1104 may progress into the sequence of test control steps 1152. Initially after the from test initiation or presentation step 1156, the sequence of test control steps 1152 proceeds to the query test selection 1160. Query test selection 1160 may search to allocate an appropriate test to/from test sequencing 1158. Upon achieving test selection 1160, the sequence of test control steps 1152 may proceed to test closing step 1142 under the assumption of no remaining tests. Further, upon achieving test selection 1160, the sequence of test control steps 1152 may proceed to the test script step 1164 under the assumption of remaining tests.

The operator enable step 1166 may promote the introduction of the test demo stimulus 1168. The sequence of test control steps 1152 may proceed with receiving input via patient responses 1170, for which the testing flow process 1100 records the score results 1132. If the sequence of test control steps 1152 does not complete score results 1132, then the sequence of test control steps 1152 continues with test demo stimulus 1168 in a control loop until the sequence of test control steps 1152 completes score results 1132.

Upon achieving score results 1132, the sequence of test control steps 1152 may proceed to the store results step 1136 and then to the testable query 1138. If testable query 1138 is yes, then the sequence of test control steps 1152 may proceed to step of to test presentation 1180 and initiates the sequence of test presentation steps 1154, starting with the step of from test control 1182. Then, at from test control step 1182, the sequence of test presentation steps 1154 may proceed with having a particular test x ready step 1184, followed by the step of operator confirmation 1124.

However, if testable query 1138 is no, then the sequence of test control steps 1152 may proceed to the step of to test control 1142. Afterward, the sequence of test control steps 1152 may revert back to the test initiation or presentation step 1156.

Upon receiving operator confirmation 1124, the sequence of test presentation steps 1154 may present a particular test x present stimulus step 1188, thereby promoting patient responses 1170. Subsequently, the patient responses 1170 may be recorded in the score and store step 1192, thereby prompting the test time-out query 1194. If test time-out query 1194 is no, then the sequence of test presentation steps 1154 proceeds to the query of stable score 1196.

However, if test time-out query 1194 is yes, then the sequence of test presentation steps 1154 may proceed to the step of to test control 1142, thereby reverting to the test initiation or presentation step 1156. If test time-out query 1194 is no, then the sequence of test presentation steps 1154 may present the stable score query 1196. If stable score query 1196 is no, then the sequence of test presentation steps 1154 may revert back to the step of operator confirmation 1124. However, if stable score query 1196 is yes, then the sequence of test presentation steps 1154 to the step of to test control 1142, may revert back to the test initiation or presentation step 1156.

Figure 23:
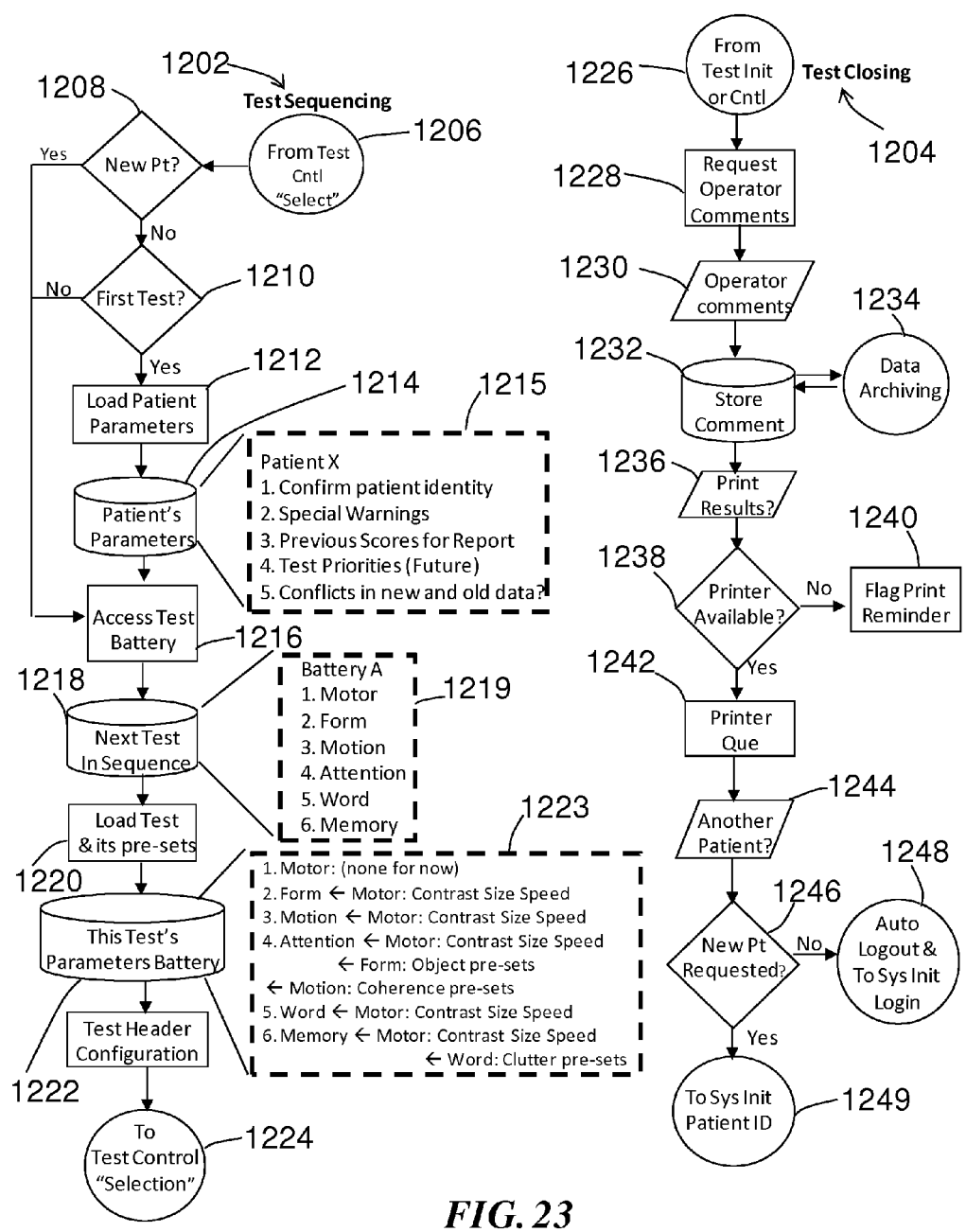
FIG. 23 displays the process flow of test sequencing and test closing.

More particularly, test sequencing and test closing, as applied to the quantitative assessment of functional impairment as described in the present disclosure, may be shown by way of illustration. FIG. 23 illustrates the process flow of test sequencing 1202 in greater detail than as discerned at the step of from test control 1182 of FIG. 22. The subset of steps of from test control 1182 may begin with the from test control 'select' step 1206 of test sequencing 1202. Thereafter, a new patient query 1208 inquires whether a new patient has elected to participate in the test sequencing 1202. If no to new patient query 1208, then a first test query 1210 may be administered. If yes to new patient query prompt 1208, then the test sequencing 1202 proceeds to the step of access test battery 1216. Upon initiating first test query 1210, the test sequencing 1202 commences the step of load patient parameters 1212. Thereafter, the step of reviewing patient's parameters 1214 commences.

Further, the patient parameters reviewed 1215, which may be considered in the step of reviewing patient's parameters 1214, may include, but is not limited to the following: confirm patient identity, special warnings, previous scores for report, test priorities (future), and conflict in new and old data.

Immediately following step of reviewing patient's parameters 1214, the step of access test battery 1216 may commence. Thereafter, the progression of tests may be initiated in the step of next test in sequence 1218, which may include a particular test type 1219. Further, the particular test type 1219 may further include, but is not limited to, tests associated with any, some, or all of motor, form, motion, attention, word, and memory characteristics.

Further, the step of next test in sequence 1218 may start a sequence of the step of load test and its pre-sets 1220, which is immediately followed by an analysis step of this test's parameters battery 1222. More particularly, the step of this test's parameters battery 1222 may include, but is not limited to the details of type of parameter battery 1223, which is listed in list form detail in FIG. 23.

The final step of test sequencing 1202 may be the step of to test control 'selection' 1224, which returns the testing flow process 1100 back to the sequence of test control steps 1152, starting with the test initiation or presentation step 1156. Upon completion of tests and saving test data at the store results step 1136, the sequence of steps in test closing 1204 begins with the step of from test initiation or control 1226.

Thereafter, the step of request operator comments 1228 seeks operator comments 1230, which may be stored as store comments 1232 via a data archiving mechanism 1234. Subsequently, the user is prompted by the query of print results 1236 and the query of printer available 1238. If no to the query of printer available 1238, then the step of flag print reminder 1240. If yes to the query of printer available 1238, then the step of printer que 1242, immediately followed by the prompt of another patient 1244 to print another patient's test results.

Thereafter, a query of new patient requested 1246 may be initiated. If no to query of new patient requested 1246, then the step of auto logout and to system initiation login 1248 appears to the user. If yes to query of new patient requested 1246, then the step of to system initiation patient ID 1249 appears to the user.

Figure 24:
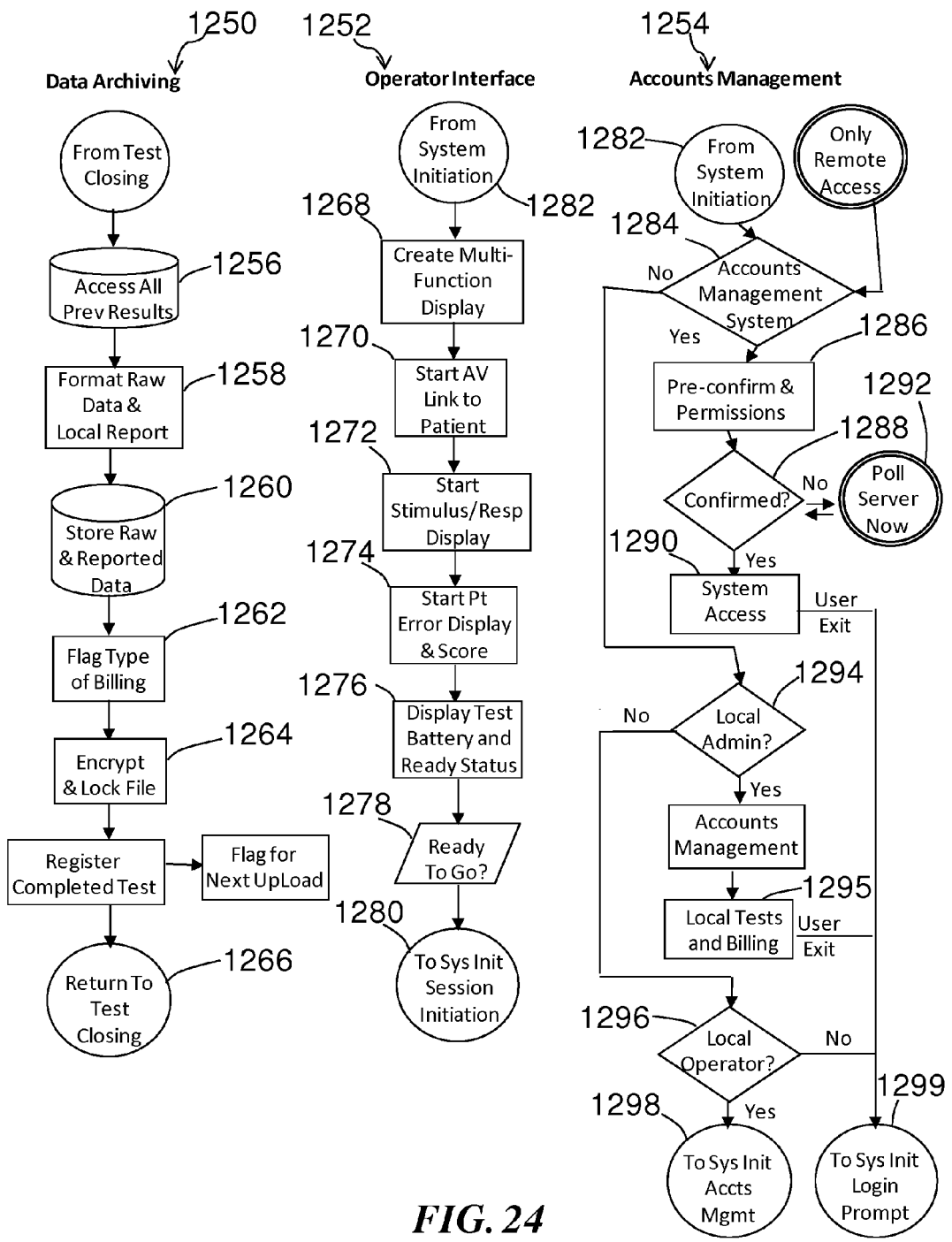
FIG. 24 portrays the sequences of steps for data archiving, operator interface, and accounts management.

More particularly, data archiving, operator interface, and accounts management, as applied to the quantitative assessment of functional impairment as described in the present disclosure, may be shown by way of illustration. FIG. 24 shows sub-sequences of the testing flow process 1100, which may include the sequences of steps for data archiving 1250, operator interface 1252, and accounts management 1254. The process flow of data archiving 1250 may commence from the end of the sequence of steps in test closing 1204 as shown in FIG. 23.

Thereafter the steps for data archiving 1250 may commence with the step of access all previous results 1256, which are formatted in the step of format raw data and reported data 1258. Upon formatting the data from the test sequencing 1202, the data may be stored in the step of store raw data and reported data 1260. Thereafter, the process flow of data archiving 1250 may proceed with the step of flag type of billing 1262 and the subsequent step of encrypt and lock file 1264. The process flow of data archiving 1150 may end with return to test closing 1266.

FIG. 24 also shows sub-sequences of the testing flow process 1100 for the operator interface 1252, which may begin with the step of from system initiation sequence 1282. Thereafter, the operator interface 1252 may proceed with the step of create multi-function display 1268, which is immediately followed by the step of start AV link to patient 1270. Next the operator interface 1252 may proceed the step of start stimulus/response display and score 1272, which initiates the subsequent step of start patient error display and store 1274 and the ensuing step of display the test battery and ready status 1276. Thereafter, the user may be prompted the step of ready to go 1278, which may be immediately followed by the step of to system initiation session initiation 1280.

Moreover, FIG. 24 also shows sub-sequences of the testing flow process 1100 for accounts management 1254, which may begin with the step of from system initiation 1282. Thereafter, the user may be queried with the step of accounts management system 1284. If no to the query of accounts management system 1284, then the follow-up step may be the query local admin 1294 to determine whether the user a local administrator. If yes to the query of asking whether the user is a local admin 1294, then accounts management 1254 may proceed to the step of local tests and billing 1295. However, if no to the query of asking whether the user is a local admin 1294, then accounts management 1254 may proceed to the step of the asking whether the user is a local operator 1190 via the query of local operator 1296. If yes to the query of local operator 1296, then accounts management may proceed to the step of to system initiation accounts management 1298; otherwise, accounts management may proceed to the step of to system initiation login prompt 1299.

Instead, if yes to the query of accounts management system 1284, then the testing flow process 1100 for accounts management 1254 may proceed with the step of pre-confirm and permissions 1286, which may be immediately followed by the step of confirming via the query confirmed 1288. If no to the query confirmed 1288, then the testing flow process 100 for accounts management 1254 may proceed to the step of poll system server now 1292. Instead, if yes to the query step of inquiring confirmed 1288, then the testing flow process 1100 for accounts management 1254 may proceed to the step of system access 1290. Thereafter step of system access 1290, accounts management 1254 undergoes user exit mode and ends the accounts management 1254 at the to system initiation login prompt 1199.

Figure 25:
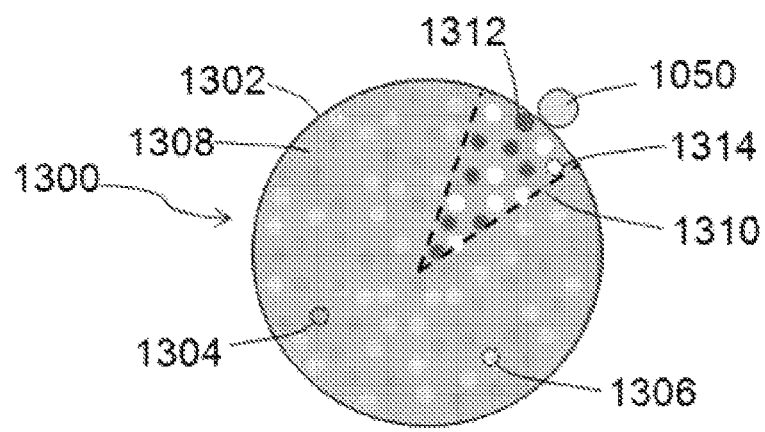
FIG. 25 shows starting phase of the dynamic contrast test.

With reference to FIG. 25 through FIG. 78, the present disclosure includes a screening test battery with high stimulus-response computability to facilitate engaging test subjects while surveying a range of functional domains to detect and quantify a variety of functional impairments.

The fundamental stimulus response contingency common to all of these tests is the segmental presentation of a stimulus in the context of relevant distractors to evoke the subject's positioning of a cursor to indicate the local stimulus.

In one embodiment of the present disclosure, the tests are organized to captures all aspects of sensory input, cognitive transformation, and motoric response, herein called sensory-motor neurocognitive assessment, which may also be known as sensory-cognitive motor tasks. The present disclosure may couple sensory stimulation with the recording of motor responses to assess cerebral cortical function. The stimulus-response patterns are recorded in the context of the different tests, which thereby allow for: 1) the quantification of fundamental sensory and motor functions, 2) the quantification of multiple levels of high cognitive function by measuring its influence on motor function, and 3) the detection of impairments or improvements in any of these functions.

The tests may provide a graph of saliency over time in tasks of sensory-motor neurocognitive assessment task. Further, the tests of the present disclosure may characterize functional impairment in sensory-motor neurocognitive assessment through evaluation of quantifiable characteristics.

One such quantifiable characteristic of impairment in sensory-motor neurocognitive assessment may be high latency to the subject's optimal function in a sensory-motor neurocognitive assessment task, which may be a less steep sensory-motor neurocognitive assessment function.

Another such quantifiable characteristic of impairment may be high variability of optimal function during a sensory-motor neurocognitive assessment task, which may be larger terminal fluctuations.

Yet another such quantifiable characteristic of impairment may be low enhancement of sensory-motor neurocognitive assessment function, particularly being steeper or higher, by valid cueing. The term "valid cueing" may refer to providing a stimulus that allows the subject to have fore-knowledge of a subsequent stimulus, accessing attention or memory that may be able to provide correct information.

Another such quantifiable characteristic of impairment may be high diminution of sensory-motor neurocognitive assessment function, particularly being flatter or lower, via invalid cueing. The term "invalid cueing" may be when attention or memory provides incorrect information about the nature or content of the sensory-motor neurocognitive assessment task.

Further, a disclosed embodiment of the present disclosure may include a motion associated with a stimulus area 199 that may be translation motion, radial motion, or motion that may be in a combination of translation motion and radial motion. Further, the motion associated with the stimulus area 199 may be random in nature.

Further, another embodiment of the present disclosure may include continuous feedback adjusted stimulation. More particularly, the stimuli may have target location specificity, wherein a spatial sub-section of the stimulus is distinct from the remainder of the stimulus by virtue of a gradient or boundary of difference in a single stimulus parameter or a selected set of stimulus parameters. Such a boundary may reflect a single step change at some edge, multiple step changes at successive distances steps away from the target's center, or a graded function with distance from the center of the target.

Further, the tests of the present disclosure may continually change the location of the target in the stimulus field. The present disclosure may include a continually changing response from the subject 192. The target location may change by either angular displacement around an axis of rotation, displacement along a single axis or any fixed or varying orientation, or displacement along multiple axes, such as horizontal and vertical axes.

Additionally, the saliency of the target, which refers to perceptual distinctness of the target from the background, may be continually change during a sensory-motor neurocognitive assessment to alter the difficulty of the task and establish the sensory-motor neurocognitive assessment response function of the subject 192 in the sensory-motor neurocognitive assessment domain.

Further, in the tests of the present disclosure, the cursor 1050 may itself be the target zone of one of the superimposed overlapping tests in which the target position in another test may be controlled as a test target stimulus when the cursor 1050 is presented itself. A computer system 200 may control the saliency associated with the cursor 1050, thereby allowing the subject 192 to perform two sensory-cognitive-motor tasks concurrently, a circumstance which may be associated with dual task interference. More particularly, the subject 192 may be asked to align one target area with another target area during functional impairment testing associated with dual task interference.

Further, during the tests of the present disclosure, the subject performance controls the rate and direction of change in target location and saliency. The speed, maximum acceleration, and rate of direction changes may be increased when the subject 192 if off target and decreased when the subject 192 is on target. The saliency may be increased when the subject 192 if off target, decreased when on target; the rate of change is proportionate to the size and duration of subject error.

Additionally, the duration of testing may be controlled by the size and duration of subject error. More particularly, sustained, stable scores may lead to earlier termination of testing. Multiple oscillations of scores around a stable level may lead to termination. The inability to capture the target at any saliency may lead to termination.

Further, exemplary sensory-motor neurocognitive assessment response characterization protocols may be initiated using configurations informed by previous tests. Visuo-motor response parameters, such as the maximum speed, maximum acceleration, minimum reversal interval, may be established in a particular test and then used as standards in subsequent tests. Further, visual contrast sensitivity measures may be determined and used in subsequent tests to provide each subject 192 with individually standardized stimuli in later tests. Further, sensory-motor neurocognitive assessment visual processing measures may be used for comparison to adjust scores in attentional and memory manipulations superimposed on those tests.

Further, another embodiment of the present disclosure may be to operate a system for quantitative assessment of functional impairment with minimal intervention. The present disclosure may include artificial intelligence capability to enable dynamic testing. Further, each test of the present disclosure may include an ability to dynamically respond to actions of subject 192. Thus, each test in the present disclosure may shorten or lengthen itself automatically in response to the actions taken by the subject 192.

In one embodiment, ten tests may be administered to assess functional impairment of the subject 192. Further, in one embodiment, the tests may be administered in the order described below. However, the methods in accordance with the embodiments of the present disclosure may include the performance of any other subset of the ten tests which may be administered in any order. Further, the tests may encompass present and future known equivalents to the known components referred to herein by way of illustration.

FIG. 25 illustrates the initiation of the dynamic contrast test, which evaluates visuo-motor responses by analysis of the sensori-cognito-motor function in the domains of target movement speed, acceleration, and direction reversal. A patch of high contrast may be comprised of individual elements, which includes, but is not limited to, circles, checkerboard, or stripes. The individual elements, herein called dots, may be equally displaced to either high or low luminance levels and may be distinguished from intermediate luminance background elements.

The starting phase of the dynamic contrast test 1300 may initiate movement of a high color/contrast patch onto the stimulus area 199. An equal number of darker-contrast dots 1304 and lighter-contrast dots 1306 may be presented within a neutral-contrast background stimulus area 1308, which may be surrounded by the circular border 1302. The darker-contrast dots 1304 and lighter-contrast dots 1306 may be randomly assigned in size in the range of three degrees or smaller, thereby maintaining a pink noise spatial frequency composition of dots across the screen. A high color/contrast patch, which may be an active stimulus radial segment 1310, which may move onto the stimulus area 199. The active radial segment 1310, which may be a twenty-five degrees section within the circular border 1302, may contain a number of relatively higher contrast level darker dots 1312 and relatively lower contrast level lighter dots 1314.

The darker-contrast dots 1304 and lighter-contrast dots 1306 fade in and out in the neutral-contrast background stimulus area 1308 with randomly assigned life time periods that are chosen within a timed interval. An operator 190 may pre-set the brightness level of the neutral-contrast background stimulus area 1308, the number of darker-contrast dots 1304 and lighter-contrast dots 1306 within the circular border 1302, the relative color of the of the neutral-contrast background stimulus area 1308 relative to the color of the darker-contrast dots 1304 and lighter-contrast dots 1306, and the maximum diameter of the darker-contrast dots 1304 and lighter-contrast dots 1306.

A stimulus generator 450 supplies an algorithm that may be applied to relatively higher contrast level darker dots 1312 and relatively lower contrast level lighter dots 1314 within the active stimulus radial segment 1310, which may make the relatively higher contrast level darker dots 1312 achieve a relatively higher contrast level compared to the dots in the neutral-contrast background stimulus area 1308 and the relatively lower contrast level lighter dots 1314 achieve a relatively lower contrast level compared to the dots in the neutral-contrast background stimulus area 1308.

The operator 190 may pre-set settings for the active stimulus radial segment 1310, the brightness level of the active stimulus radial segment 1310, the number of relatively higher contrast level darker dots 1312 and relatively lower contrast level lighter dots 1314 within the active stimulus radial segment 1310, the relative color of the of the active stimulus radial segment 1310 relative to the color of relatively higher contrast level darker dots 1312 and relatively lower contrast level lighter dots 1314, and the maximum diameter of the relatively higher contrast level darker dots 1312 and relatively lower contrast level lighter dots 1314.

During the starting phase of the dynamic contrast test 1300, the active stimulus radial segment 1310 may generate the highest contrast level for the relatively higher contrast level darker dots 1312 and the lightest contrast level for the relatively lower contrast level lighter dots 1314 within the active stimulus radial segment 1310. Then, the active stimulus radial segment 1310 may begin to move continuously, and while doing so, the active stimulus radial segment 1310 may direction in either a clockwise or counterclockwise direction and/or it can accelerate or decelerate.

The subject 192 may be asked to identify and to parallel the movement of the active stimulus radial segment 1310 using an subject manipulandum 1402 during the starting phase of the dynamic contrast test 1300. The subject's control and movement of an subject manipulandum 1402 may be tracked on the subject display 198 with a cursor 1050. The active stimulus radial segment 1310 may be tracked with the cursor 1050 via the subject's control.

As the active stimulus radial segment 1310 moves around the neutral-contrast background stimulus area 1308, the contrast level within the active stimulus radial segment 1310 may begin to change along with the location, direction, and speed of the active stimulus radial segment 1310. As the contrast level of the active stimulus radial segment 1310 begins to decline, the subject 192 will find it to be more difficult to follow the movements of the active stimulus radial segment 1310. Therefore, the operator 190 may gauge an approximate threshold for the relative contrast level of the active stimulus radial segment 1310 that the user can decipher.

Figure 26:
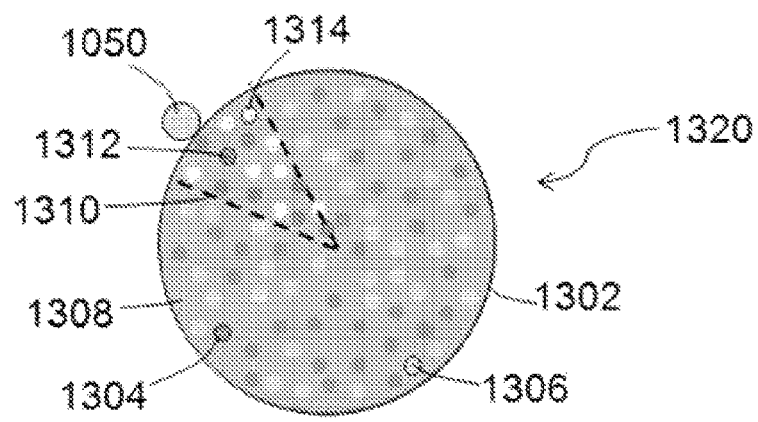
FIG. 26 illustrates the intermediate phase of the dynamic contrast test.

FIG. 26 shows the intermediate phase of the dynamic contrast module test 1320, a phase marked by a discontinuous nature. During this discontinuous phase, the active stimulus radial segment 1310 may move about in a discontinuous fashion, beginning with fade-out stage of a low contrast level for the active stimulus radial segment 1310 at a level equal to or lower than the initial contrast level of the starting phase of the dynamic contrast test 1300.

During this fade-out period, the active stimulus radial segment 1310 may fade-out initially. Subsequently, the active stimulus radial segment 1310 may fade-in with the relatively higher contrast level darker dots 1312 and relatively lower contrast level lighter dots 1314 within the active stimulus radial segment 1310 being recreated in contrast conditions according to original randomization conditions; however, the recreated relatively higher contrast level darker dots 1312 and relatively lower contrast level lighter dots 1314 are moved, via a motion herein analogous to a jumping motion, to a new location within the neutral-contrast background stimulus area 1308, which is filled with darker-contrast dots 1304 and lighter-contrast dots 306 and may also be surrounded by the circular border 1302.

Whenever the subject 192 moves the subject manipulandum 402, the cursor 1050 may track the target active stimulus radial segment 1310; if the subject 192 can successfully track the target active stimulus radial segment 1310 within a predetermined limit, an instant bright flash and beep may signal and may confirm the action of the subject 192. The intermediate phase of the dynamic contrast test 1320 may continue with further jumps until the operator 190 develops a further refined threshold; subsequent restarting of the intermediate phase of the dynamic contrast test 1320 may continue at varying levels of contrast and rates of contrast increase, resulting in a repeat process until an ensuing threshold may be attained.

Figure 27:
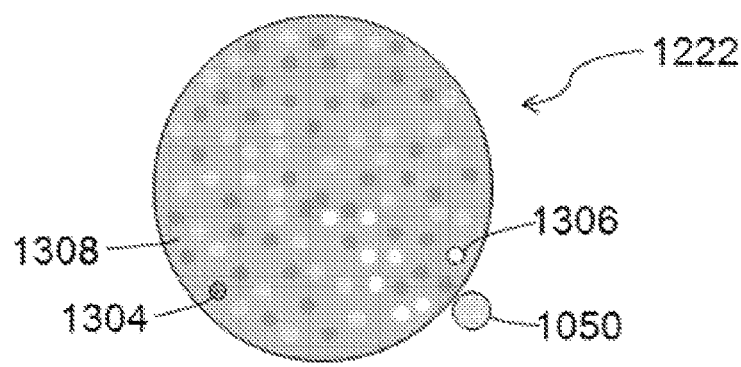
FIG. 27 displays the termination phase of the dynamic contrast test.

FIG. 27 illustrates the termination phase of the dynamic contrast test 1322, during which the subject 192 may no longer distinguish the presence of an active stimulus radial segment 1310 within the neutral-contrast background stimulus area 1308. At this point, the final location of the cursor 1050 may mark the critical threshold, for which the data of the threshold in used in the ensuing tests. Immediately following the critical threshold point, the darker-contrast dots 1304 and lighter-contrast dots 1306 may fill the entire the neutral-contrast background stimulus area 1308, which may be surrounded by the circular border 1302.

Figure 28:
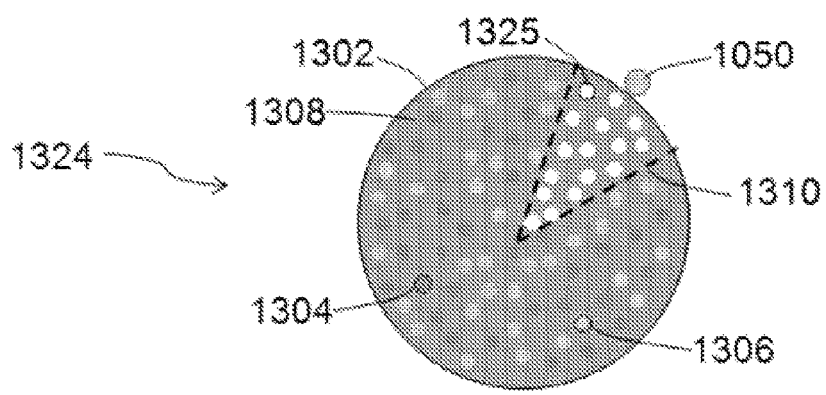
FIG. 28 shows starting phase of the visual contrast sensitivity test.

FIG. 28 depicts the starting phase of the visual contrast sensitivity test 1324, which may involve the implementation of a patch of high luminance elements 1325 onto an active stimulus radial segment 1310, which may be within the circular border 1302. The patch of high luminance elements 1325 may include, but are not limited, to being circles, checkerboard, or stripes. The individual elements may be distinguished from intermediate luminance background elements to vary saliency. The subject 192 controls the position and movement of a cursor 1050 to match that of the target.

During the starting phase of the visual contrast sensitivity test 1324, high luminance elements 1325 may be distinguished from the darker-contrast dots 1304 and lighter-contrast dots 1306 that may be randomly assigned in the neutral-contrast background stimulus area 1308.

Figure 29:
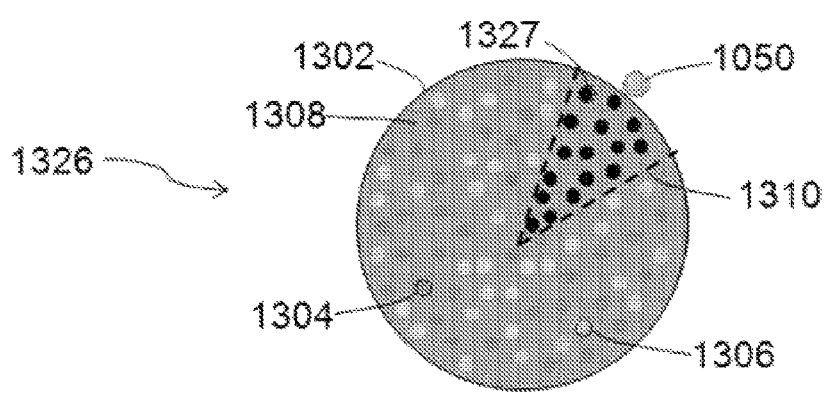
FIG. 29 illustrates the intermediate phase of the visual contrast sensitivity test.

FIG. 29 depicts the intermediate phase of the visual contrast sensitivity test 1326. The high luminance elements 1325 may be automatically transitioned to becoming low luminance, thereby becoming low luminance elements 1327, during the intermediate phase of the visual contrast sensitivity test 1325. The transition to becoming low luminance elements 1327 may enable the subject 192 to determine the threshold.

Figure 30:
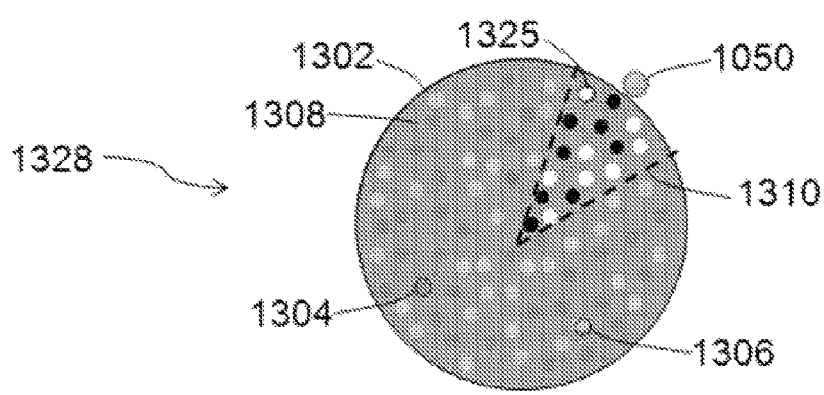
FIG. 30 displays the termination phase of the visual contrast sensitivity test.

FIG. 30 illustrates the termination phase of the visual contrast sensitivity test 1328, during which the subject 192 may be presented with both a mixed luminance elements, comprising both high luminance elements 1325 and low luminance elements 1327, within the active stimulus radial segment 1310. During the process of the stimulus radial segment 1310 gradually presenting a mixed luminance, the subject 192 may be cued to determine the threshold to achieve an equal number of high luminance elements 1325 and low luminance elements 1327 within the active stimulus radial segment 1310. At the point when the subject 192 may determine an equal number of high luminance elements 1325 and low luminance elements 1327, the final location of the cursor 1050 may mark the critical threshold, for which the data of the threshold in used in the ensuing tests.

Figure 31:
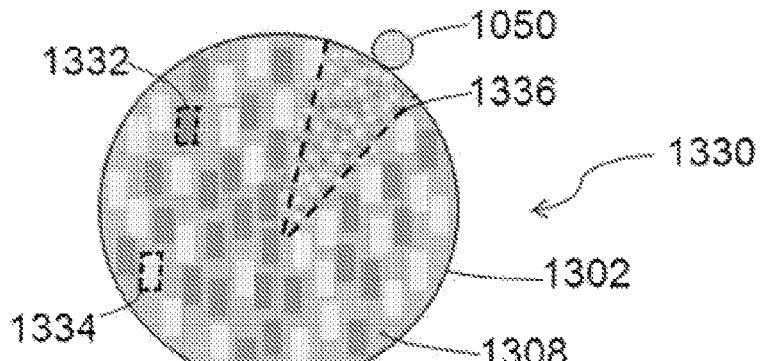
FIG. 31 portrays the starting phase of the visual form discrimination test.

FIG. 31 depicts the initiation of the visual form discrimination test, during which patches of regular shapes may be distorted to distinguish target area shapes from their background. During the visual form discrimination test, patches of regular shapes may be distorted to distinguish the target area shapes from the background. The patches of regular shape may be distorted in a manner including, but not limited to, size, shape, aspect ratio, line thickness, and/or orientation. The subject 192 may control the position and movement of cursor 1050 to match that of the target.

During the starting phase of the visual form discrimination test 1330, an equal number of darker-contrast rectangles 1332 and lighter-contrast rectangles 1334 may be presented within a neutral-contrast background stimulus area 1308, which may be surrounded by the circular border 1302. The darker-contrast rectangles 1332 and lighter-contrast rectangles 1334 may be randomly assigned in sizes of one unit length width and three unit lengths height across the screen. An active visual form module stimulus radial segment 1336, which may be a twenty-five degrees section within the circular border 1302, contains a number of relatively higher contrast level darker rectangles 1332 and relatively lower contrast level lighter rectangles 1334.

An operator 190 may pre-set the brightness level of the neutral-contrast background stimulus area 1308, the number of darker-contrast rectangles 1332 and lighter-contrast rectangles 1334 within the circular border 1302, the relative color of the of the neutral-contrast background stimulus area 1308 relative to the color of the darker-contrast rectangles 1332 and lighter-contrast rectangles 1334, and the maximum diameter of the darker-contrast dots 1304 and lighter-contrast dots 1306.

The darker-contrast rectangles 1332 and lighter-contrast rectangles 1334 may fade in and out in the neutral-contrast background stimulus area 1308 with assigned life time periods that may chosen within a timed interval set between thirty-six and one-hundred eight frames at seventy-two frames per second with emergence and fading occurring over three frames. Further, the darker-contrast rectangles 1332 and lighter-contrast rectangles 1334 may fade in and out in the neutral-contrast background stimulus area 1308 while moving to random new positions.

The subject 192 may be asked to identify the active visual form module stimulus radial segment 1336 using a maninpulandum 402, during the starting phase of the visual form discrimination test 1330. The subject's control and movement of a subject manipulandum 402 may be tracked on the subject display 198 with a cursor 1050. The active visual form module stimulus radial segment 1336 may be tracked with the cursor 1050 via the subject's control.

Figure 32:
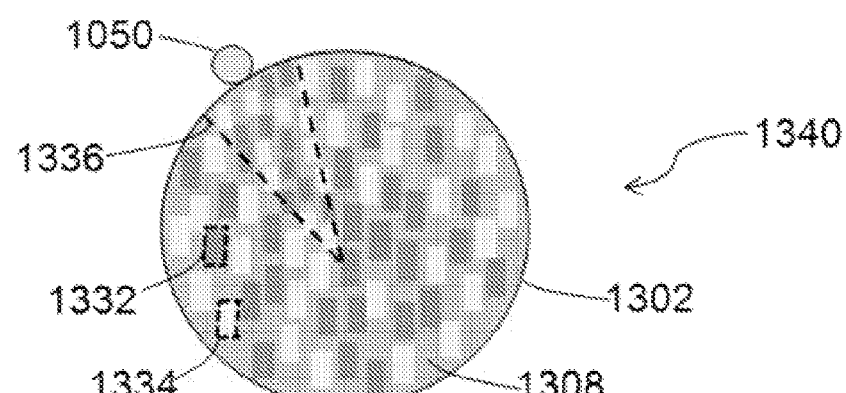
FIG. 32 shows the intermediate phase of the visual form discrimination test.

FIG. 32 displays the intermediate phase of the visual form discrimination test 1340, a phase marked by a discontinuous nature. During this discontinuous phase, the rectangular elements within the active visual form module stimulus radial segment 1336 may vary in size, shape, and orientation while the active visual form module stimulus radial segment 1336 moves continuously around the circular border 1302 with varying levels of distinctiveness. More particularly, the active visual form module stimulus radial segment 1336 may move continuously around the circular border 1302 while accelerating or decelerating and/or moving clockwise or counterclockwise; furthermore, the rectangular elements within the active visual form module stimulus radial segment 1336 may change direction of movement from clockwise to counterclockwise or vice-a-versa.

The subject 192 may be asked to parallel the movement of the active visual form module stimulus radial segment 1336 using a cursor 1050, which a may be physical interface akin to a wheel or a joystick, during the intermediate phase of the visual form module test 1340. Subsequently, the active visual form module stimulus radial segment 1336 fades-in with the relatively higher contrast level darker rectangles 1332 and relatively lower contrast level lighter rectangles 1334 within the active visual form module stimulus radial segment 1336 being recreated in contrast conditions according to original randomization conditions; however, the recreated relatively higher contrast level darker rectangles 1332 and relatively lower contrast level lighter rectangles 1334 may be moved, via a motion herein analogous to a jumping motion, to a new location within the neutral-contrast background stimulus area 1308.

Whenever the subject 192 moves the cursor 1050 into the target active stimulus radial segment 1310, an instant bright flash and beep may signal and may confirm the action of the subject 192. The intermediate phase of the visual form module test 1340 may continue with further jumps until the operator 190 develops a further refined threshold; subsequent restarting of the intermediate phase of the intermediate phase of the visual form module test 1340 may continue at varying levels of contrast and rates of contrast increase, resulting in a repeat process until an ensuing threshold is attained.

Figure 33:
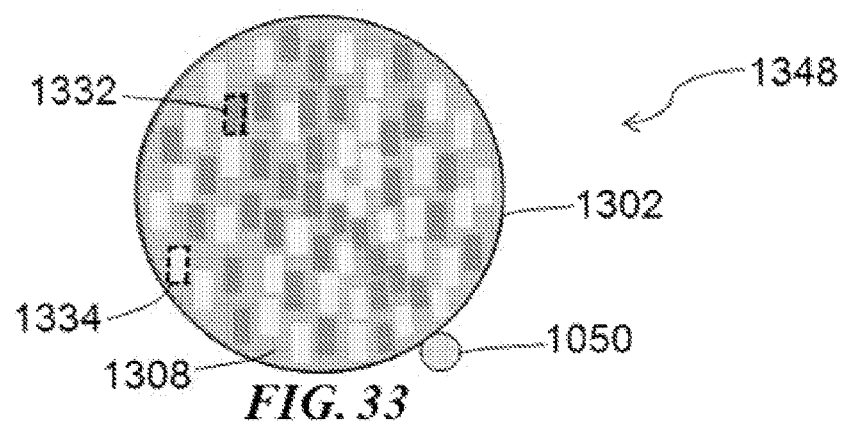
FIG. 33 illustrates the termination phase of the visual form discrimination test.

FIG. 33 illustrates the termination phase of the dynamic contrast discrimination test 1348, during which the subject 192 may no longer distinguish the presence of the active visual form module stimulus radial segment 1336 within the neutral-contrast background stimulus area 1308. Hence, the darker-contrast rectangles 1332 and lighter-contrast rectangles 1334 may fill the entire the neutral-contrast background stimulus area 1308, which may be surrounded by the circular border 1302. At this point, the final location of the cursor 1050 may mark the critical threshold, for which the data of the threshold may be used in the ensuing tests.

Figure 34:
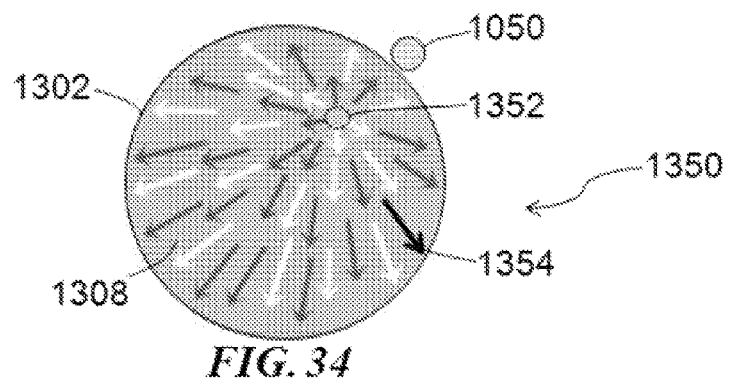
FIG. 34 depicts the initiation of the visual motion discrimination test.

FIG. 34 depicts the initiation of the visual motion discrimination test, during which spots move in a direction or create a motion defined edge or a point. The subject 192 may control the position and movement of a cursor 1050 to match of the target. During the visual motion discrimination test, the salience of the target may be decreased by shifting more elements to random motion.

The starting phase of the visual motion discrimination test 1350 may include segmental presentations of a radial center of motion in optic flow. An equal number of darker-contrast dots 1304 and lighter-contrast dots 1306 may be presented within a neutral-contrast background stimulus area 1308, which may be surrounded by the circular border 1302. The contrast levels for the darker-contrast dots 1304 and lighter-contrast dots 1306 may be set two confidence intervals above the threshold established in the starting phase of the dynamic contrast test 1300. The darker-contrast dots 1304 and lighter-contrast dots 1306 may move in an outward radial pattern 1354 by moving away from a focus of expansion 1352, which may be a designated point within the circular border 1302.

More particularly, the focus of expansion, or the focus of contraction that may be created by inward directed movement 1352 may be located anywhere within the circular border; however the eccentricity of the focus of expansion 1352 may be pre-set. Further, the darker-contrast dots 1304 and lighter-contrast dots 1306 may be randomly assigned in size in the range of three degrees or smaller, thereby maintaining a pink noise spatial frequency composition of dots across the screen. Moreover, the control variables may include background brightness neutral-contrast background stimulus area 1308 and dot density, color, spatial frequency, and speed of the darker-contrast dots 1304 and lighter-contrast dots 1306. The ratio of dots that may be moving radially outwards to the number of total dots may be known as the coherence ratio. Of note, the ratio may be full coherence, with a ratio of one to one, or no coherence, with a ratio of zero to one.

The darker-contrast dots 1304 and lighter-contrast dots 1306 may fade and emerge with a random lifespan between thirty-six and seventy-two frames with three frames for emergence and three frames for fading. The speed of the darker-contrast dots 1304 and lighter-contrast dots 1306 may be a $\sin^2$ function of the angular distance from the focus of expansion 1352. The starting phase of the visual motion discrimination test 1350 may begin with full coherence where the subject 192 can all points moving in a outward radial pattern 1354 away from the singular point known as the focus of expansion 1352.

Figure 35:
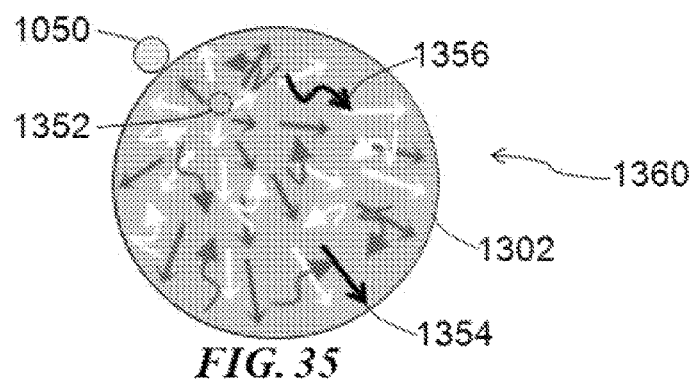
FIG. 35 shows the intermediate phase of the visual motion discrimination test.

FIG. 35 shows the intermediate phase of the visual motion discrimination test 1360, a phase during which the focus of expansion 1352 may move with varying movements of coherence, location, direction, and speed. The darker-contrast dots 1304 and lighter-contrast dots 1306 may move in an outward radial pattern 1354 or in a random fashion 1356 from a frame to another frame. The subject's cursor identification is a twenty-five degree radial segment, such that the subject 192 may need to move the cursor 1050 so that the focus of expansion 1352 falls within the twenty-five degree segment.

When the subject 192 moves the cursor 1050 to enter the twenty-give degree segment, then the intermediate phase of the visual motion discrimination test 1360 may produce a bright flash and beep. Starting with a low level of coherence, the focus of expansion 1352 may begin to move in a discontinuous, jumping motion around the circular border 1302 with each fade and emergence sequence; with each such jump, the coherence level increases.

Figure 36:
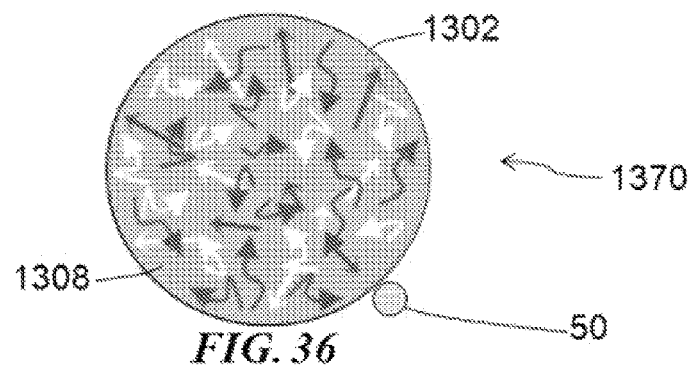
FIG. 36 illustrates the termination phase of the visual motion discrimination test.

FIG. 36 illustrates the termination phase of the visual motion discrimination test 1370, during which the subject 192 may no longer distinguish the presence of the twenty-five degree segment that may be associated with the focus of expansion 1352. Hence, the darker-contrast dots 1304 and lighter-contrast dots 1306 may fill the entire the neutral-contrast background stimulus area 1308, which may be surrounded by the circular border 1302. At this point, the final location of the cursor 1050 may mark the critical threshold, for which the data of the threshold in used in the ensuing tests. Ultimately, this threshold may be achieved by successively constraining the starting coherence and the rate of increase.

With reference to FIGS. 34, 35, and 36, may include, but is not limited to, presentations of a radial center of motion in optic flow, which may include the focus of expansion 1352 in the stimulus area 199. Future equivalents of the present subject matter may present a uniform simple planar translational motion stimulus, wherein the subject 192 may orient a cursor 1050, which may include, but is not limited to a ball-and-stick cursor, in the direction of motion. Further, future equivalents of the present subject matter may present a circular pattern of motion with the center of rotation moving around the stimulus area 199 just as the focus of expansion 1352 may move around in a radial optic flow field. Further, the circular and radial stimuli may be summed to create a spiral in which the center of the spiral may move around the stimulus area 199.

Figure 37:
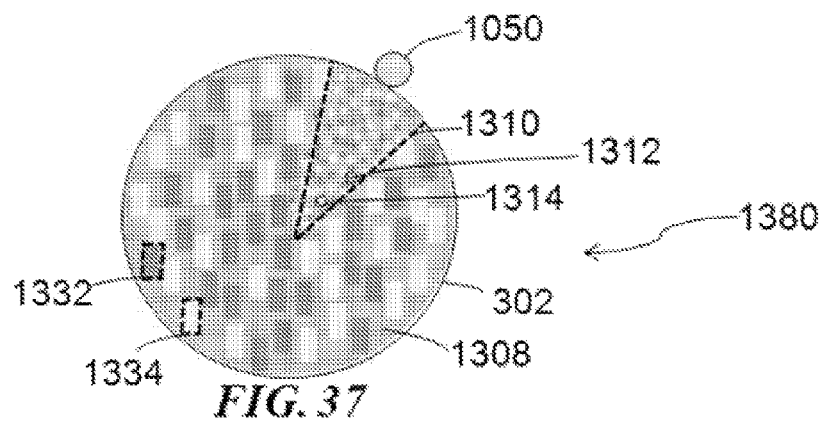
FIG. 37 depicts the superposition of form and motion tests.

FIG. 37 depicts the superposition of form and motion tests, herein called the spatial distractor tasks test, to assess the combination of visual motion and visual form. The subject 192 may control the position and movement of cursor 1050 to match that of the target, while form, motion, or other basic stimuli are combined with brief visual or auditory distracters to interfere with the task.

The starting phase of the spatial distractor tasks test 1380 may include the superimposed darker-contrast rectangles 1332 and lighter-contrast rectangles 1334 from the starting phase of the visual form discrimination test 1330 in FIG. 31 together with relatively higher contrast level darker dots 1312 and relatively lower contrast level lighter dots 1314 within the active stimulus radial segment 1310 from the starting phase of the dynamic contrast test 1300 in FIG. 25.

The number of darker-contrast rectangles 1332 and lighter-contrast rectangles 1334 in the starting phase of the spatial distractor tasks test 1380 may be one-half of the number of the equivalent structures of the starting phase of the visual form discrimination test 1330. The number of relatively higher contrast level darker dots 1312 and relatively lower contrast level lighter dots 1314 within the active stimulus radial segment 1310 may be one-half of the number of the equivalent structures of in the starting phase of the dynamic contrast test 1300. Hence, both patterns may be shown are one-half of the cue element density than previously with the starting phase of the visual form discrimination test 1330 and the starting phase of the dynamic contrast test 1300 respectively.

Additionally, the darker-contrast rectangles 1332 and lighter-contrast rectangles 1334 in the starting phase of the spatial distractor tasks test 1380 have distinction levels set between two confidence levels below and above the established threshold for distinctiveness from the termination phase of the dynamic contrast discrimination test 1348 of FIG. 33. As described in great detail in the detailed description of the starting phase of the visual form discrimination test 1330, the darker-contrast rectangles 1332 and lighter-contrast rectangles 1334 may fade in and out in the neutral-contrast background stimulus area 1308 while moving to random new positions.

Additionally, relatively higher contrast level darker dots 1312 and relatively lower contrast level lighter dots 1314 within the active stimulus radial segment 1310 in the starting phase of the spatial distractor tasks test 1380 have coherence levels set between two confidence intervals below and above the established threshold for coherence from the termination phase of the dynamic contrast test 1322 in FIG. 27. As described in great detail in the detailed description of the starting phase of the visual form discrimination test 1330, relatively higher contrast level darker dots 1312 and relatively lower contrast level lighter dots 1314 within the active stimulus radial segment 1310 may fade in and out in the neutral-contrast background stimulus area 1308 with randomly assigned life time periods that are chosen within a timed interval.

Further, the active stimulus radial segment 1310 may undergo the same sequence of settings and conditions outlined by the algorithm of the stimulus generator 450 as described in great detail in the starting phase of the visual form discrimination test 1330. Meanwhile, auditory distracters or other basic stimuli may interfere with the task, which may be associated with dual task interference. Further, dual task interference may require the subject to align one target area on top of another target area. Further, the subject may need to utilize two functions of its brain, which may cause interference amongst those brain functions.

Figure 38:
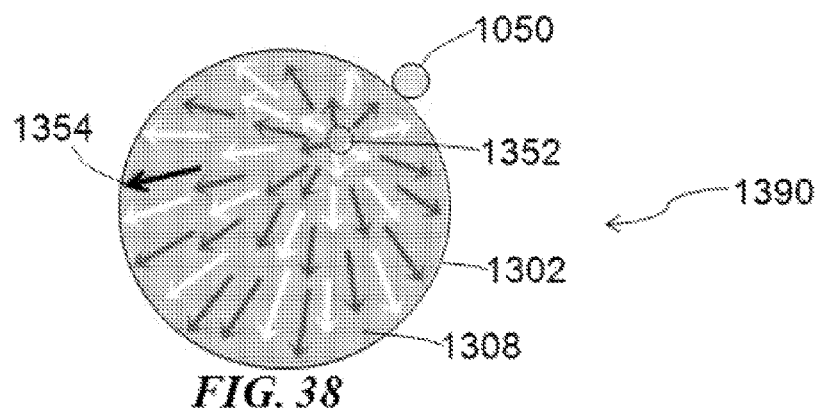
FIG. 38 illustrates the intermediate phase of the spatial attention effects test.

FIG. 38 illustrates the intermediate phase of the spatial distractor tasks test 1390, a phase during which the focus of expansion 1352 moves with varying movements of coherence, location, direction, and speed outlined by the detailed description of the intermediate phase of the visual motion discrimination test 1360 in FIG. 35. The variations with the focus of expansion 1352 may be superimposed with active stimulus radial segment 1310 described in detail in the starting phase of the spatial distractor tasks test 1380 of FIG. 37. This superimposition of tasks may test the subject's cognitive processing ability while the subject 192 must utilize two functions of its brain, wherein the functions may interfere with each other.

In order to ensure that the subject 192 understands the complexity of the superimposed test iteration present in the intermediate phase of the spatial distractor tasks test 1390, the first continuous movement may be performed at two confidence intervals above the threshold established in termination phase of the dynamic contrast module test 1322 and two confidence intervals below the threshold established in the termination phase of the dynamic contrast discrimination test 1348. Subsequently, the continuous movement may be performed at two confidence intervals above the threshold established in termination phase of the dynamic contrast module test 1322 and two confidence intervals below the threshold established in the termination phase of the dynamic contrast discrimination test 1348.

The subject's control and movement of a subject manipulandum 402 may be implemented to track to the form target and the motion target onto the subject display 198 with the use of a cursor 1050. The form target and the motion target locations may be separated by a predetermined separation distance within the range of one-hundred fifty degrees and two-hundred ten degrees.

The subject 192 may use the cursor 1050 to track form target, which includes the form changes of the darker-contrast rectangles 1332 and lighter-contrast rectangles 1334. The subject 192 may use the cursor 1050 to track motion of motion target, which includes the relatively higher contrast level darker dots 1312 and relatively lower contrast level lighter dots 1314. Further, the cursor 1050 may also be implemented to track the motion and to track the form in the respective tests of FIGS. 39, 40, and 41 as outlined in greater detail in the accompanying descriptions of those respective figures.

After a pre-selected limit, the two stimuli of motion and form shift places in the paradigm and the subject 192 may be instructed to shift tasks.

Figure 39:
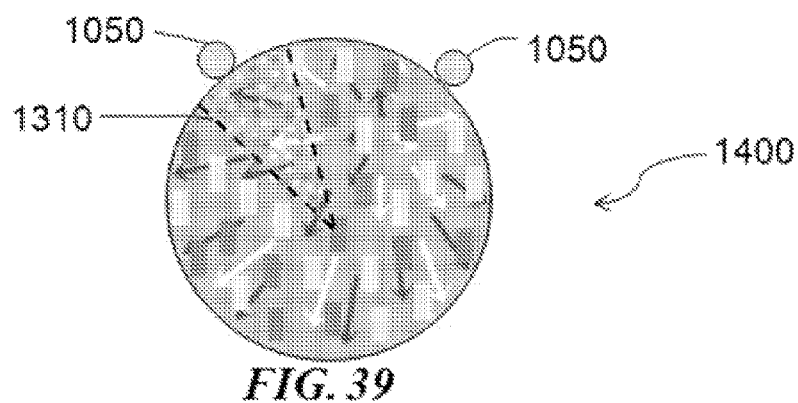
FIG. 39 represents the left-up form target and right-up motion target of the visual motion and visual form attention test.

FIG. 39 represents the left-up form target and right-up motion target of the visual motion and visual form attention test 1400. Both the patterns of darker-contrast rectangles 1332 and lighter-contrast rectangles 1334 and relatively higher contrast level darker dots 1312 and relatively lower contrast level lighter dots 1314 within the active stimulus radial segment 1310 may be superimposed during phase 1400.

Figure 40:
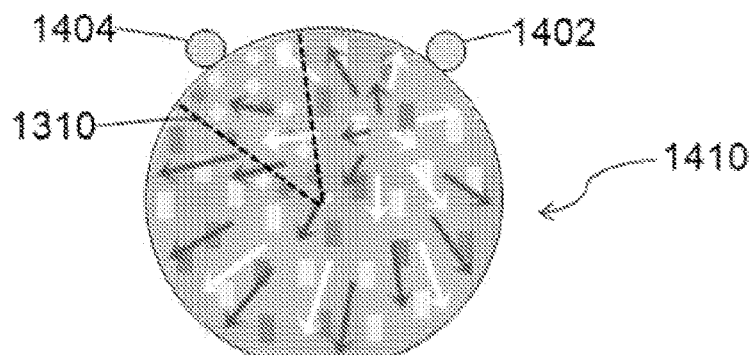
FIG. 40 displays the left-up form, low-distinct target and right-up motion, high-coherence target of the visual motion and visual form attention test.

FIG. 40 displays the left-up form, low-distinct target and right-up motion, high-coherence target of the visual motion and visual form attention test 1410. Both the patterns of darker-contrast rectangles 1332 and lighter-contrast rectangles 1334 and relatively higher contrast level darker dots 1312 and relatively lower contrast level lighter dots 1314 within the active stimulus radial segment 1310 may be superimposed during the phase of the left-up form, low-distinct target and right-up motion, high-coherence target of the visual motion and visual form attention test 1410.

Figure 41:
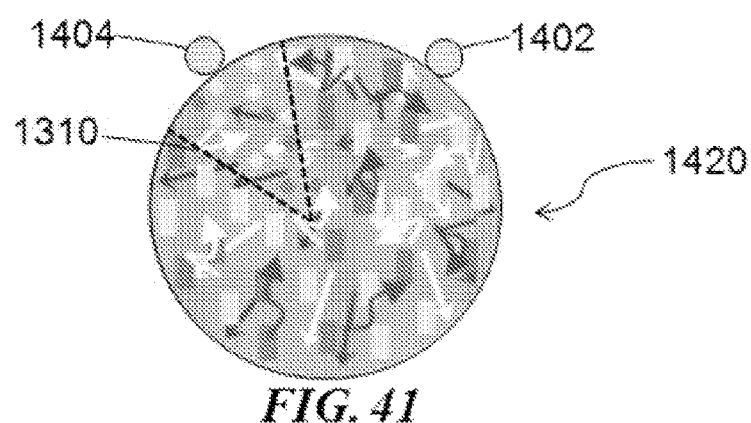
FIG. 41 shows the left-up form, high-distinct target and right-up motion, low-coherence target of the visual motion and visual form attention test;'

FIG. 41 shows the left-up form, high-distinct target and right-up motion, low-coherence target of the visual motion and visual form attention test 1420. Both the patterns of darker-contrast rectangles 1332 and lighter-contrast rectangles 1334 and relatively higher contrast level darker dots 1312 and relatively lower contrast level lighter dots 1314 within the active stimulus radial segment 1310 may be superimposed during the phase of the left-up form, high-distinct target and right-up motion, low-coherence target of the visual motion and visual form attention test 1420.

Figure 42:
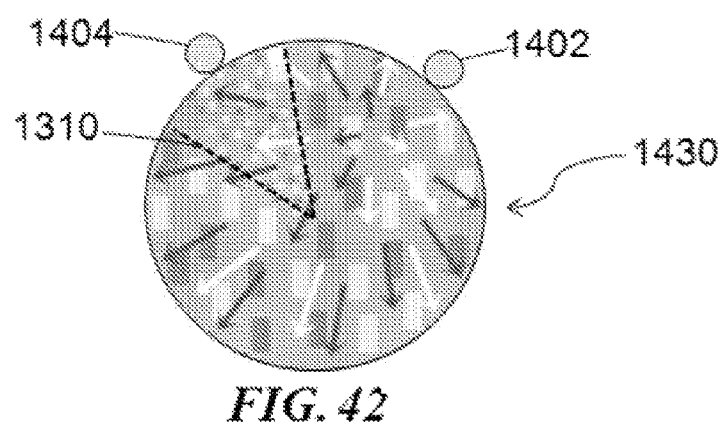
FIG. 42 portrays the left-up form, high-distinct target and right-up motion, high-coherence target of the visual motion and visual form attention test.

FIG. 42 portrays the left-up form, high-distinct target and right-up motion, high-coherence target of the visual motion and visual form attention test 1430. Both the patterns of darker-contrast rectangles 1332 and lighter-contrast rectangles 1334 and relatively higher contrast level darker dots 1312 and relatively lower contrast level lighter dots 1314 within the active stimulus radial segment 1310 may be superimposed during the phase of the left-up form, high-distinct target and right-up motion, high-coherence target of the visual motion and visual form attention test 1330.

Further, the spatial distractor tasks testing of the subject matter regarding FIGS. 37, 38, 39, 40, 41, and 42, may be added to any test of the present disclosure. The radial optic flow stimulus may be the substrate for the spatial distractor tasks testing; however any other functional assessment test may be associated with the stimulus for the substrate of the spatial distractor tasks testing. The present disclosure describes a subject 192 that is performing a spatial discrimination task and may position the cursor 1050, which may be a ball-and-stick cursor, at the location on the stimulus area 199 where the subject 192 sees a high saliency wedge within the stimulus area 199. The present disclosure may superimpose the intermittent addition of an alternative, high saliency cue somewhere else, such that the subject 192 may transiently shift attention to that distractor so that the distractor is not task relevant and also not to degrade the target following in the main task. The distractor may include, but is not limited to, a wedge of unique stimulus elements flashing for one to three seconds at a position far from the target wedge, an area of unique elements flashing on for one to three seconds at a position far from the target edge, or the transient displacement of the cursor 1050 to some place other than that specified by the subject 192.

Further, the spatial distractor tasks testing of the subject matter regarding FIGS. 37, 38, 39, 40, 41, and 42, may be associated with spatial memory testing, in which the spatial memory of a subject 192 may be used to augment the subject's response sensitivity in any of the main tasks, which may include, but it not limited to, form, motion, and words. In these main tasks, the target wedge may transiently flash to some high saliency cue, which may include, but it not limited to one hundred percent saliency of the target cue, or all white, or all black, and then may revert to its near threshold saliency and makes a stereotyped movement or selected number of movements. After repeated exposures, the subject 192 may implicitly, that is without being told, acquire knowledge of the flashes' meaning. The subject 192 may use that information to enhance the ability to follow the target stimulus through that spatial sequence; for instance, the subject 192 may further use movement as a stimulus for learning a sequence of movements. Further, spatial memory testing may include, but is not limited to sequence memory or location memory. Further, spatial memory testing may be a combination of testing associated with sequence memory and location memory.

Figures 43, 44, 45, 46:
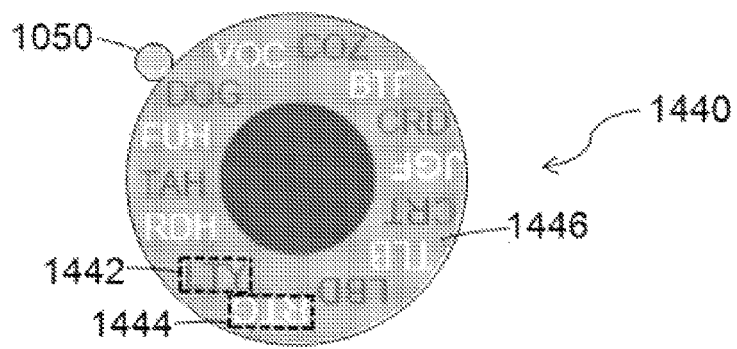
FIG. 43 displays the starting phase of the word recognition module.
FIG. 44 shows normal letters orientation.
FIG. 45 shows mirror rotated letters orientation.
FIG. 46 shows inverted letters orientation.

FIG. 43 displays the starting phase of the letter identification latency module 1440, during which equal numbers of alternating black-colored letter sets 1442 and white-colored letter sets 1444 may be presented in a fixed sequence around the edge of circular, stimulus area 1446. The three letters words may be distributed in the background, which may comprise a cluster of other three letter sets and also a real word that defines a target. Further, a word may be associated with correct letters that may be imbedded in a stimulus ring with three letter figures made of non-letters.

The three letters for the alternating black-colored letter sets 1442 and white-colored letter sets 1444 may fall into the following categories of: 1) target word, 2) legal-non-words, 3) illegal non-words, 4) flipped illegal non-words, and 5) flipped and rotated non-word. The three letters may be in different orientations or may utilize false fonts as further outlined in FIGS. 44, 45, and 46.

Font, size, and position of the black-colored letter sets 1442 and white-colored letter sets 1444 may be determined by the pre-sets from the starting phase of the visual motion discrimination test 1350 and the starting phase of the visual form discrimination test 1330. The contrast of the letters may be set at being two confidence intervals above the subject's contrast threshold obtained in the termination phase of the visual motion discrimination test 1370.

FIG. 44 shows normal letters orientation 1450, which may be applied towards the three letters that were described previously in the starting phase of the letter identification latency module 1440 of FIG. 43.

FIG. 45 shows mirror rotated letters orientation 1454, which may be applied towards the three letters that were described previously in the starting phase of the letter identification latency module 1440 of FIG. 43.

FIG. 46 shows inverted letters orientation 1458, which may be applied towards the three letters that were described previously in the starting phase of the letter identification latency module 1440 of FIG. 43.

Figure 47:
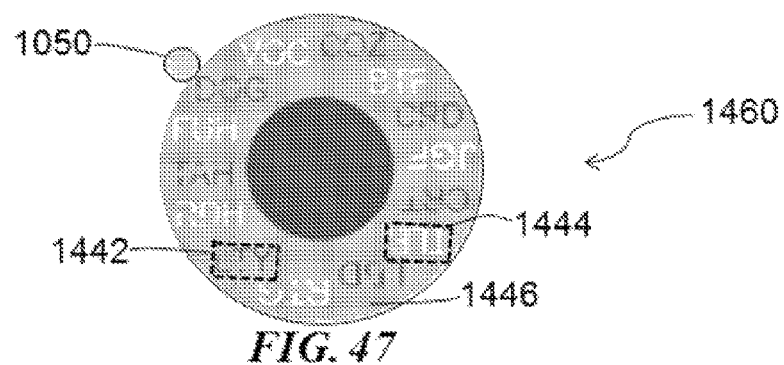
FIG. 47 shows the intermediate phase of the word recognition module.

FIG. 47 shows the intermediate phase of the letter identification latency module 1460, during which the three letters of the black-colored letter sets 1442 and white-colored letter sets 1444, which may be within the circular stimulus area 1446, may be partially obscured to reduce their saliency and to establish the cursor tracking response function. During the start of the test paradigm of the intermediate phase of the letter identification latency module 1460, the subject 192 may be presented with the highest level of letter continuity. A plurality of the item stimulus may set drift around the stimulus area 199, which may be a ring, in unison. The subject 192 may move the cursor 1050 to the real word and follow it for a predetermined time period or a predetermined extent as angular degrees of drift. The score may be derived from the time it takes the subject 192 to register the location of the real word that may be captured and tracked.

Subsequently, word continuity may be continually and algorithmically disrupted by the superimposition of background color line segments that occlude a set percentage of the length of the line segments forming the characters in the display. The subject 192 may be asked to follow the letter sets using the cursor 1050 during the continuous movement of the letter sets around the around the edge of circular stimulus area 1446.

The letter sets in the array may drift in unison around the display circle or may emerge and fade to take-up new positions on the screen with a full field random cycle length in a settable range, which may be typically thirty six to one-hundred eight frames at seventy-two hertz with emergence and fading each occurring over three frames. The position and continuity of the letter sets may be subjected to the algorithmic control of the stimulus generator 450. Each position shift may trigger the transition of all character sets to other specific example of each set type in the corresponding relative positions.

In an alternate embodiment of the intermediate phase of the letter identification latency module 1460, a word may be made of correct letters imbedded within the stimulus area 199, which may be a ring, with other similar length, correct letter, non-words. All of the three-letter items may drift around the ring in unison. The subject 192 may move the cursor 1050 to the real word and follow it for a predetermined time period or a predetermined angular degrees of drift. The score may be derived from the time it takes the subject 192 to register the location of the real word that may be captured and tracked.

In yet another embodiment of the intermediate phase of the letter identification latency module 1460, correct letter words may be imbedded in the stimulus area 199, which may be a ring, with other similar length, correct letter, non-words. All of the three-letter items my drift around the ring in unison. The content of the ring, which may refer to its real words and non-words, my change regularly as the content drifts so there is always a wedge, which may be a ring segment, containing real words and the remainder of the ring contains non-words. Further, as the subject 192 moves the cursor 1050 to the real word and follows it for some predetermined time period or a predetermined angular degrees of drift, the saliency of all of the letters of the words and non-words may be slowly decreased. The saliency may be decreased either by crossing-out parts of all of the letters with a background colored set of thin lines, or by rotating the individual letters, or by covering the ring with flickering letter-colored dots. The subject 192 may continue to find the real words as algorithmic adjusting of the saliency determines that subject's threshold saliency. The score is derived from the saliency level as described for the other tests of the present disclosure.

Figure 48:
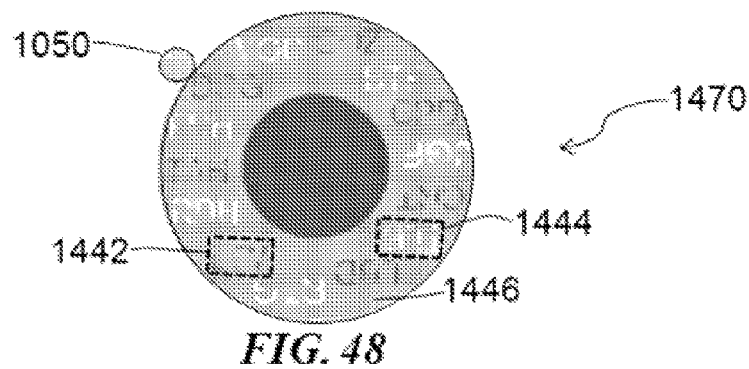
FIG. 48 shows the termination phase of the word recognition module.

FIG. 48 shows the termination phase of the letter identification latency module 1470, during which an approximate threshold may be defined. There remains continuous movement of the target character set and subject tracking during continuous varying of the continuity and exchange of all character sets across cycles towards the end of intermediate phase of the letter identification latency module 1460.

Later, during the termination phase of the letter identification latency module 1470, while in discontinuous movement, the target segment may fade to the background parameters and then may emerge at a new location where it may undergo increasing continuity until the subject's cursor may enter the target segment area. Immediately thereafter, there may be an instantaneous bright flash and beep. Subsequent iterations of this trial may yield a refined threshold.

Figures 49, 50:
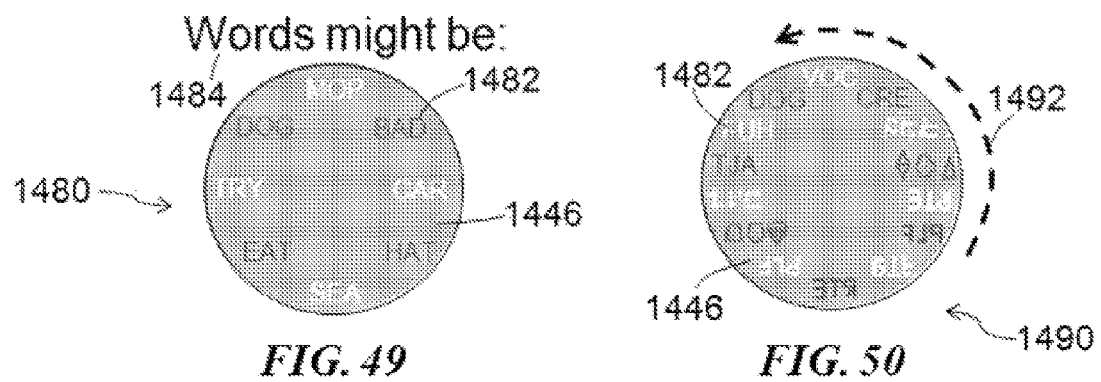
FIG. 49 illustrates the starting phase of the verbal memory module.
FIG. 50 displays the intermediate phase of the verbal memory module.

FIG. 49 illustrates the starting phase of the verbal memory module 1480. This test paradigm may present a series of words 1482 in a list to be memorized. The sample consists of a series of words 1482 that may be arranged around the edge of the stimulus area 199 and headed by the label "Words might be" 1484. The sample words are positioned at selected locations with selected light and dark luminances. During the starting phase of the verbal memory module 1480, the subject 192 may be presented a predetermined series of short words, each with a predetermined number of letters in a set sequence.

FIG. 50 displays the intermediate phase of the verbal memory module 1490. The subject 192 may track the target word in the series of words 1482, starting form low saliency and successively becoming more salient, via the presentation of sample and match across contrast stimuli 1492. A particular word in a series of words 1482 may be presented one-at-a-time along with words not on the list. In other words, in this series of stimuli, the word target may be either sample words or not.

During the intermediate phase of the verbal memory module 1490, the subject 192 may be first shown a series of ten high contrast black or white words for a pre-set adjustable time period, which may be for five seconds. The subject 192 may then be shown a series of the same type of stimuli that may have been used in the starting phase of the letter identification latency module 1440 as was shown in FIG. 43. The presentation of sample and match across contrast stimuli 1492, which may be implemented in the intermediate phase of the verbal memory module 1490, may be the same fade-jump-emerge contrast modulation sequence that may have been used in the intermediate phase of the letter identification latency module 1460.

In an alternate embodiment of the intermediate phase of the verbal memory module 1490, the target word from a predetermined ordered list may be presented at very low saliency after each presentation of a predetermined series of short words. That target word from a predetermined ordered list may drift around the stimulus ring imbedded in with other drifting three-letter sets that are not words. While the subject 192 remains off target, the saliency of the word and the three letter non-words may slowly increase until the word is recognizable as the only word on the screen. The subject 192 may move the cursor 1050, which may be a ball-stick cursor, to the target word and follow it for some predetermined time period or a predetermined degrees of angular movement to register correct acquisition. When the subject 192 has correctly identified the target word, the score for that trial is recorded as the current saliency level. Then, the next word from the list may be imbedded in a new set of three letter non-words at very low saliency and the task continues. The cycle of first viewing the list presentation of these predetermined list of words and then testing on finding the words at the lowest saliency possible may be repeated three times. Scoring of the test may include the number of words correctly acquired, the saliency level at which they were acquired, and the slope of the average saliency levels across the three repetitions of the task.

In yet another embodiment of the intermediate phase of the verbal memory module 1490, only one target word may be implemented. In this exemplary embodiment, after the saliency score is calculated, the number of target words may be slowly increased to repeatedly derive that subject's saliency threshold as the word list length increases. If one knows the word one is looking for, then it may be relatively easy to find it; however, the degree of difficulty may increase with an increase in the number of words. Each subject 192 may have a function of saliency versus list length and that may be a measure of verbal memory's ability to enhance word recognition.

In an alternate embodiment of the intermediate phase of the verbal memory module 1490, may include, but is not limited to, a ring with only correct letter words. As the subject 192 correctly follows the initially single word around the ring, another word will be added and the subject 192 may shift to following the new word. Throughout the test, new words may be added and may be monitored for how long it takes the subject 192 to identify and shift to the new word most recently added to the subject display 198. Scoring may be accomplished by measuring the new word identification latency, as a function of the total number of words in the display during that response.

Figure 51:
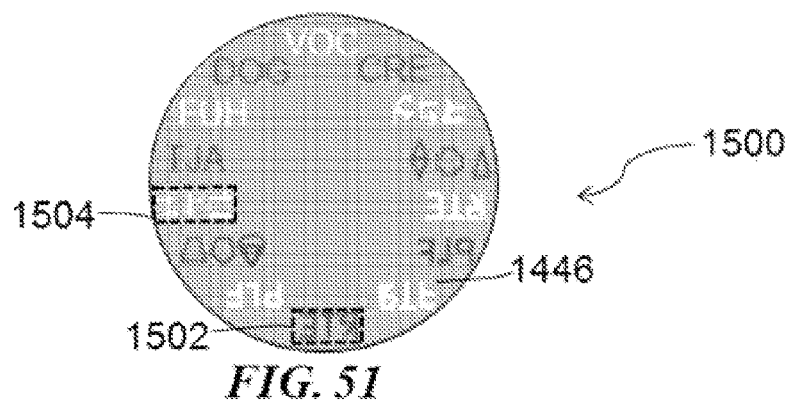
FIG. 51 illustrates the left-up target orientation with high contrast.
Figure 52:
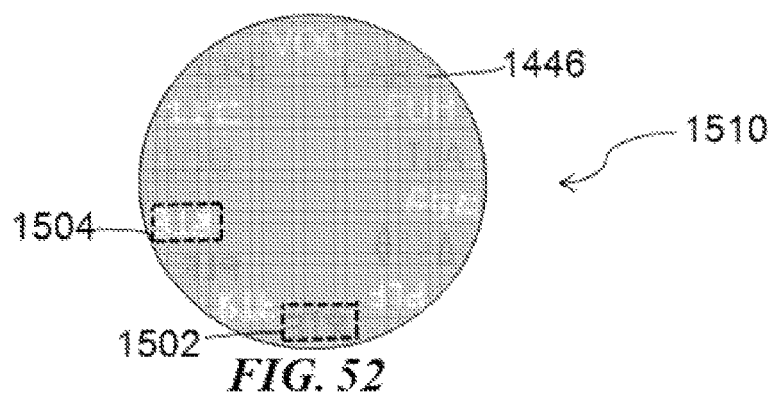
FIG. 52 shows the right-up target orientation with moderate contrast.
Figure 53:
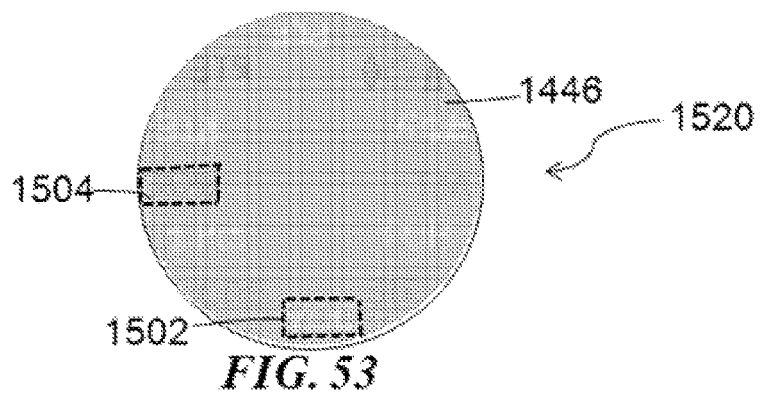
FIG. 53 displays the right-down target orientation with low contrast.

The responses to the stimuli from the intermediate phase of the verbal memory module 1490 may be used to establish response dynamics in the stimulus contrast domain and the kinematics domain. During the intermediate phase of the verbal memory module 1490, the target orientation may be placed towards the left or towards the right of the stimulus area 199, and may be either high, moderate, or low contrast. FIGS. 51, 52, and 53 show the various placement configurations and contrast conditions that may be implemented during the intermediate phase of the verbal memory module 1490.

With reference to FIGS. 51, 52, and 53, equal numbers of alternating black-colored symbol sets 1502 and white-colored symbol sets 1504 may be presented in a fixed sequence around the edge of circular stimulus area 1446. The three letters symbol sets may be distributed in the background that may comprise a cluster of other three letter symbol sets and also a real word that defines the target.

The three symbols for the alternating black-colored symbol sets 1502 and white-colored symbol sets 1504 may include, but are not limited to, symbols, target words, legal-non-words, illegal non-words, flipped illegal non-words, flipped and rotated non-words. Further, the three letters symbol sets may be in any orientation. Further, the font, size, and position of the black-colored symbol sets 1502 and white-colored letter symbol sets 1504 may be determined by the pre-sets from the starting phase of the visual motion discrimination test 1350 and the starting phase of the visual form discrimination test 1330. The contrast of the black-colored symbol sets 1502 and white-colored letter symbol sets 1504 may be set at being two confidence intervals above the subject's contrast threshold obtained in the termination phase of the visual motion discrimination test 1370.

More particularly, FIG. 51 illustrates the left-up target orientation with black-colored symbol sets 1502 and white-colored symbol sets 1504 in high contrast. FIG. 52 shows the right-up target orientation with black-colored symbol sets 1502 and white-colored symbol sets 1504 in moderate contrast. FIG. 53 displays the right-down target orientation with black-colored symbol sets 1502 and white-colored symbol sets 1504 in low contrast.

Figure 54:
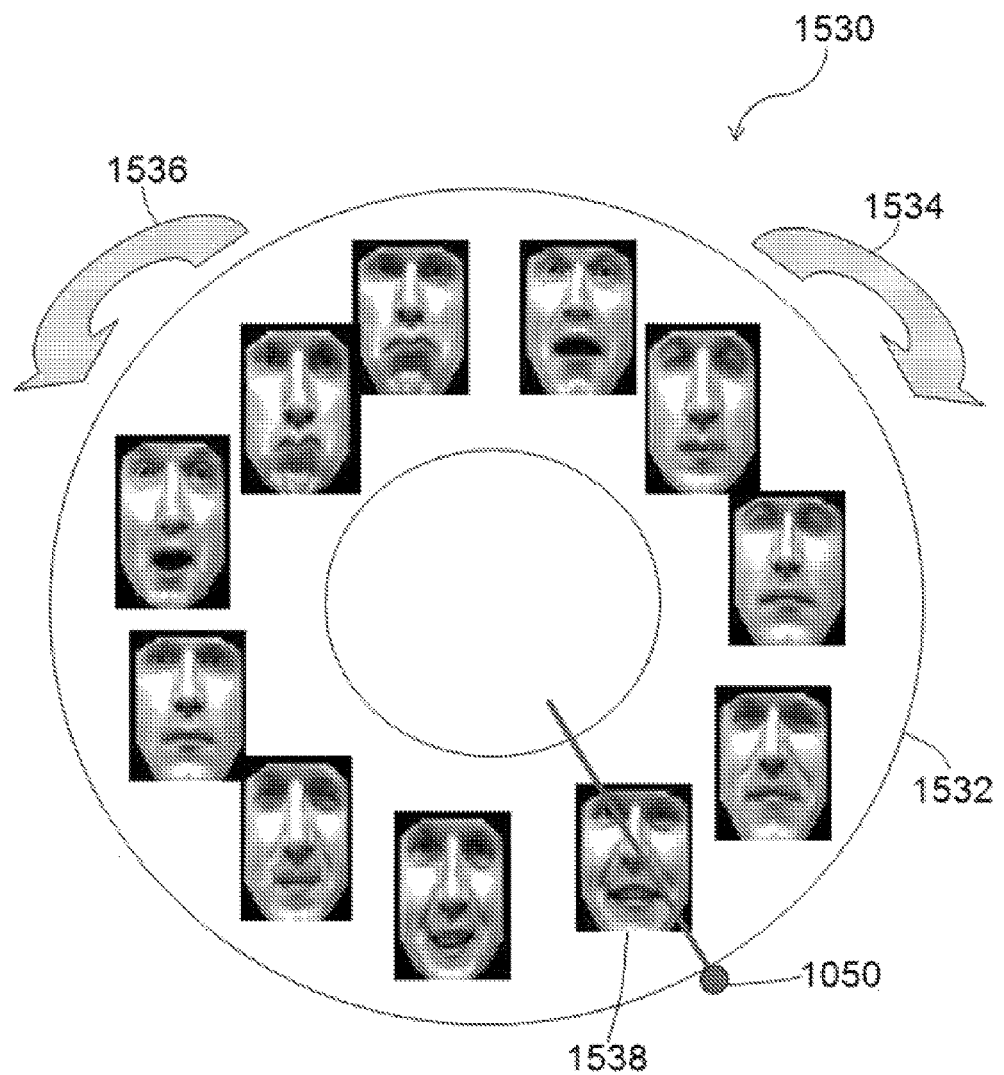
FIG. 54 shows a low difficulty facial emotion sensitivity test.
Figure 55:
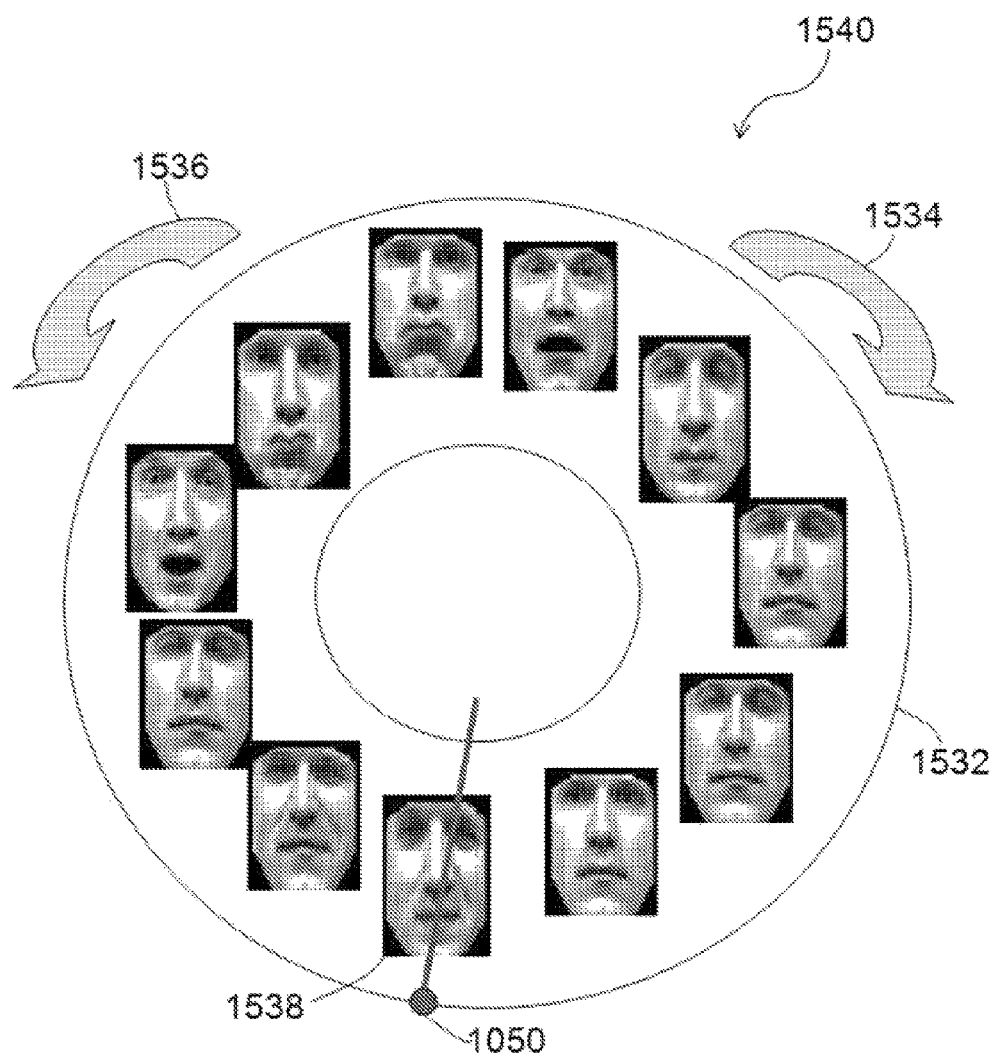
FIG. 55 shows a moderate difficulty facial emotion sensitivity test.
Figure 56:
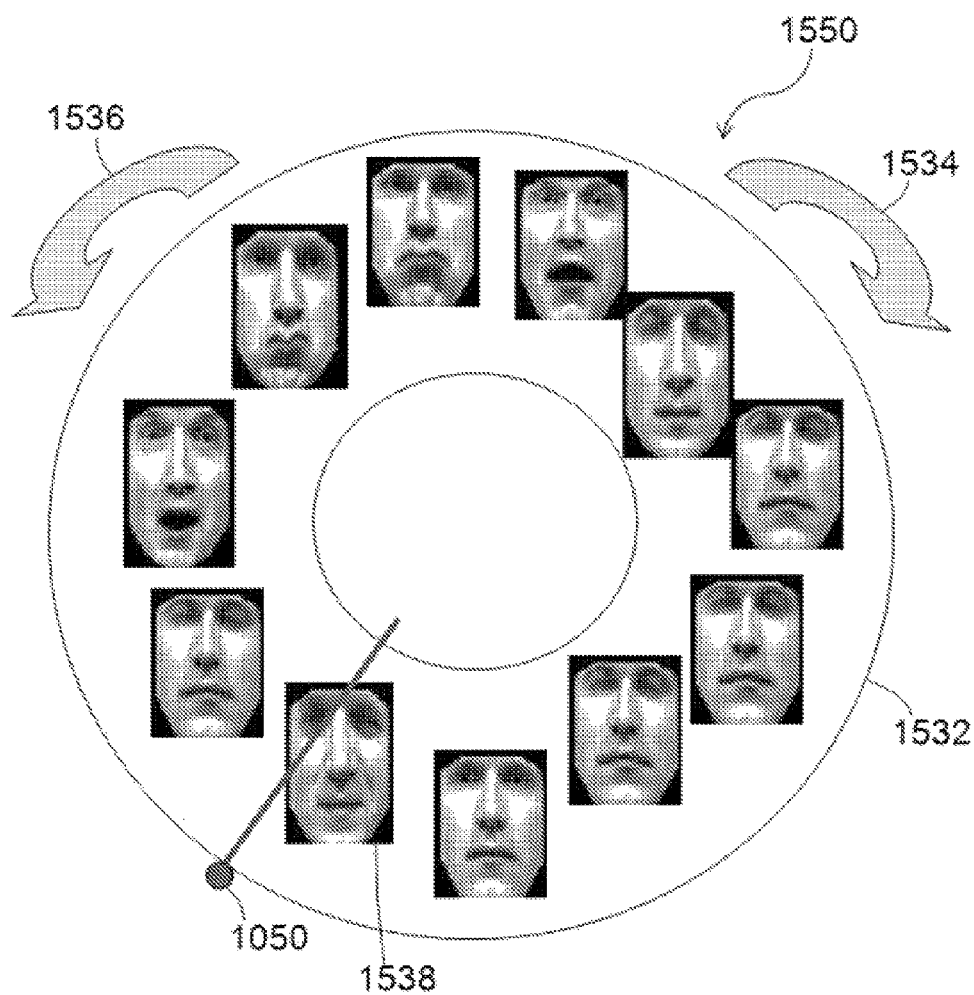
FIG. 56 shows a high difficulty facial emotion sensitivity test.

With reference to FIGS. 54, 55, and 56, facial emotion sensitivity tests may be presented to the subject 192. More particularly, FIG. 54 shows a low difficulty facial emotion sensitivity test 1530, FIG. 55 shows a moderate difficulty facial emotion sensitivity test 1540, and FIG. 56 shows a high difficulty facial emotion sensitivity test 1550, for any of which a display of faces 1532 may be presented to the subject 192. A plurality of faces, may be all of the same person or may be a pseudo-person composite of other faces.

Subsequently, the affective emotion may be modulated, such as from grimace or frown to a wide-eyed or smile emotion. There may be a gradient of emotion expressions distributed across the faces, from happy faces at one point to sad faces one hundred eighty degrees from that point. The subject 192 may locate and may track the happiest face or the saddest face. The subject 192 may be asked to use the subject manipulandum 1402 to point to the happier faces as the differences between the happier and sadder faces may be narrowed with good performance or widened with poor performance. The subject 192 may demonstrate a minimal difference in affective expression required for their identifying the most positive or happy expression. The subject 192 may use the rotatory manipulandum 414 to rotate and to align the cursor 1050 to the happiest face 1538 as the range from sad to happy is increased, thereby making task easier, or decreased, thereby making task harder. The subject 192 may rotate the rotatory manipulandum 414 in a clockwise rotation 1534 or in a counterclockwise rotation 1536.

The algorithm associated with the present disclosure may alter the range of faces, which may be from very happy to very sad. The algorithm associated with the present disclosure may alter the range of faces, which may be slightly happy to slightly sad. The mid-point may be from happy to neutral, or in an alternative embodiment may be from neutral to sad. Further, the algorithm associated with the present disclosure may be easy or difficult. Further, the subject's score may be a reflection of the minimal range, which may be of greatest difficulty, at which the subject 192 may accurately locate and track the target.

The low difficulty facial emotion sensitivity test 1530, moderate difficulty facial emotion sensitivity test 1540, and high difficulty facial emotion sensitivity test 1550 differ in the level of difficulty within each test. Further, the low difficulty facial emotion sensitivity test 1530, moderate difficulty facial emotion sensitivity test 1540, and high difficulty facial emotion sensitivity test 1550 may help determine the test subject's perceptual threshold range scored relative to a normal range derived from comparison subject groups. Facial gender, age, and identity may be randomly shifted during intervals of the test session. Future known equivalents of the low difficulty facial emotion sensitivity test 1530, moderate difficulty facial emotion sensitivity test 1540, and high difficulty facial emotion sensitivity test 1550 may use only one gender, age, etc. facial identity group or can use alternative target, which may include, but is not limited to, the saddest face.

Figure 57:
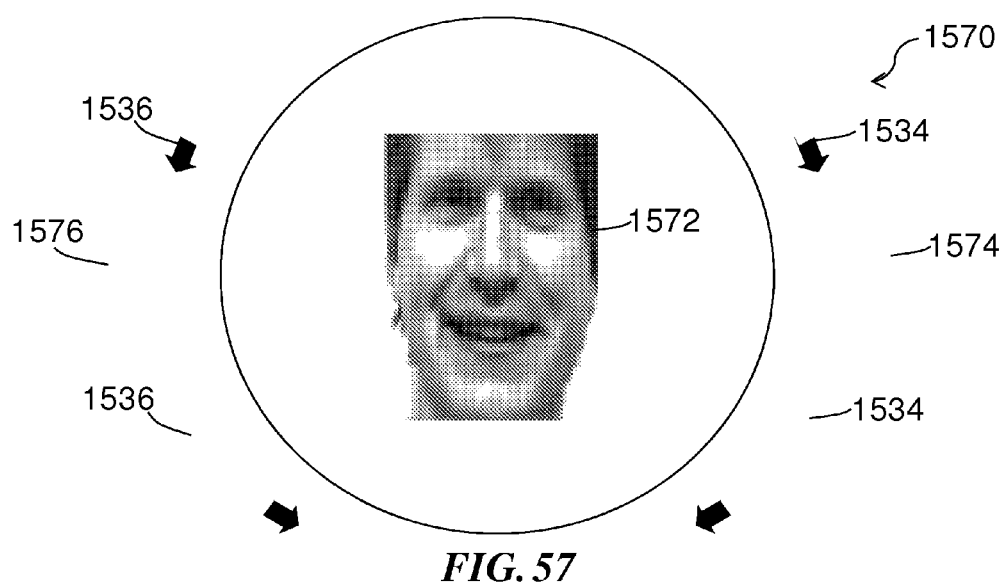
FIG. 57 shows a low difficulty facial emotion nulling test.
Figure 58:
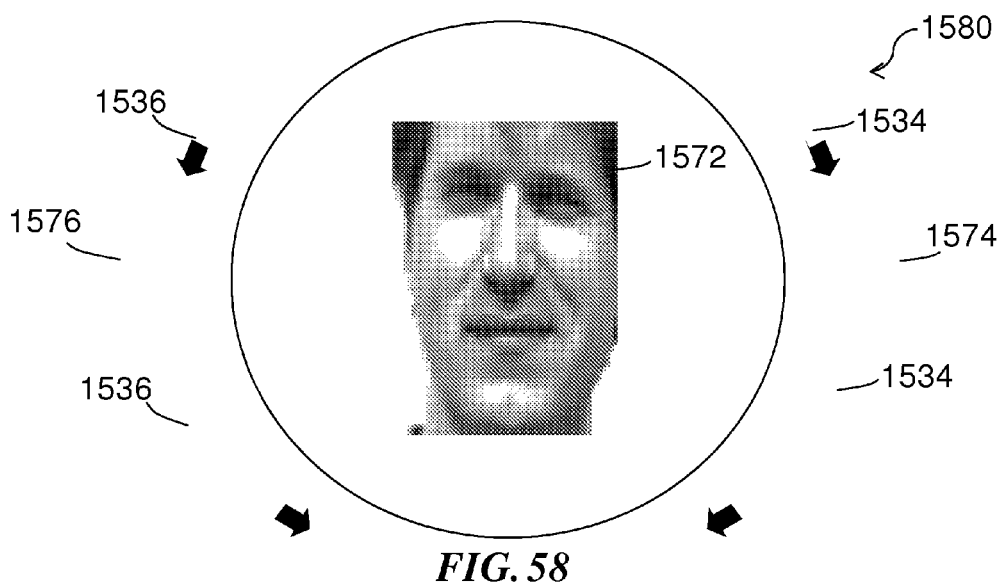
FIG. 58 shows a moderate difficulty facial emotion nulling test.
Figure 59:
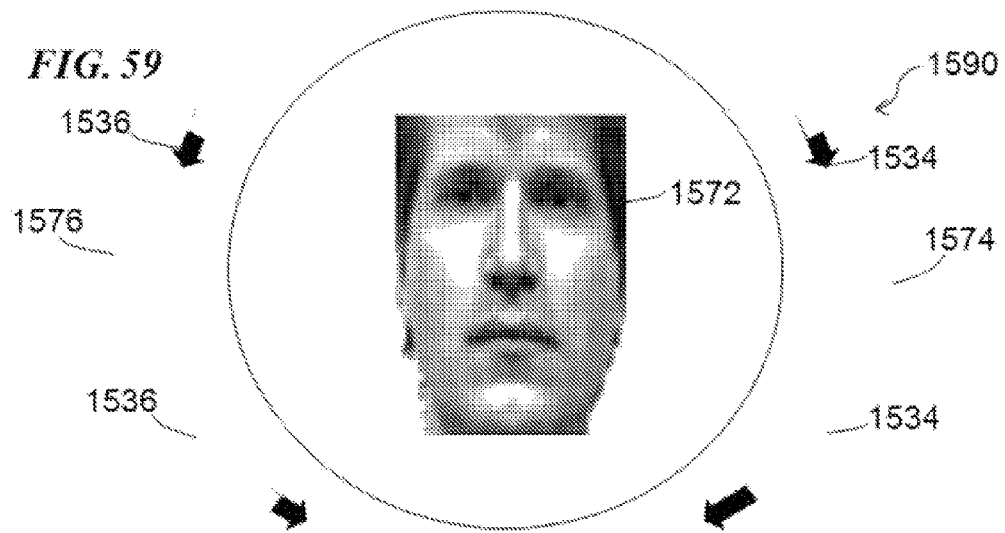
FIG. 59 shows a high difficulty facial emotion nulling test.

With reference to FIGS. 57, 58, and 59, facial emotion nulling tests may be presented to the subject 192. More particularly, FIG. 57 shows a low difficulty facial emotion nulling test 1570, FIG. 58 shows a moderate difficulty facial emotion nulling test 1580, and FIG. 59 shows a high difficulty facial emotion nulling test 1590, for any of which a display of a particular facial expression 1572 is presented to the subject 192.

During either the low difficulty facial emotion nulling test 1570, moderate difficulty facial emotion nulling test 1580, or a high difficulty facial emotion nulling test 1590, a single image of a same gender face is presented and the system varies the affective expression of the face from a sadder to a happier expression and vice-a-versa.

The emotional expression of the single face may be varied as described in the low difficulty facial emotion sensitivity test 1530, moderate difficulty facial emotion sensitivity test 1540, and high difficulty facial emotion sensitivity test 1550. During either the low difficulty facial emotion nulling test 1570, moderate difficulty facial emotion nulling test 1580, or a high difficulty facial emotion nulling test 1590, the subject 192 may uses the subject manipulandum 402 to make the face appear neutral, which may refer to being neither happy nor sad. The subject 192 may be asked to rotate the rotary manipulandum 414 with counter-clockwise rotation 1534, thereby making the expression sadder with the use of the turn to make sadder feature 1576, or with clockwise rotation, thereby making the expression happier with the use of the turn to make happier feature 1574.

The goal of the subject 192 may be to continue to rotate the rotary manipulandum 414 to make the expression neutral as the present disclosure makes sustained changes in the affective expression of the facial display. The subject 192 may use the rotatory manipulandum 414 to morphologically transform facial expression across the spectrum from sadder, which may be through repeated counterclockwise rotation 1536, to happier, which may be through repeated clockwise rotation 1534, to keep the facial expression neutral.

The algorithm of the present disclosure may continually shift the emotional content of the facial expression and the subject 192 may have to change it back toward neutral. Such a test may be associated with being a nulling task, wherein only the parameter is changed, and the subject 192 has to perceive the direction and magnitude of the change and set it back to where it was. The scoring may reflect the magnitude of change required to trigger the subject's response, the point called neutral from happy and the point called neutral from sad.

The low difficulty facial emotion nulling test 1570, moderate difficulty facial emotion nulling test 1580, or a high difficulty facial emotion nulling test 1590 each may be sixty to one-hundred eighty seconds in duration. The system repeatedly may drift the facial expression to a sadder or to a happier condition as the subject 192 may try to null that effect and may try maintain a neutral expression on the display. The system may use an adaptive staircase protocol to determine the smallest perturbation of facial expression that may provoke an appropriate counter-response from the test subject 192 as a facial expression perceptual threshold, which may be scored relative to normal range identifiable by others in the comparison subject group.

Facial gender, age, and identity may be randomly shifted during intervals of the test session. Future known equivalents of the low difficulty facial emotion nulling test 1570, moderate difficulty facial emotion nulling test 1580, or a high difficulty facial emotion nulling test 1590 may use only one gender, age, etc.

Further, the low difficulty facial emotion nulling test 1570, moderate difficulty facial emotion nulling test 1580, or a high difficulty facial emotion nulling test 1590 each differ in the level of difficulty within each test.

Figure 60:
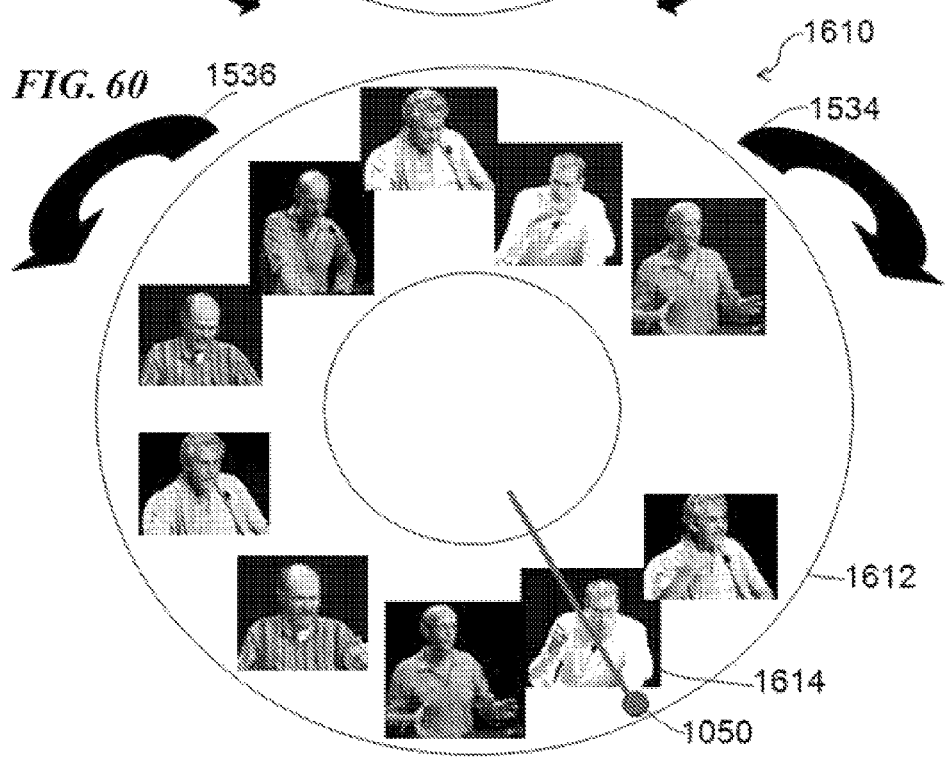
FIG. 60 illustrates the low difficulty social cues sensitivity test.
Figure 61:
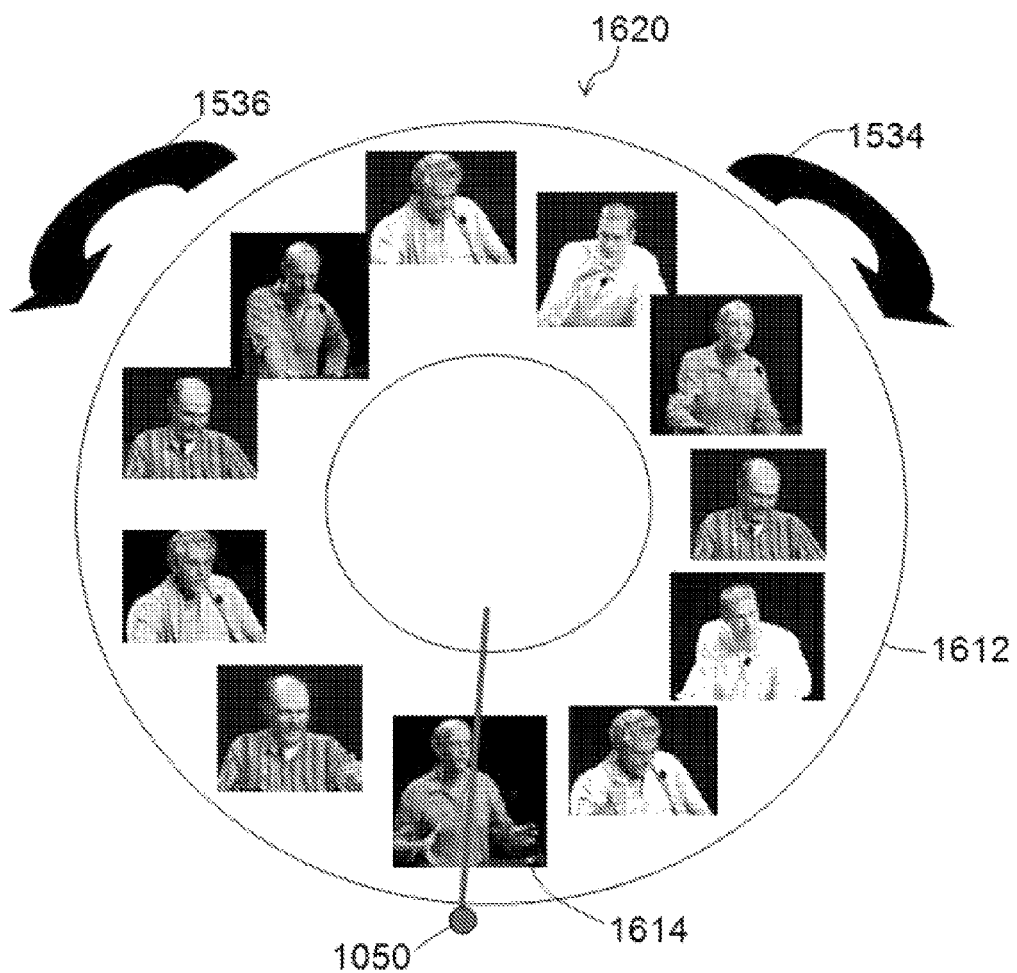
FIG. 61 illustrates the moderate difficulty social cues sensitivity test.
Figure 62:
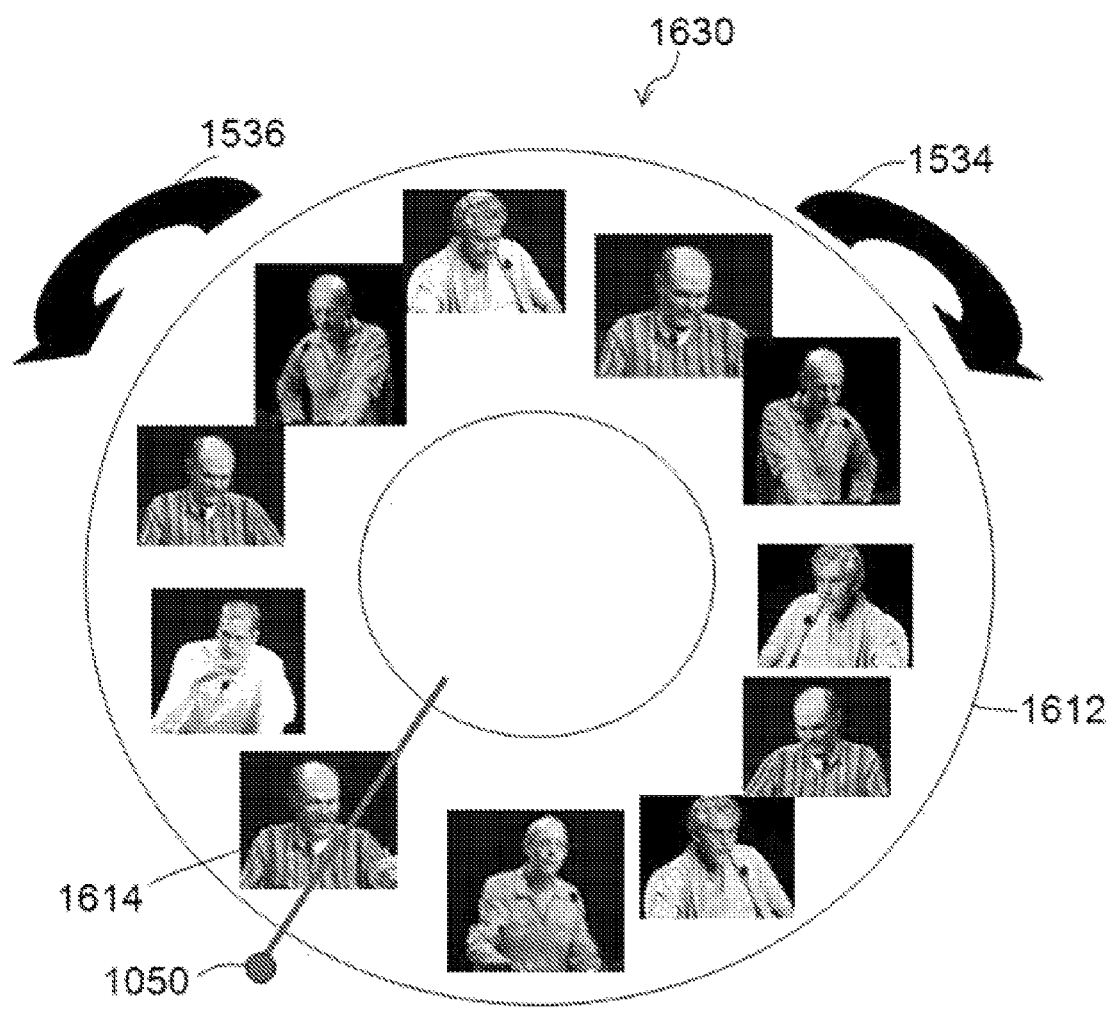
FIG. 62 illustrates the high difficulty social cues sensitivity test.

With reference to FIGS. 60, 61, and 62, social cues sensitivity tests may be presented to the subject 192. More particularly, FIG. 60 illustrates the low difficulty social cues sensitivity test 1610, FIG. 61 illustrates the moderate difficulty social cues sensitivity test 1620, and FIG. 62 illustrates the high difficulty social cues sensitivity test 1630, for each of which a display of varying aggressiveness levels 1612 may be presented to the subject.

In one embodiment, the display of varying aggressiveness levels 1612 may show a number of whole body images of different persons. The subject 192 may use the rotatory manipulandum 414 to align the cursor 1050 to the image of the person being most aggressive, herein called the most aggressive person 1614. The subject 192 may rotate the rotatory manipulandum 414 in a clockwise rotation 1534 or in a counterclockwise rotation 1536 to indicate the most aggressive person 1614 on the display of varying aggressiveness levels 1612. As the range from submissive to aggressive is increased, thereby making the task easier, or decreased, thereby making the task harder, the perceptual threshold of the subject 192 relative to a normal range may be characterized in comparison.

In an alternate embodiment, a variety of different body positional attributes may be displayed. For example, the body positional attribute may be associated with the most/least worried or the most/least frightened or the most/least leadership ability or the most/least assertive. The body positional attribute of least worried may be associated with, but is not limited to, smiling, titled head and shoulders, and hands at the side. The body positional attribute of most worried may be associated with, but is not limited to, pursed-lips, slouched head and shoulders, and hands tightly clasped in front of the lower face. The body positional attribute of most frightened may be associated with, but is not limited to, eyes bulging, limbs flexed, and jerky movements. The body positional attribute of least frightened may be associated with, but is not limited to, smiling, upright, and slow movements.

Person gender, age, and identity may be randomly shifted during intervals of the test session for any or all of the low difficulty social cues sensitivity test 1610, the moderate difficulty social cues sensitivity test 1620, or the high difficulty social cues sensitivity test 1630. Future known equivalents of any or all of the low difficulty social cues sensitivity test 1610, the moderate difficulty social cues sensitivity test 1620, or the high difficulty social cues sensitivity test 1630 may use only one gender, age, etc. postural identity group or can use alternative target features, which may include, but is not limited to, the most submissive person.

Further, the low difficulty social cues sensitivity test 1610, the moderate difficulty social cues sensitivity test 1620, or the high difficulty social cues sensitivity test 1630 may also consider the interactions between the persons depicted in the display of varying aggressiveness levels 1612 such that the subject 192 indicates who may be the most likely to be leader of the group. The subject 192 may change the cursor 1050 to indicate who they see as the likely leader with differences between target leaders' traits and those of the person least likely to assume leadership are successively changed.

Further, the low difficulty social cues sensitivity test 1610, the moderate difficulty social cues sensitivity test 1620, or the high difficulty social cues sensitivity test 1630 each differ in the level of difficulty within each test.

In an alternative embodiment of social perception domain testing, nulling adjustments may be evaluated in the social interactions nulling test, which may include, but is not limited to, a full body representation of two people standing side-by-side in an ongoing social interaction. One person may stand on the left side and another person may stand on the right side. One person may be a man, and the other person may be a woman; alternatively, both persons may be of the same sex. Further, one person may be of a particular ethnic background; another person may be of a different ethnic background; alternatively, both persons may be of the same ethnic background. During social interactions nulling testing, postures, facial expressions, and/or gestures may be distinctive among the two people; however, the two persons may not interact with words. The subject 192 may be instructed to adjust the left or right person to make one more dominant and the algorithm will change the balance, thereby making nulling adjustments.

Figure 63:
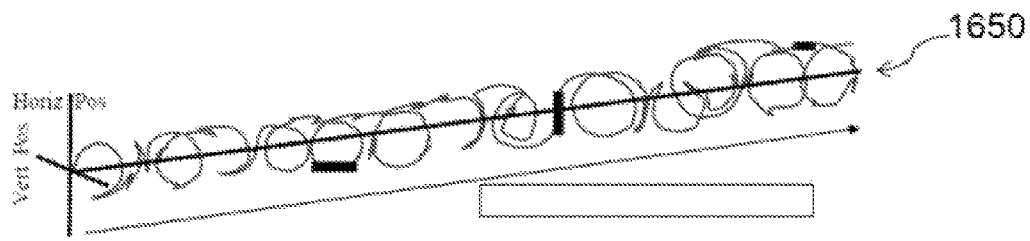
FIG. 63 shows an exemplary position trace.
Figure 64:
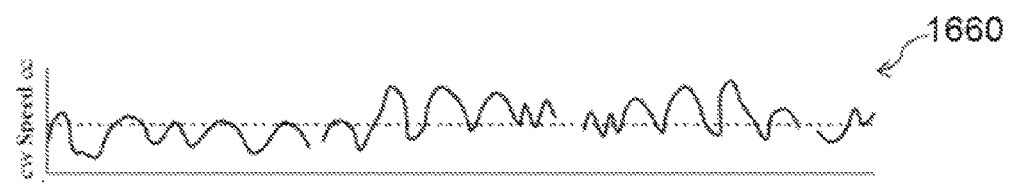
FIG. 64 illustrates an exemplary speed trace.
Figure 65:
FIG. 65 depicts an exemplary acceleration trace.

With reference to FIGS. 63, 64, and 65, typical target traces are presented, which may be, but are not limited to, sixty seconds traces. FIG. 63 shows an exemplary position trace 1650. FIG. 64 illustrates an exemplary speed trace 1660. FIG. 65 depicts an exemplary acceleration trace 1670.

The exemplary position trace 1650, the exemplary speed trace 1660, and the exemplary acceleration trace 1670 may show the target location, which may be driven in a tracking fashion by the stimulus generator 450 or in discontinuous fashion by jumping movements. Further, the exemplary position trace 1650, the exemplary speed trace 1660, and the exemplary acceleration trace 1670 may show initially, the highest signal-to-noise stimuli that may trigger the subject capture, which may refer to the positioning near the center of the highest signal-to-noise segment.

The exemplary tests of the present disclosure capture may be followed by irregular tracking movements with graded signal-to-noise fade-emerge cycles that may trigger capture cycles. Further, the exemplary tests of the present disclosure capture may include increasing, then decreasing, position and velocity error. During the exemplary tests of the present disclosure, escape, which may refer to gradually increasing error, may trigger either: 1) fixed-position re-emergence to trigger re-capture and then continuing movement, or 2) full-fading, jump to a new site, and re-emergence there until re-capture triggers new tracking movements. Further, uniformity of the distribution of capture position may be assisted by jumps and movement parameters may during signal-to-noise (S/N) fading cycles that may be based on subject error.

Figure 66:
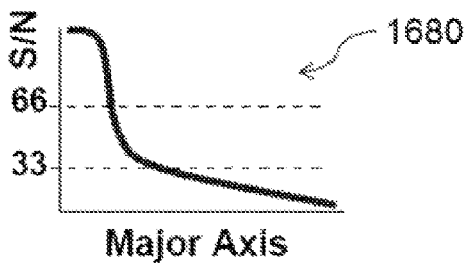
FIG. 66 displays an exemplary 3D S/N Gradient.

With reference to FIG. 66, an exemplary 3D S/N Gradient 1680, wherein S/N may refer to signal-to-noise ration, is presented. The exemplary 3D S/N Gradient 1680 may be representative of being across all stimulus domains. The exemplary tests of the present disclosure may be implemented to achieve a three-fold signal-to-noise gradient. More particularly, during the exemplary tests of the present disclosure, from the point furthest from the target in the stimulus area 199, there may be a gradual increase to one-third of the current peak signal-to-noise ratio at the edges of the target segment, which may be a thirty degrees segment. Further, another one-third signal-to-noise ratio increase may extend from the thirty degrees edges to a ten degrees segment in the stimulus area 199. The exemplary tests of the present disclosure may be structured such that the peak signal-to-noise should extend uniformly across the ten degrees segment, which may result in the hypothetical 3D S/N Gradient 1680.

Figure 67:
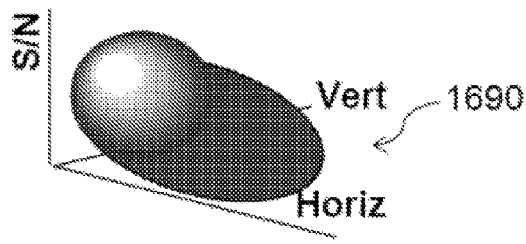
FIG. 67 portrays an exemplary S/N profile with respect to vertical and horizontal positions.

With reference to FIG. 67 an exemplary S/N profile 1690 with respect to vertical and horizontal positions is presented. The an exemplary S/N profile 1690 may be reflective of subject 192 response analyses that indicate the subject 192 may accurately track to yield reliable performance across all domains. Such reliable performance may be achieved via following of recommendations, which may be, but is not limited to:

i) The first stimulus cycles of each test of the present disclosure may be at low motion parameters and high signal-to-noise ratios so that the subject 192 may understand the task.

ii) Motor performance may be established by imposing a series of movement acceleration-deceleration cycles or direction reversal cycles in at least two of the four quadrants of the hypothetical S/N profile 1690.

iii) Subsequent cycles may include cue fading, which may result from decreasing the signal-to-noise ratio, such that when the cue escapes, the motion may slow in order to see whether the subject 192 may reduce the error distance. If the subject 192 catches-up, then the slower speed may become the new base speed. However, if error reduction does not occur, then the target slows down to a stop and the signal-to-noise ratio is increased until re-capture triggers the resumption of movement.

iv) There may be a jump to a new position near the current response position by slowly increasing the signal-to-noise ratio.

v) Repeated test cycles may be used to refine the impression of the signal-to-noise threshold and fastest speed and acceleration that the subject may accurately track to yield reliable performance across all conditions.

Figure 68:
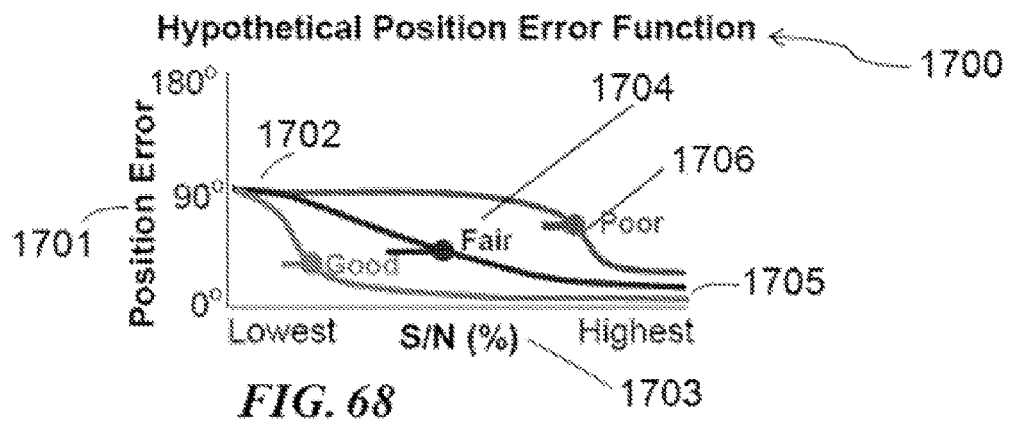
FIG. 68 shows an exemplary position error function profile.

FIG. 68 shows an exemplary position error function profile 1700, which may be a plot of error by signal-to-noise to describe the performance of the subject 192. A graph of the position error axis 1701 versus the signal-to-noise percentage axis 1703 that may be present in the position error function profile 1700. The position error maximum 1702 and the position error minimum 1705 may be asymptotic projections, which may capture the best and the worst performance of the subject 192. The position error peak slope 1706 may be the mid point in the range of plus or minus five percent of the highest slope. The position error area 1704 under the curve of the position error function profile 1700 may describe the overall performance of the subject 192. Further, the position error function profile 1700 may be qualitatively grouped into profiles based on degree of differences, such as being good, fair, and poor.

Figure 69:
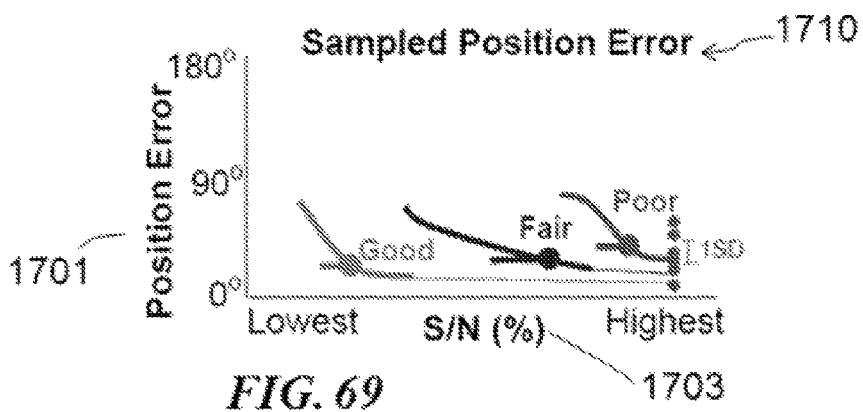
FIG. 69 shows an exemplary sampled position error function profile.

FIG. 69 shows an exemplary sampled position error function profile 1710, which may be a plot of the position error axis 1701 versus the signal-to-noise percentage axis 1703, on a sampled basis. The exemplary sampled position error function profile 1710 may be based on a threshold and a variance measure from the tests of the present disclosure. For instance, in the visual motion discrimination test, which is further described in FIGS. 34, 35, and 36, the threshold is taken to be the signal-to-noise ratio under the point on the sampled position error function profile 1710 that is two position error significant digits back on along the sampled position error function profile 1710 curve. The present disclosure may utilize the range of the signal-to-noise covered by the two position error significant digit steps as a variance measures. The measures that may be implemented in the position error function profile 1700 and the sampled position error function profile 1710 may be sensitive to best performance, capture escape variability, and the local slope of the position error curve.

Figure 70:
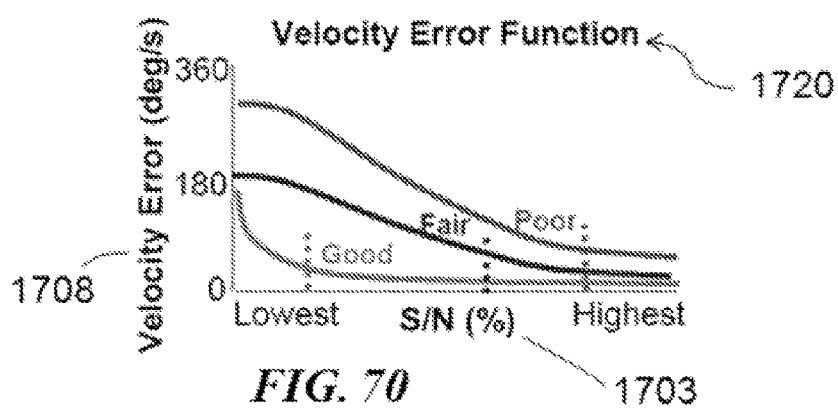
FIG. 70 displays an exemplary velocity error function profile.

FIG. 70 displays an exemplary velocity error function profile 1720, which may be a plot of the velocity error axis 1708 versus the signal-to-noise percentage axis 1703. The velocity error function profile 1720 may show a representation of the difference between the stimulus and the response velocity.

Figure 71:
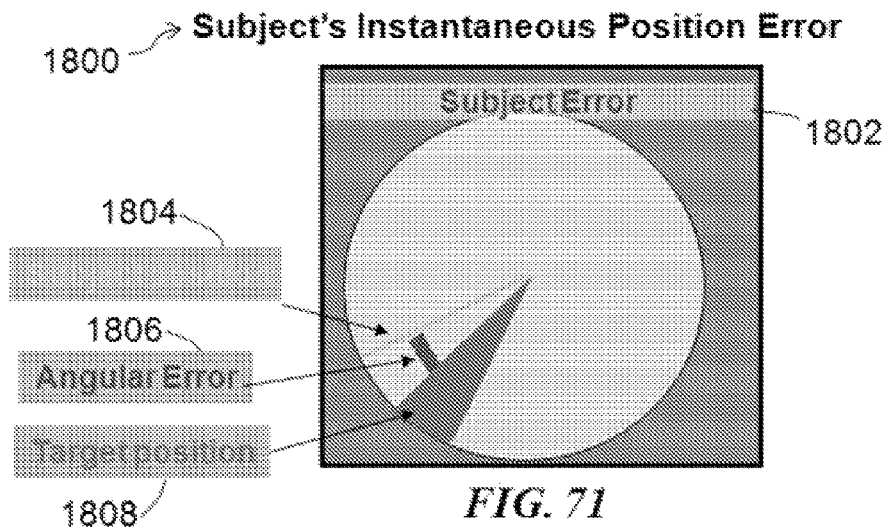
FIG. 71 portrays the instantaneous position error.

FIG. 71 portrays the instantaneous position error 1800 of the subject 192. The subject error 1802 may be a function of the subject position 1804, the angular error 1806, and the target position 1808. The subject error 1802 may be an error in the selection of the target on the stimulus area 199 by the subject 192. The subject position 1804 may be an error in the position of the target on the stimulus area 199 by the subject 192. The angular error 1806 may be an error in the angular position of the target on the stimulus area 199 by the subject 192.

Figure 72:
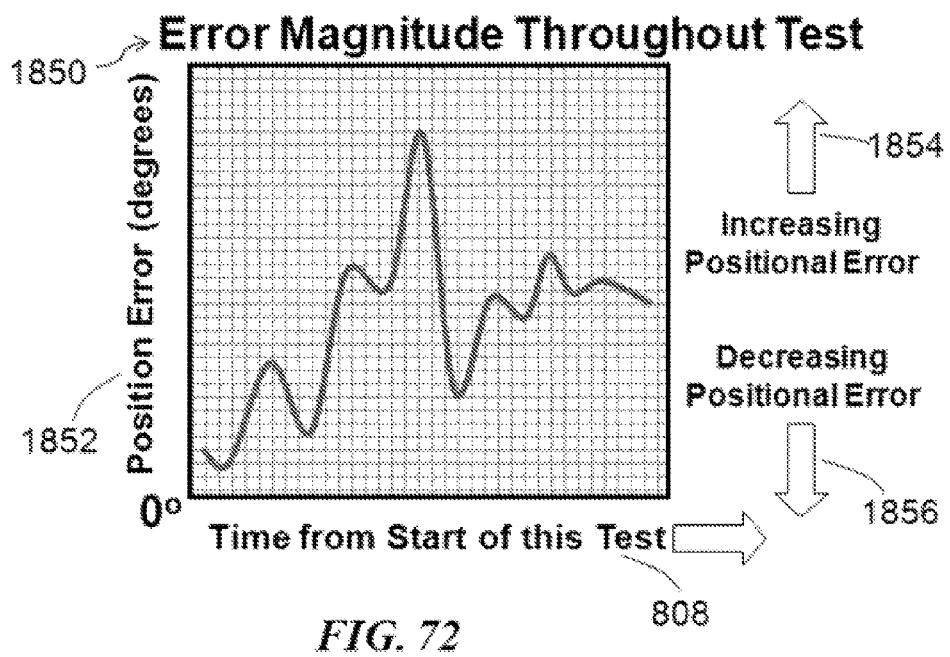
FIG. 72 shows a graphical representation of the error magnitude throughout test.

FIG. 72 shows a graphical representation of the error magnitude throughout test 1850, which may be a plot of the position error in degrees 1852 versus the time from the start of this test 808, which may be represented as ten seconds intervals 806. Further, the graph the error magnitude throughout test 1850 may represent increasing positional error 1854 with a higher value of time from the start of this test 808. Further, the graph the error magnitude throughout test 1850 may represent decreasing positional error 1854 with a lower value of time from the start of this test 808.

Further, the error associated with the error magnitude throughout test 1850 may peak at an escape event, during which a subject 192 may lose track of the target, but may decrease when the subject 192 re-captures the target to successively converge on subject's typical error margin. The error may be signed as being plus or minus one-hundred and eighty degrees relative to the direction of target movement, with the subject 192 being ahead or behind that movement.

Figure 73:
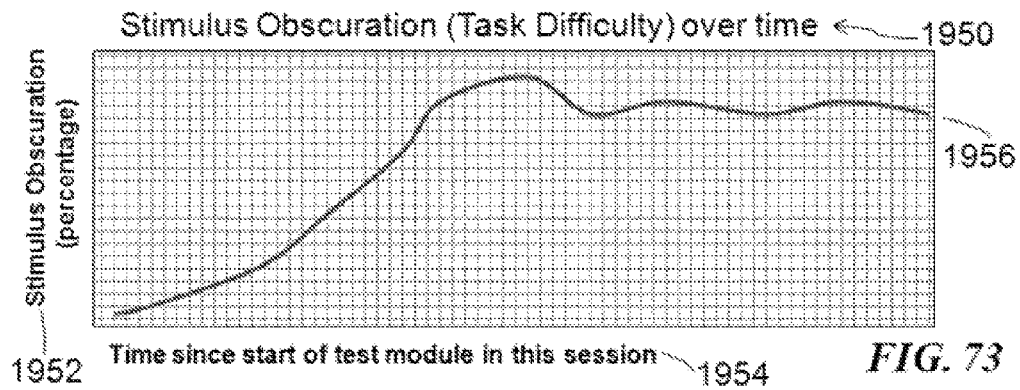
FIG. 73 depicts the stimulus obscuration over time.

FIG. 73 depicts the stimulus obscuration over time 1950, which may refer to the task difficulty over time. More particularly, the graph of stimulus obscuration over time 1956 may be a graph of percentage stimulus obscuration 1952 versus time since start of test module in this session 1954.

Further, the time since start of test module in this session 1954 may be represented, but is not limited to, as being five seconds intervals.

Figure 74:
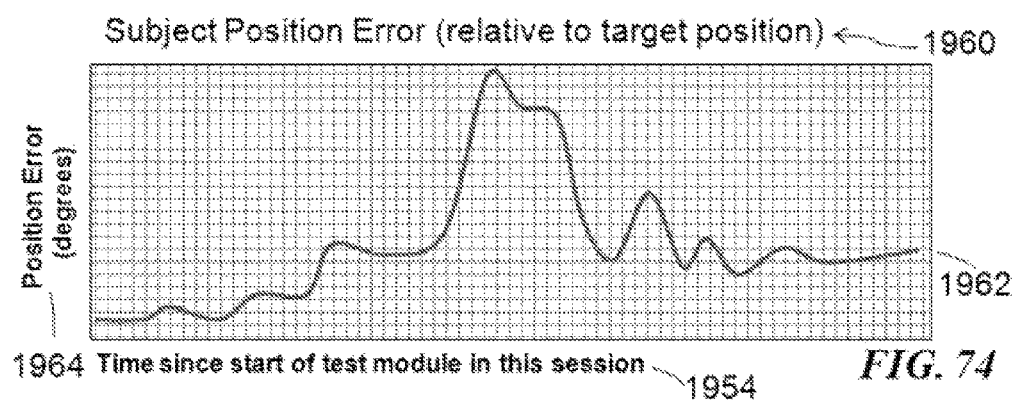
FIG. 74 displays the subject position error relative to target position.

FIG. 74 displays the subject position error relative to target position 1960. The subject position error relative to target position 1960 may be a graph of subject position error over time 1962, which may be represented as a graph of position error in degrees 1964 versus time since start of test module in this session 1954. Further, the time since start of test module in this session 1954 may be represented, but is not limited to, as being five seconds intervals.

Figure 75:
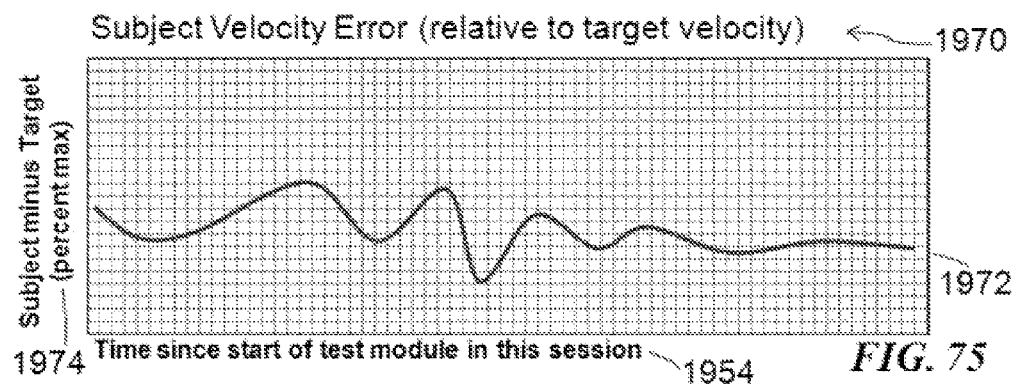
FIG. 75 illustrates depicts the subject velocity error relative to target velocity.

FIG. 75 illustrates depicts the subject velocity error relative to target velocity 1970. More particularly, the graph of subject velocity error relative to target velocity 1972 may be graphically represented as subject minus target as percent maximum 1974 versus time since start of test module in this session 1954. Further, the time since start of test module in this session 1954 may be represented as subject minus target as percent maximum versus but is not limited to, as being five seconds intervals.

Figure 76:
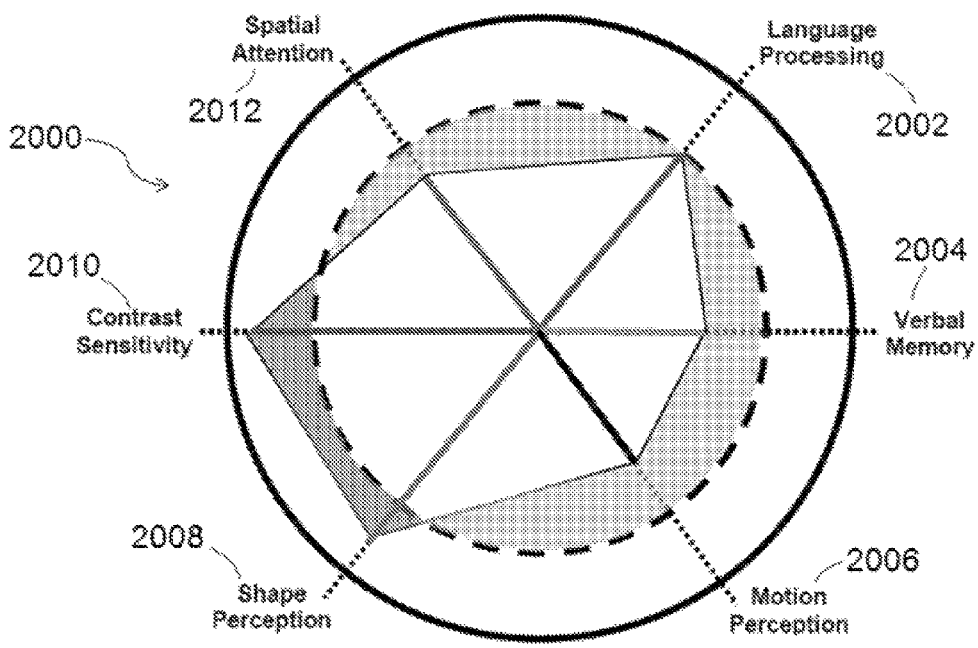
FIG. 76 shows a results summary via a graphical user interface.

FIG. 76 shows a results summary 2000 via a graphical user interface, which may be based on the results from the tests of the present disclosure. The results summary may include, but is not limited to, a representation of the quantitative assessment of language processing 2002, verbal memory 2004, motion perception 2006, shape perception 2008, contrast sensitivity 2010, and spatial attention 2012. The results summary 2000 may aid in determining a quantitative score and interpretation of passing or failing in relation to functional impairment. More particularly, the sensory-motor neurocognitive assessment associated with the results summary 2000 may result in characterization protocols that may yield response functions relating time and saliency that may generate real-time scores based on: the average final saliency score over three periods, the saliency at which the most time may be spent during testing, and the total time that may be spent in the test.

Additional scoring may be achieved off-line and may focus on an algorithmic fit of an asymptotic function to the response function generated in each sensory-motor neurocognitive assessment protocol. This function may then be used to describe performance and generate secondary measures, which may include, but are not limited to: 1) basic measures such as the fit parameters, asymptote and area under the curve, 2) comparative measures as the differences between the basic measures of a subject on a particular sensory-motor neurocognitive assessment protocol and that subject from other selected sensory-motor neurocognitive assessment protocols, 3) comparative measures as the differences between the basic measures of a subject on a test and the measures from a selected group of comparison subjects.

Sensory-motor neurocognitive assessment measures associated with the results summary 2000 may be derived in real-time for each test and may be transformed as standardized scores relative to an age-based comparison group. These standardized scores may be derived separately for each sensory-motor neurocognitive assessment protocol.

Sensory-motor neurocognitive assessment protocol scores associated with the results summary 2000 may be shown on a radial plot, grouped by cognitive relatedness sensory-motor neurocognitive assessments. Differences between age-normal function and a test subject's function may be colored in particular color to indicate sub-normal function and colored in a different color to indicate supernormal function. Differences that may be induced by the negative impact of invalid cues and the positive impact of valid cues may be shown as closely related functions.

Further, differences between a subject's function and age-normal function may be inferred from observed differences in sensory-motor neurocognitive assessments for that subject 192 and the average of subjects in the same age range. Differences in excess of two standard deviations of the average for that age group may be interpreted as being substantial. Substantial impairments may be taken to suggest some underlying pathophysiology. Specific patterns of impairments across sensory-motor neurocognitive assessments may be associated with specific pathophysiologies.

Figure 77:
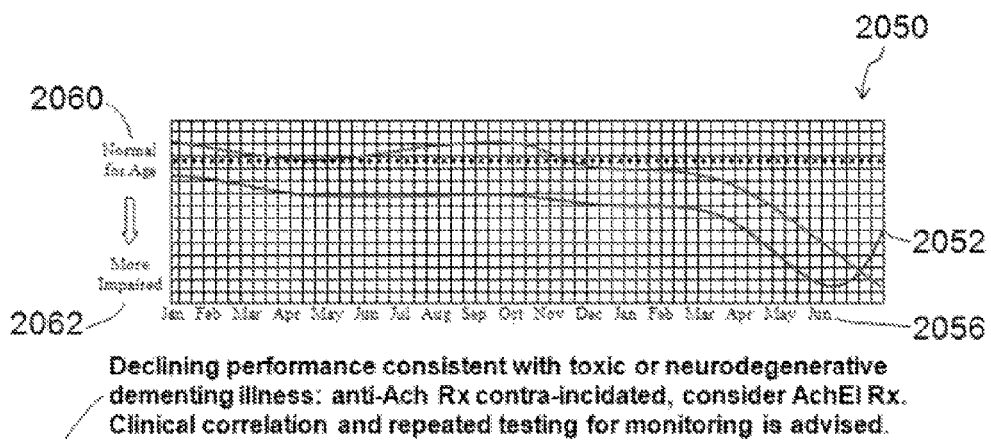
FIG. 77 provides an exemplary recommended diagnosis summary.

FIG. 77 provides an exemplary recommended diagnosis summary 2050, which may include a clinical diagnosis and/or a recommendation medications listing. The recommended diagnosis summary 2050 may include, but is not limited to, a functional impairment characteristic profile 2052 and a recommended diagnosis 2054. The functional impairment characteristic profile 2052 may be shown graphically on a plot of the rating of the functional impairment characteristic versus the calendar time range 2056. More particularly, the scale for the rating of the functional impairment characteristic of the functional impairment characteristic profile 2052 may range from normal for age 2060 to more impaired 2062.

In summary, the present disclosure teaches a method, system, and tangible computer readable medium for addressing quantitative assessment of functional impairment in a subject. An apparatus for quantifying assessment of functional impairment in a subject comprising an input device, a display device, a control device, and a tangible computer readable medium. A hierarchical system of functional impairment tests that quantitatively measures the response characteristics of the brain in the subject.

The present disclosure is applicable towards neurological diagnostics, ophthalmological diagnostics, psychiatric diagnostics, medical and surgical diagnostics, disease progression monitoring, treatment monitoring, side-effects monitoring, human developmental applications, human performance in educational applications, public health assessments, human performance assessment related to social analysis, insurance evaluations, human resources evaluations, task readiness assessments, animal health and research, coupling with genomics, coupling with neuroimaging, coupling with neurophysiology, coupling with neurochemistry, and coupling with basic science research.

More particularly and with regards towards neurological diagnostics, the present disclosure may be applicable towards diagnosis of diseases and disorders affecting perception, behavior, and cognition. Further, the present disclosure may be applicable towards the early detection and diagnosis of dementias related to Alzheimer's disease and its precursors syndromes that include mild cognitive impairment and age-associated memory impairment and other diagnostic sub-types of related pathologies.

Further, the present disclosure may be applicable towards the early detection and diagnosis of fronto-temporal dementias and precursor syndromes and sub-syndromes that include frontal lobar, temporal lobar, and Pick's dementias and other diagnostic sub-types of related pathologies.

Further, the present disclosure may be applicable towards the early detection and diagnosis of Parkinsonism, and its precursors syndromes and related disorders that include Parkinsonian dementias and other movement disorders in the rigid-bradykinetic syndromic spectrum and related pathologies.

Further, the present disclosure may be applicable towards the early detection and diagnosis of cerebrovascular disorders with central manifestations of overt stroke or of the manifestations of the transient, sub-acute, or chronic abnormal perfusion of brain tissue.

Further, the present disclosure may be applicable towards the early detection and diagnosis of the neurological manifestations of exposure to toxic substances including poisons, combustion products, and environmental hazards and extremes including chemicals and radiation.

Further, the present disclosure may be applicable towards the early detection and diagnosis of the neurological manifestations of changes in endogenous or artificial hormones resulting from natural progression through the life-cycle or from therapeutic or iatrogenic changes in hormonal effects.

Further, the present disclosure may be applicable towards the early detection and diagnosis of neurological disorders in young people including attention deficit disorders, hyperactivity disorders, and disorders of specific functional or learning impairments.

More particularly and with regards towards ophthalmological diagnostics, the present disclosure may be applicable towards the diagnosis of ophthalmological diseases and disorders. Further, the present disclosure may be applicable towards the early detection and diagnosis of ocular disease and their precursors syndromes that include disorders of the cornea, lens, and vitreous and their supportive tissues in the eye.

Further, the present disclosure may be applicable towards the early detection and diagnosis of disorders of aqueous fluid dynamics, such as glaucoma, and related disorders of intrinsic, traumatic, or iatrogenic etiology affecting aqueous generation, passage, or resorption.

Further, the present disclosure may be applicable towards the early detection and diagnosis of disorders of the retina and its supportive tissues including exposures to toxins and radiation, inherited disorders of the retina, trauma to the retina, and deformations of retinal structure or function.

Further, the present disclosure may be applicable towards the early detection and diagnosis of disorders of the pathways leading from the eye and to the brain centers responsible for processing visual signals.

Further, the present disclosure may be applicable towards the early detection and diagnosis of disorders of the brain centers, nerves, and muscles responsible for stably maintaining the position and movement of the eye that result in the ability to control gaze direction and conjugacy.

More particularly and with regards towards psychiatric diagnostics, the present disclosure may be applicable towards the early detection and diagnosis of affective disease and their precursors syndromes that include major depression, bipolar illnesses, and the affective manifestations of other psychiatric disorders.

Further, the present disclosure may be applicable towards the early detection and diagnosis of disorders of psychotic disorders that include psychiatric disorders in the spectrum of schizophrenia as well as psychotic disorders that are the result of other illnesses, acute or chronic.

Further, the present disclosure may be applicable towards the early detection and diagnosis of disorders in the spectrum of autism, Asperger's, and Williams syndromes and related psychiatric disorders caused by inherited or non-inherited genetic disorders and early life mis- or mal-formations.

More particularly and with regards towards medical and surgical diagnostics, the present disclosure may be applicable towards the diagnosis of functional complications of medical and surgical disorders, such as with the early detection and diagnosis of functional complications of cardiopulmonary disease including those that result in the hypoperfusion and hypo-oxygenation of the brain in an acute, sub-acute, or chronic, temporary or permanent manner.

Further, the present disclosure may be applicable towards the early detection and diagnosis of functional complications of urinary-renal or gastrointestinal disorders including conditions that alter the absorption, accumulation, metabolism, or elimination of endogenous or exogenous toxins.

Further, the present disclosure may be applicable towards the early detection and diagnosis of functional complications of closed or penetrating head trauma in an acute, sub-acute, or chronic, temporary or permanent manner.

Further, the present disclosure may be applicable towards the early detection and diagnosis of functional complications of surgical procedures that alter brain function directly or indirectly in an acute, sub-acute, or chronic, temporary or permanent manner.

Further, the present disclosure may be applicable towards the early detection and diagnosis of functional complications of anesthesiological procedures that alter brain function directly or indirectly in an acute, sub-acute, or chronic, temporary or permanent manner.

More particularly and with regards towards disease progression monitoring, the present disclosure may be applicable towards the qualitative or quantitative monitoring of the regression, stabilization, or progression of functional disorders as a consequence of changes in the pathophysiology causing those functional disorders.

More particularly and with regards towards treatment monitoring, the present disclosure may be applicable towards the qualitative or quantitative monitoring of the improvement, stabilization, or lack of improvement or stabilization in functional disorders as a consequence of therapeutic interventions.

More particularly and with regards towards side-effects monitoring, the present disclosure may be applicable towards the declines in function as the result of interventional side-effects that would include side-effects of neuro-active and non-neuro-active treatments that may constitute common, or idiosyncratic reactions.

More particularly and with regards towards human developmental applications, the present disclosure may be applicable towards the qualitative or quantitative assessment of human development in a medical or educational setting to determine an individual's development status, further development, or departure from expected patterns and rates of development either across functional domains or with limited functional domains.

More particularly and with regards towards human performance in educational applications, the present disclosure may be applicable towards the qualitative or quantitative assessment of human performance in an educational setting to determine an individual's suitability for an educational program or need for alternatives, and of therapeutic or other exogenous factors' influence on suitability for educational programs.

More particularly and with regards towards public health assessments, the present disclosure may be applicable towards the qualitative or quantitative assessment of human performance in the setting of public health to monitor the health of select or broadly defined groups, and for comparisons across groups undergoing treatments, exposures, or other factors that may impact on human performance.

More particularly and with regards towards human performance assessment related to social analysis, the present disclosure may be applicable towards qualitative or quantitative assessment of human performance in the setting of efforts to understand differences between socially defined or socially recognized populations reflecting endogenous differences or the impact of exogenous factors such as stress, cultural changes, or other events.

More particularly and with regards towards insurance evaluations, the present disclosure may be applicable towards the qualitative or quantitative assessment of human functional capacities as an indication of their risk of developing impairments, and as an indication of their need for access to medical or other resources.

More particularly and with regards towards human resources evaluations, the present disclosure may be applicable towards the qualitative or quantitative assessment of human performance in the setting of human resources evaluations related to hiring individuals well-suited to specific tasks.

More particularly and with regards towards task readiness assessments, the present disclosure may be applicable towards the qualitative or quantitative assessment of human performance in the setting of readiness to perform critical tasks that might be subject to endogenous or exogenous variation in readiness to perform that task, these would include the effects of sleep status and therapeutic or non-therapeutic medicines or other exposures.

More particularly and with regards towards animal health and research, the present disclosure may be applicable towards the qualitative or quantitative assessment of an animal's functional capacities in many contexts that include: assessment of an animal's functional health or of a group of animal's health in the context of veterinary medical or veterinary population health applications, assessment of the impact of potentially therapeutic interventions on an animal's functional health, either in the context of a veterinary medical application or for evaluations of interventions for potential human applications, or assessment of a toxic exposure on an animal's functional health, either in the context of a veterinary medical application or for evaluations of the potential consequences of human exposures.

More particularly and with regards towards coupling with genomics, the present disclosure may be applicable towards the qualitative or quantitative assessment of human performance in relation to molecular or chemical analyses of human differences and their relationship to performance including analyses of chemical and genetic factors that may influence performance in isolation or in combination with other factors.

More particularly and with regards towards coupling with neuroimaging, the present disclosure may be applicable towards the qualitative or quantitative assessment of human performance in the setting of technologically mediated assessments of brain structure and function by imaging modalities including, but not limited to, the analysis of normal, variant, or pathological anatomy or physiology by radiological imaging, magnetic imaging, radioactive isotope imaging, and thermal imaging.

More particularly and with regards towards coupling with neurophysiology, the present disclosure may be applicable towards the qualitative or quantitative assessment of human performance in the setting of technologically mediated assessments of brain structure and function by electrical or magnetic field measurements of normal, variant, or pathological anatomy or physiology by resting or activated activity.

More particularly and with regards towards coupling with neurochemistry, the present disclosure may be applicable towards the qualitative or quantitative assessment of human performance in the setting of technologically mediated assessments of brain chemistry and metabolism by direct sampling of brain or other neural tissue, sampling cerebrospinal fluid, or sampling of other bodily fluids or derivatives.

More particularly and with regards towards coupling with basic science research, the present disclosure may be applicable towards the qualitative or quantitative human performance in the context of basic scientific research on the subject of human performance or on other subjects in which human performance relations are relevant.

All references, including publications, patent applications, and patents, cited herein are hereby incorporated by reference to the same extent as if each reference were individually and specifically indicated to be incorporated by reference and were set forth in its entirety herein.

The methods and process flows of the disclosed subject matter that are associated with the computer readable medium may be described in the general context of computer-executable instructions, such as program modules, being executed by a computer. Generally, program modules include routines, programs, objects, components, data structures, etc. that performs particular tasks or implement particular abstract data types. The disclosed subject matter may also be practiced in distributed computing environments wherein tasks are performed by remote processing devices that are linked through a communications network. In a distributed computing environment, program modules may be located in local and/or remote computer storage media including memory storage devices.

The detailed description set forth below in connection with the appended drawings is intended as a description of exemplary embodiments in which the presently disclosed process can be practiced. The term "exemplary" used throughout this description means "serving as an example, instance, or illustration," and should not necessarily be construed as preferred or advantageous over other embodiments.

The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system.

The foregoing description of the disclosed embodiments is provided to enable any person skilled in the art to make or use the claimed subject matter. Various modifications to these embodiments will be readily apparent to those skilled in the art, and the generic principles defined herein may be applied to other embodiments without the use of the innovative faculty. Thus, the claimed subject matter is not intended to be limited to the embodiments shown herein but is to be accorded the widest scope consistent with the principles and novel features disclosed herein. It is contemplated that additional embodiments are within the spirit and true scope of this disclosed method and system as claimed below.

What is claimed is:

1. A method for assessing the onset or progression of impairment in the nervous system functioning of a subject associated with a possible nervous system disorder, injury, derangement, or toxicity, said impairment associated with brain functioning in a desired stimulus domain and relating to various different physical areas of a subject's brain, the method comprising the steps of:

performing a spatial sequence memory test on a computer screen using a user interface for variably and selectably determining a lowest signal-to-noise ratio and stimulus sequence durations at which a subject can accurately and consistently identify a target stimulus from at least one non-target stimulus, wherein said user interface comprises a set of specific patterns of visual form or motion, and further wherein said target stimulus aligns with a stimulus domain and a predetermined physical portion of the subject's brain for which a test is desired and further wherein said target stimulus associates with a task design involving the subject's ability to process said target stimulus corresponding to the operational performance of a predetermined physical area of the subject's brain;

further wherein said variable and selectable spatial sequence memory test manipulates a task difficulty associated with visual form or motion characteristics of said specific stimulus pattern, said variable and selectable spatial sequence memory test further comprising the following steps executed on a computer processor:

presenting at least two stimuli simultaneously such that one of said at least two stimuli comprises the target stimulus satisfying a given target criterion for associating with the desired stimulus domain and physical portion of the subject's brain and the other one(s) of said at least two stimuli comprises the at least one non-target stimulus not satisfying said given target criterion;

moving a position of said target stimulus and said non-target stimulus on said computer screen according to said set of specific pattern of visual form or motion while changing a signal-to-noise ratio of all of said at least two stimuli in response to responses from the subject;

monitoring the speed and accuracy of the subject's indication of said position of said target stimulus as said target stimulus moves along said specific pattern of visual form or motion and said signal-to-noise ratio and stimulus sequence duration changes;

analyzing the subject's positional error with respect to said position of said target stimulus and observed subject response motion dynamics errors associated with the subject's ability to respond to said movement of said target stimulus and from said analyzing relating to the stimulus domain and physical portion of the subject's brain;

adjusting the signal-to-noise ratio relating to said target stimulus and non-target stimulus wherein the signal-to-noise ratio is increased until the subject has correctly identified the target stimuli in response to said analyzing step for assessing the subject's responses to said target stimulus as a relationship to the subject's mental processing abilities in the desired stimulus domain and physical portion of the subject's brain;

creating a subject score deriving from the subject's accuracy, speed, and precision in responding to said changes in said signal-to-noise ratios and stimulus sequence durations of said at least two stimuli relating to the function of the subject's stimulus domain and operational performance of a physical portion of the subject's brain;

adjusting said subject score relative to a normal range derived from at least one comparison subject group studied under at least one stimulus condition;

deriving critical performance parameters from said subject score, said critical performance parameters relating to the stimulus domain and operational performance of a physical portion of the subject's brain for deriving information associated with brain functional disorders or injury from diverse causes in the subject;

controllably recording and displaying on said computer screen said critical performance parameters and confidence interval parameters associated with said critical performance parameters; and using said critical performance parameters in assessing, evaluating, or determining a possible presence, onset, progression, or therapeutic response of performance impairments related to the central nervous system functioning of the subject and relating to the stimulus domain and operational performance of a physical portion of the subject's brain.

2. The method of claim 1, wherein said step of presenting is repeated more than once.

3. The method of claim 1, wherein said step of moving a position of said stimuli is associated with a change in saliency, wherein saliency refers to a means by which behavior is modified regardless of whether the subject is consciously aware.

4. The method of claim 1, wherein a modulated saliency is associated with a high saliency, further wherein the difficulty of a task for a subject is altered.

5. The method of claim 1, wherein a modified saliency is reverted to the original saliency, further wherein the difficulty of a task for a subject is altered.

6. The method of claim 1, wherein said critical performance parameters are associated with an enhanced ability in said subject to follow a target.

7. The method of claim 6, wherein said enhanced ability is associated with at least one of the following:
sequence memory, location memory, and learning ability.

8. The method of claim 1, wherein said movement is discontinuous, further wherein said discontinuous movement comprises the target stimulus fading from a location in a letter identification latency module and emerging at a new location in said letter identification latency module.

9. The method of claim 1, wherein said movement is continuous, further wherein said continuous movement comprises the target stimulus moving around an edge of a circular stimulus area.

10. The method of claim 1, wherein said movement is moved to a random location on a scene, wherein said scene is presented to a subject.

11. The method of claim 1, wherein said adjusted signal-to-noise ratio is associated with at least one of the following: direction, center of motion, shape, size, and cueing.

12. The method of claim 1, wherein said adjusted signal-to-noise ratio is associated with motion.

13. The method of claim 1, wherein said critical performance parameters are implemented in a different functional impairment assessment test.

14. An apparatus for assessing the onset or progression of impairment in the nervous system functioning of a subject associated with a possible nervous system disorder, injury, derangement, or toxicity, said impairment associated with brain functioning in a desired stimulus domain and relating to various different physical areas of a subject's brain, the apparatus comprising:

a user interface on a computer screen configured to perform a spatial sequence memory test for variably and selectably determining a lowest signal-to-noise ratio and stimulus sequence durations at which a subject can accurately and consistently identify a target stimulus from at least one non-target stimulus, wherein said user interface comprises a set of specific patterns of visual form or motion, and further wherein said target stimulus aligns with a stimulus domain and a predetermined physical portion of the subject's brain for which a test is desired and further wherein said target stimulus associates with a task design involving the subject's ability to process said target stimulus corresponding to the operational performance of a predetermined physical area of the subject's brain;

further wherein said variable and selectable spatial sequence memory test manipulates a task difficulty associated with visual form or motion characteristics of said specific stimulus pattern, said variable and selectable spatial sequence memory test further comprising the following steps executed on a computer processor:

the user interface on a computer screen configured to present at least two stimuli simultaneously such that one of said at least two stimuli comprises the target stimulus satisfying a given target criterion for associating with the desired stimulus domain and physical portion of the subject's brain and the other one(s) of said at least two stimuli comprises the at least one non-target stimulus not satisfying said given target criterion;

the user interface on a computer screen configured to move a position of said target stimulus and said non-target stimulus on said computer screen according to said set of specific pattern of visual form or motion while changing a signal-to-noise ratio of all of said at least two stimuli in response to responses from the subject;

the user interface on a computer screen configured to monitor the speed and accuracy of the subject's indication of said position of said target stimulus as said target stimulus moves along said specific pattern of visual form or motion and said signal-to-noise ratio and stimulus sequence duration changes;

the user interface on a computer screen configured to analyze the subject's positional error with respect to said position of said target stimulus and observed subject response motion dynamics errors associated with the subject's ability to respond to said movement of said target stimulus and from said analyzing relating to the stimulus domain and physical portion of the subject's brain;

the user interface on a computer screen configured to adjust the signal-to-noise ratio relating to said target stimulus and non-target stimulus wherein the signal-to-noise ratio is increased until the subject has correctly identified the target stimuli in response to said analyzing step for assessing the subject's responses to said target stimulus as a relationship to the subject's mental processing abilities in the desired stimulus domain and physical portion of the subject's brain;

the user interface on a computer screen configured to create a subject score deriving from the subject's accuracy, speed, and precision in responding to said changes in said signal-to-noise ratios and stimulus sequence durations of said at least two stimuli relating to the function of the subject's stimulus domain and operational performance of a physical portion of the subject's brain;

the user interface on a computer screen configured to adjust said subject score relative to a normal range derived from at least one comparison subject group studied under at least one stimulus condition;

the user interface on a computer screen configured to derive critical performance parameters from said subject score, said critical performance parameters relating to the stimulus domain and operational performance of a physical portion of the subject's brain for deriving information associated with brain functional disorders or injury from diverse causes in the subject;

the user interface on a computer screen configured to controllably record and display on said computer screen said critical performance parameters and confidence interval parameters associated with said critical performance parameters; and the user interface on a computer screen configured to use said critical performance parameters in assessing, evaluating, or determining a possible presence, onset, progression, or therapeutic response of performance impairments related to the central nervous system functioning of the subject and relating to the stimulus domain and operational performance of a physical portion of the subject's brain.

15. The apparatus of claim 14, wherein said user interface presents, more than once, said at least two stimuli simultaneously.

16. The apparatus of claim 14, wherein said movement is discontinuous, further wherein said discontinuous movement comprises the target stimulus fading from a location in a letter identification latency module and emerging at a new location in said letter identification latency module.

17. The apparatus of claim 14, wherein said movement is continuous, further wherein said continuous movement comprises the target stimulus moving around an edge of a circular stimulus area.

18. The apparatus of claim 14, wherein a random section of the user interface is moved to a random location on a scene, wherein said scene is presented to a subject.

19. The apparatus of claim 14, wherein said critical performance parameters are implemented in a different functional impairment assessment test.

* * * * *